US011883496B2

(12) United States Patent
Chan et al.

(10) Patent No.: US 11,883,496 B2
(45) Date of Patent: Jan. 30, 2024

(54) INJECTABLE PH 7 SOLUTION COMPRISING AT LEAST ONE BASAL INSULIN HAVING A PI FROM 5.8 TO 8.5 AND A CO-POLYAMINO ACID BEARING CARBOXYLATE CHARGES AND HYDROPHOBIC RADICALS

(71) Applicant: ADOCIA, Lyons (FR)

(72) Inventors: You-Ping Chan, Ternay (FR); Alexandre Geissler, Lyons (FR); Romain Noel, Villeurbanne (FR); Richard Charvet, Rillieux la Pape (FR); Nicolas Laurent, Miribel (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 16/902,176

(22) Filed: Jun. 15, 2020

(65) Prior Publication Data

US 2020/0306379 A1 Oct. 1, 2020

Related U.S. Application Data

(63) Continuation of application No. 16/213,809, filed on Dec. 7, 2018, now abandoned.

(60) Provisional application No. 62/606,138, filed on Dec. 7, 2017.

(30) Foreign Application Priority Data

Dec. 7, 2017 (FR) ..................................... 17/61807
Jun. 29, 2018 (FR) ..................................... 18/55934

(51) Int. Cl.
| | |
|---|---|
| A61K 38/28 | (2006.01) |
| A61K 47/34 | (2017.01) |
| A61K 47/62 | (2017.01) |
| C07K 14/62 | (2006.01) |
| A61P 3/08 | (2006.01) |
| A61K 9/50 | (2006.01) |
| A61K 9/20 | (2006.01) |
| A61K 9/00 | (2006.01) |
| C08G 69/10 | (2006.01) |
| A61K 47/42 | (2017.01) |

(52) U.S. Cl.
CPC ............ *A61K 47/34* (2013.01); *A61K 9/0019* (2013.01); *A61K 9/2045* (2013.01); *A61K 9/5084* (2013.01); *A61K 38/28* (2013.01); *A61K 47/42* (2013.01); *A61K 47/62* (2017.08); *A61P 3/08* (2018.01); *C07K 14/62* (2013.01); *C08G 69/10* (2013.01)

(58) Field of Classification Search
CPC ........ A61K 38/28; A61K 47/34; A61K 47/62; C08G 69/10; C08G 69/48; C08L 77/04
See application file for complete search history.

(56) References Cited

U.S. PATENT DOCUMENTS

| | | |
|---|---|---|
| 5,124,314 A | 6/1992 | Cooper |
| 5,234,906 A | 8/1993 | Young et al. |
| 5,656,722 A | 8/1997 | Dorschug |
| 5,866,538 A | 2/1999 | Norup et al. |
| 6,100,376 A | 8/2000 | Dorschug |
| 10,383,920 B2 | 8/2019 | Geissler et al. |
| 10,548,952 B2 | 2/2020 | Geissler et al. |
| 11,633,460 B2 | 4/2023 | Chan et al. |
| 2006/0099264 A1 | 5/2006 | Chan et al. |
| 2007/0010652 A1 | 1/2007 | Angot et al. |
| 2007/0248686 A1 | 10/2007 | Touraud et al. |
| 2008/0152675 A1 | 6/2008 | Pouliquen |
| 2013/0065826 A1 | 3/2013 | Soula et al. |
| 2013/0178415 A1 | 7/2013 | Soula |
| 2014/0187499 A1 | 7/2014 | Soula et al. |
| 2014/0249079 A1 | 9/2014 | Soula et al. |
| 2014/0348767 A1 | 11/2014 | Hanabusa et al. |
| 2015/0320876 A1 | 11/2015 | Chen et al. |
| 2016/0030672 A1 | 2/2016 | Manderscheid et al. |
| 2016/0213707 A1 | 7/2016 | Hedrick et al. |
| 2017/0216405 A1 | 8/2017 | Sjogren et al. |
| 2017/0348396 A1 | 12/2017 | Geissler |
| 2017/0348423 A1 | 12/2017 | Geissler |
| 2018/0193421 A1 | 7/2018 | Soula |
| 2019/0216931 A1 | 7/2019 | Chan |
| 2019/0274953 A1 | 9/2019 | Geissler |
| 2019/0274954 A1 | 9/2019 | Chan et al. |
| 2019/0275109 A1 | 9/2019 | Chan et al. |
| 2019/0275115 A1 | 9/2019 | Chan et al. |
| 2019/0275156 A1 | 9/2019 | Chan et al. |
| 2019/0328842 A1 | 10/2019 | Chan et al. |
| 2019/0388515 A1 | 12/2019 | Geissler et al. |
| 2020/0179489 A1 | 6/2020 | Geissler |

(Continued)

FOREIGN PATENT DOCUMENTS

| | | |
|---|---|---|
| CA | 2377211 A1 | 1/2001 |
| CN | 101563066 A | 10/2009 |

(Continued)

OTHER PUBLICATIONS

Sep. 22, 2020 Office Action issued in U.S. Appl. No. 16/213,963.
Oct. 7, 2020 Office Action Issued in U.S. Appl. No. 16/213,748.
Jun. 9, 2020 English Translation of International Preliminary Report on Patentability issued in International Patent Application No. PCT/EP2018/083558.
Deming, Timothy J. "Polypeptide and Polypeptide Hybrid Copolymer Synthesis via NCA Polymerization". Advances in Polymer Science, vol. 202, pp. 1-18, 2006.
Deming, Timothy J. "Facile synthesis of block copolypeptides of defined architecture". Nature, vol. 390, pp. 386-389, 1997.

(Continued)

*Primary Examiner* — Jeffrey E. Russel
(74) *Attorney, Agent, or Firm* — Oliff PLC

(57) ABSTRACT

A physically stable compositions in the form of an injectable aqueous solution with a pH from 6.0 to 8.0, include a basal insulin whose isoelectric point (pI) is from 5.8 to 8.5, and a co-polyamino acid bearing carboxylate charges and at least one hydrophobic radical.

24 Claims, No Drawings

(56) References Cited

U.S. PATENT DOCUMENTS

| | | | |
|---|---|---|---|
| 2020/0306379 A1 | 10/2020 | Chan et al. | |
| 2021/0205417 A1 | 7/2021 | Geissler | |

FOREIGN PATENT DOCUMENTS

| | | | |
|---|---|---|---|
| EP | 3 347 724 A1 | 12/1989 | |
| EP | 3 499 521 A1 | 8/1992 | |
| EP | 1063254 A1 | 12/2000 | |
| FR | 2 801 226 A1 | 5/2001 | |
| FR | 2 840 614 A1 | 12/2003 | |
| FR | 2 843 117 A1 | 2/2004 | |
| FR | 2 873 704 A1 | 2/2006 | |
| FR | 2 885 521 A1 | 11/2006 | |
| FR | 2 910 318 A1 | 6/2008 | |
| FR | 2 985 428 A1 | 7/2013 | |
| FR | 2 985 429 A1 | 7/2013 | |
| FR | 2985428 A1 | 7/2013 | |
| FR | 3 001 896 A1 | 8/2014 | |
| FR | 3 052 071 A1 | 12/2017 | |
| JP | 2007510005 A | 4/2007 | |
| JP | 2021505616 A | 2/2021 | |
| WO | 2003/005339 A1 | 1/2003 | |
| WO | 2004/096854 A2 | 11/2004 | |
| WO | 2009/077844 A2 | 6/2009 | |
| WO | 2009/077844 A3 | 11/2009 | |
| WO | 2013/021143 A1 | 2/2013 | |
| WO | 2013/104861 A1 | 7/2013 | |
| WO | 2014/124993 A1 | 8/2014 | |
| WO | 2014/124994 A1 | 8/2014 | |
| WO | 2015/114171 A1 | 8/2015 | |
| WO | 2017/211916 A1 | 12/2017 | |
| WO | 2017/211917 A1 | 12/2017 | |
| WO | 2018/122278 A1 | 7/2018 | |
| WO | 2019/110773 A1 | 6/2019 | |
| WO | WO-2019110773 A1 * | 6/2019 | ............. A61K 38/28 |

OTHER PUBLICATIONS

Lu, Hua et al. "Hexamethyldisilazane-Mediated Controlled Polymerization of a-Amino Acid N-Carboxyanhydrides". Journal of the American Chemical Society, vol. 129, pp. 14114-14115, 2007.
Lu, Hua et al. "N-Trimethylsilyl Amines for Controlled Ring-Opening Polymerization of Amino Acid N-Carboxyanhydrides and Facile End Group Functionalization of Polypeptides". Journal of the American Chemical Society, vol. 130, pp. 12562-12563, 2008.
Bhatnagar, Pradip K. et al. "Structure-Activity Relationships of Novel Hematoregulatory Peptides". Journal of Medicinal Chemistry, vol. 39, pp. 3814-3819, 1996.
Hoppmann, Christian et al. "Intramolecular bridges formed by photoswitchable click amino acids". Beilstein Journal of Organic Chemistry, vol. 8, pp. 884-889, 2012.
Burnett, Christina L. et al. "Safety Assessment of Amino Acid Alkyl Amides as Used in Cosmetics". International Journal of Toxicology, vol. 36, pp. 17S-56S, 2017.
Wu, Chuanliu et al. "Interplay of Chemical Microenvironment and Redox Environment on Thiol-Disulfide Exchange Kinetics". Chemistry: A European Journal, vol. 17, pp. 10064-10070, 2011.
Liang, Jing et al. "Distinct optical and kinetic responses from E/Z isomers of caspase probes with aggregation-induced emission characteristics". Journal of Materials Chemistry B., vol. 2, pp. 4363-4370, 2014.
Liu, Jixiang et al.; "Fluorescent Molecular Probes V: A Sensitive Caspase-3 Substrate for Fluorometric Assays;" Bioorganic & Medicinal Chemistry Letters; vol. 9, pp. 3231-3236, 1999.
Leishman, Emma et al.; "Lipidomics profile of a NAPE-PLD KO mouse provides evidence of a broader role of this enzyme in lipid metabolism in the brain". Biochimica et Biophysica Acta; vol. 1861, pp. 491-500, 2016.
Schlitzer, Martin et al. "Non-peptidic, Non-prenylic Bisubstrate Farnesyltransferase Inhibitors, 4. Effect on Farnesyltransferase Inhibitory Activity of Conformational Restrictions in the Central Group". Pharmacy and Pharmacology Communications, vol. 5, pp. 117-124, 2000.

Sep. 28, 2018 Search Report issued in French Patent Application No. 1761807.
Feb. 13, 2019 International Search Report issued in International Patent Application No. PCT/EP2018/083896.
Feb. 4, 2019 International Search Report issued in International Patent Application No. PCT/EP2018/083897.
Subramanian, G. et al. "Structure of Complexes of Cationic Lipids and Poly(Glutamic Acid) Polypeptides: A Pinched Lamellar Phase". Journal of the American Chemical Society, vol. 122, pp. 26-34, 2000.
U.S. Appl. No. 16/212,960, filed Dec. 7, 2018 in the name of Geissler.
U.S. Appl. No. 16/213,963, filed Dec. 7, 2018 in the name of Geissler.
U.S. Appl. No. 16/213,748, filed Dec. 7, 2018 in the name of Chan et al.
U.S. Appl. No. 16/213,809, filed Dec. 7, 2018 in the name of Chan et al.
Oct. 25, 2019, Office Action issued in Pakistani Application No. 839/2018.
Nov. 11, 2019 Office Action issued in Pakistani Application No. 840/2018.
Jan. 8, 2020 Office Action issued in U.S. Appl. No. 16/213,748.
Kaushik et al., "Why is Trehalose an Exceptional Protein Stabilizer", Journal of Biological Chemistry, 2003, vol. 278. No. 29, pp. 26458-26465.
Feb. 10, 2020 Office Action issued in U.S. Appl. No. 16/213,963.
C1266WW00 Recherche AA(STN), Nov. 24, 2016, pp. 1-11.
Finsinger et al., "Protective copolymers for nonviral gene vectors: synthesis, vector characterization and application in gene delivery," Gene Therapy, No. 7, 2000, pp. 1183-1192.
Wang et al., "Synthesis of y-Benzyl-a,L-glutamate Oligomers and their Star Derivatives," American Chemical Society, Polymer Preprints, Division of Polymer Chemistry, 1996, 37: 622-623.
Dec. 13, 2019 Office Action issued in U.S. Appl. No. 16/213,809.
Jul. 6, 2021 Office Action Issued in U.S. Appl. No. 16/213,748.
Kokotos et al., Novel2-0xoamide Inhibitors of Human Group IVA Phospholipase A2, J. Med. Chem. 2002, 45, 2891-2893 (Year: 2002).
Mar. 30, 2022 Office Action issued in U.S. Appl. No. 16/213,748.
Sep. 8, 2021 Office Action in Eurasian Patent Office Patent Application No. 202091374.
Carbonization—Wikipedia (Apr. 13, 2022).
Amine—Wikipedia (Apr. 13, 2022).
Ethylenediamine—Wikipedia (Apr. 13, 2022).
Jan. 5, 2022 Office Action in Chinese Patent Application No. 201880084782.8.
Dec. 21, 2021 Office Action in Eurasian Patent Application No. 202091394.
Feb. 21, 2022 Examination Report in Pakistani Patent Application No. 840/2018.
Oct. 14, 2020 Office Action in Vietnamese Patent Application No. 1-2020-03916.
Dec. 16, 2021 Examination Report in Indian Patent Application No. 202017028528.
Sep. 14, 2020 Office Action in Vietnamese Patent Application No. 1-2020-03915.
Apr. 17, 2020 International Search Report in International Patent Application No. PCT/EP2019/084293.
Aug. 4, 2021 Office Action in Saudi Arabian Patent Application No. 520412142.
Jun. 21, 2021 Examination Report in Algerian Patent Appliation No. 200301.
Aug. 5, 2022 Office Action in Indonesian Patent Application No. P00202004885.
Nov. 17, 2022 Notice of Allowance issued in U.S. Appl. No. 16/213,748.
Dec. 1, 2022 Office Action issued in U.S. Appl. No. 17/208,514.
Sep. 1, 2022 Office Action Issued in Brazilian Patent Application No. BR1120200114863.
Jul. 5, 2021 Office Action Issued in European Patent Application No. 18812169.3.

(56) References Cited

OTHER PUBLICATIONS

Mar. 1, 2023 Office Action Issued in European Patent Application No. 18814899.3.
Jan. 11, 2023 Office Action Issued in Taiwanese Patent Application No. 107144180.
Nov. 6, 2018 Search Report Issued in European Patent Application No. 18181037.5.
Mar. 8, 2023 Office Action Issued in Mexican Patent Application No. MX/a/2020/005914.
Dec. 11, 2019 International Preliminary Report on Patentability issued in International Patent Application No. PCT/EP2018/083558.
Jul. 20, 2023 Office Action issued in U.S. Appl. No. 17/208,514.
Jan. 1, 2023 Search Report Issued in Taiwanese Patent Application No. 107144181.
Jan. 11, 2023 Office Action Issued in Taiwanese Patent Application No. 107144181.
Dec. 19, 2022 Office Action Issued in Chinese Patent Application No. 201880084782.8.
Dec. 19, 2023 Office Action Issued in Israeli Patent Application No. 275148.
Jan. 10, 2023 Office Action Issued in Japanese Patent Application No. 2020-531049.
Jun. 16, 2023 Office Action Issued in Saudi Arabian Patent Application No. 520412142.
Dec. 6, 2022 Office Action Issued in Uzbekistani Patent Application No. 20200296.
Jul. 5, 2021 Office Action Issued in European Patent Application No. EP18812169.3.
Jun. 22, 2021 Office Action Issued in Algerian Patent Application No. DZ/P/2020/000304.
Mar. 2, 2023 Office Action Issued in Indonesian Patent Application No. P00202004939.
May 23, 2023 Office Action Issued in Israeli Patent Application No. 275192.
Jan. 10, 2023 Office Action Issued in Japanese Patent Application No. 2020-531052.
Feb. 7, 2023 Office Action Issued in Kuwaiti Patent Application No. KW/P/2020/000255.
Dec. 16, 2022 Office Action Issued in Saudi Arabian Patent Application No. 520412141.
Aug. 22, 2022 Search Report Issued in Taiwanese Patent Application No. 107144180.
Dec. 15, 2022 Office Action Issued in Uzbekistani Patent Application No. 2020 0300/7.
Jun. 18, 2020 International Preliminary Report on Patentability issued in International Patent Application No. PCT/EP2018/083897.
Jul. 21, 2022 Office Action Issued in Saudi Arabian Patent Application No. 520412142.
Jun. 30, 2023 Office Action issued in Vietnamese Patent Application No. 33215/SHTT-SC.
Jul. 20, 2023 Office Action issued in Saudi Arabian Patent Application No. 520412141.
Assignment (Being Filed for Dual Purpose Under 37 CFR 1.63(e)), filed in in U.S. Appl. No. 16/770,787, (executed Sep. 2020).

* cited by examiner

INJECTABLE PH 7 SOLUTION COMPRISING AT LEAST ONE BASAL INSULIN HAVING A PI FROM 5.8 TO 8.5 AND A CO-POLYAMINO ACID BEARING CARBOXYLATE CHARGES AND HYDROPHOBIC RADICALS

This is a Continuation of application Ser. No. 16/213,809 filed Dec. 7, 2018, which claims the benefit of U.S. Provisional Application No. 62/606,138 filed Dec. 7, 2017, French Application No. 17/61807 filed Dec. 7, 2017, and French Application No. 18/55934 filed Jun. 29, 2018. The disclosure of the prior applications is hereby incorporated by reference herein in its entirety.

The invention concerns insulin injection therapies for treating diabetes.

The invention relates to physically stable compositions in the form of an injectable aqueous solution, the pH of which is comprised from 6.0 to 8.0, comprising at least one basal insulin whose isoelectric point (pI) is comprised from 5.8 to 8.5, and a co-polyamino acid bearing carboxylate charges and hydrophobic radicals.

Insulin therapy, or diabetes treatment by insulin injection, has in recent years seen remarkable progress, specifically due to the development of new insulins, with a better blood sugar correction in patients in comparison with human insulin, and which make possible improved simulation of the physiological activity of the pancreas.

When type II diabetes is diagnosed in a patient, treatment is implemented gradually. First, the patient takes oral anti-diabetics (OAD) such as Metformin. When OADs alone are no longer sufficient to control the level of glucose in the blood, a change in treatment must be made and, depending on patient specificities, different treatment combinations can be implemented. For example, the patient may be treated with insulin glargine-type basal insulin or insulin detemir, in addition to OADs, then, depending on the evolution of the disease, with basal insulin and prandial insulin.

Furthermore, today, in order to make the transition from treatments by OADs, when the latter are no longer able to control the level of glucose in the blood, to a basal insulin/prandial insulin treatment, injection of GLP-1 RA analogs is recommended.

GLP-1 RA, for Glucagon-Like Peptide-1 receptor agonists, are insulinotropic peptides or incretins, and belong to the family of gastro-intestinal hormones (or Gut Hormones) which stimulate the secretion of insulin when blood sugar is too high, for example, after a meal.

Gastro-intestinal hormones (Gut hormones) are also called satiety hormones. Specifically, they comprise GLP-1 RA (Glucagon like peptide-1 receptor agonist) and GIP (Glucose-dependent insulinotropic peptide), oxyntomodulin (a derivative of proglucagon), the peptide YY, amylin, cholecystokinin, pancreatic polypeptide (PP), ghrelin and enterostatin, which are peptidic or proteic structures. They also stimulate the secretion of insulin in response to glucose and fatty acids and are, therefore, as such, potential candidates for the treatment of diabetes.

Among these, the GLP-1 RA are those that have provided, to date, the best results in the development of drugs. They have made it possible for patients affected by type II diabetes to lose weight, while maintaining better control of their blood sugar.

Thus, GLP-1 RA analogs or derivatives have been developed, in particular to improve their stability.

On the other hand, in order to meet his daily insulin needs, a diabetic patient currently has available, schematically, two types of insulins with complementary actions: prandial insulins (or so-called rapid-acting insulins) and basal insulins (or so-called slow-acting insulins).

Prandial insulins allow rapid management (metabolization and/or storing) of the glucose provided during meals and snacks. The patient must inject himself with a prandial insulin before each food intake, or about 2 to 3 injections per day. The most widely used prandial insulins are: recombinant human insulin, NovoLog® (NOVO NORDISK insulin aspart), Humalog® (ELI LILLY insulin aspart) and Apidra® (SANOFI insulin glulisine).

Basal insulins ensure the maintenance of the patient's glycemic homeostasis outside the periods of food intake. Essentially, they act to block the production of endogenous glucose (hepatic glucose). The daily dose of basal insulin generally corresponds to 40-50% of the total daily insulin needs. Depending on the basal insulin used, this dose is dispensed in 1 or 2 injections, regularly distributed over the course of the day. The most commonly used basal insulins are Levemir® (NOVO NORDISK insulin detemir) and Lantus® (SANOFI insulin glargine).

In the interest of being thorough, it should be noted that NPH (insulin NPH for Neutral Protamine Hagedorn; Humiline NPH®, Insulatard®) is the oldest basal insulin. This formulation is derived from precipitating human insulin (anionic at neutral pH) by a cationic protein, protamine. The microcrystals formed in this process are dispersed in an aqueous suspension and dissolve slowly after subcutaneous injection. This slow dissolution ensures extended insulin release. However, this release does not ensure a constant concentration of insulin over time. The release profile is bell-shaped and lasts only from 12 to 16 hours. Therefore, it is injected twice a day. This NPH basal insulin is much less effective than the modern basal insulins, Levemir® and Lantus®. NPH is an intermediate-acting basal insulin.

The principle of NPH evolved with the appearance of rapid insulin analogs which include products called "Premix" offering both rapid action and intermediate action. Novolog Mix® (NOVO NORDISK) and Humalog Mix® (ELI LILLY) are formulations comprising a rapid insulin analog, Novolog® and Humalog®, partially complexed with protamine. Thus, these formulations contain insulin analog microcrystals, whose action is called intermediary, and a part of the insulin that remained soluble whose action is rapid. These formulations do offer the advantage of a rapid acting insulin, but they also have the disadvantage of NPH, namely, a duration of action limited to from 12 to 16 hours, and insulin released in a "bell" curve. However, these products allow the patient to inject an intermediate action basal insulin with a rapid-action prandial insulin. However, numerous patients are concerned about reducing the number of their injections.

Basal insulins currently on the market may be classified according to the technical solution that allows to obtain extended action and, presently, two approaches are used.

The first, that of insulin detemir, is the binding to albumin in vivo. It is an analog, soluble at pH 7, which comprises a fatty acid side chain (tetradecanoyl) attached to position B29 which, in vivo, allows this insulin to associate with albumin. Its extended action is principally due to this affinity for albumin after subcutaneous injection.

However, its pharmacokinetic profile does not allow it to last an entire day, so that it is most frequently used in two injections per day.

Another insulin soluble at pH 7 is insulin degludec, marketed under the name Tresiba®[d]. It also comprises a fatty acid side chain attached to the insulin (hexadecandioyl-γ-L-Glu).

The second, that of insulin glargine, is the precipitation at physiological pH. Insulin glargine is an analog of human insulin obtained by elongation of the C-terminal part of the B chain of human insulin by two arginine residues, and by substitution of the asparagine residue A21 with a glycine residue (U.S. Pat. No. 5,656,722). The addition of two arginine residues was designed to adjust the pI (isoelectric point) of insulin glargine to the physiological pH, and thus to make this analog to human insulin insoluble in the physiological medium.

In addition, the substitution of A21 was designed in order to make insulin glargine stable at acidic pH and to thus be able to formulate it in the form of an injectable solution at acidic pH. At the time of sub-cutaneous injection, the passage of insulin glargine from an acidic pH (pH 4-4.5) to a physiological pH (neutral pH) causes its precipitation under the skin. The slow redissolution of microparticles of insulin glargine ensures a slow and extended action.

The blood sugar lowering effect of insulin glargine is quasi-constant over a 24-hour period which allows most patients to only inject themselves once a day.

Insulin glargine is considered today as the most widely used basal insulin.

However, the necessarily acidic pH of basal insulin formulations, whose isoelectric point is comprised from 5.8 to 8.5, of insulin glargine type, may be a real problem, because this acidic pH of the insulin glargine formulation sometimes causes pain at injection in patients and, especially, prevents any formulation with other proteins, in particular, with prandial insulins, because the latter are not stable at acidic pH. The impossibility according to formulating a prandial insulin, at acidic pH, relates to the fact that prandial insulin undergoes, in these conditions, a secondary deamidation at position A21, which makes it impossible to meet the stability requirements applicable to injectable drugs.

At present, in applications WO 2013/021143 A1, WO 2013/104861 A1, WO 2014/124994 A1 and WO 2014/124993 A1, it was demonstrated that it was possible to solubilize these insulin glargine-type basal insulins, whose isoelectric point is comprised from 5.8 to 8.5, at neutral pH, while maintaining a difference in solubility between the in vitro medium (the container) and the in vivo medium (under the skin) regardless of the pH.

Application WO 2013/104861 A1 in particular describes compositions in the form of an injectable aqueous solution, whose pH is comprised from 6.0 to 8.0, comprising at least:
a) one basal insulin whose isoelectric point (pI) is comprised from 5.8 to 8.5, and b) a co-polyamino acid bearing carboxylate charges and hydrophobic radicals.

These compositions of the prior art have the major disadvantage of not being sufficiently stable to meet the specifications applicable to pharmaceutical formulations.

In the examples of the experimental portion of this patent application, it is demonstrated that the compositions described in particular in WO 2013/104861 A1 have unsatisfactory stability over time.

Therefore, there is a need to find a solution which allows to make a basal insulin soluble whose isoelectric point (pI) is comprised from 5.8 to 8.5, while preserving its basal profile after injection, but which also allows to satisfy the standard physical stability conditions for insulin-based pharmaceutical products.

Surprisingly, the applicant has found that the co-polyamino acids that carry carboxylate charges and hydrophobic radicals according to the invention make it possible to obtain compositions in the form of solutions which, not only meet the requirements described in WO 2013/104861 A1, but which also are able to provide improved physical stability to said compositions without having to increase the number of excipients used.

These performances, a priori never reached, are also maintained when the basal insulin whose isoelectric point is comprised from 5.8 to 8.5, is associated in the composition with a prandial insulin and/or a gastro-intestinal hormone.

Thus, surprisingly, the affinity of co-polyamino acids according to the invention for insulin glargine was increased in that it allows to obtain the solubilization and stabilization of insulin glargine solutions at a ratio [Hy]/[basal insulin] lower than that of the prior art; in addition, these results are obtained without altering, and are even improving, the propensity of insulin glargine to precipitate, as demonstrated in the experimental part.

This improvement in the affinity also makes it possible, in the context of chronic treatments, to limit the level of exposure to said excipients.

The co-polyamino acids bearing carboxylate charges and hydrophobic radicals Hy according to the invention have an excellent resistance to hydrolysis. This can be specifically verified under accelerated conditions, for example, at basic pH (pH 12) by hydrolysis tests.

In addition, forced oxidation tests, for example of the Fenton oxidation type, show that the co-polyamino acids bearing carboxylate charges and hydrophobic radicals Hy have a good resistance to oxidation.

Thus, the invention concerns physically stable compositions in the form of an injectable aqueous solution, whose pH is comprised from 6.0 to 8.0, comprising at least:
a) a basal insulin whose isoelectric point (pI) is comprised from 5.8 to 8.5, and
b) a co-polyamino-acid bearing carboxylate charges and at least one hydrophobic radical according to formula X.

In one embodiment, the invention concerns a composition in an aqueous injectable form, whose pH is comprised from 6.0 to 8.0, comprising at least:
a) a basal insulin whose isoelectric point pI is comprised from 5.8 to 8.5, and
b) A co-polyamino-acid bearing carboxylate charges and hydrophobic radicals-Hy, said co-polyamino-acid being constituted of glutamic or aspartic units and said hydrophobic radicals Hy according to the following formula X:

Formula X

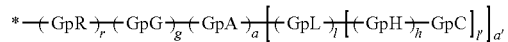

In which
GpR is chosen from the radicals according to formulas VII, VII' or VII":

Formula VII

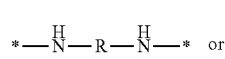 or

Formula VII′

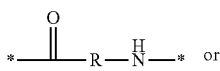 or

Formula VII″

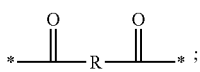;

Identical or different GpG and GpH are chosen from the radicals according to formula XI or XI′;

Formula XI

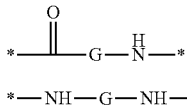

Formula XI′

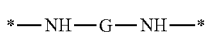

GpA is chosen from the radicals according to formula VIII

Formula VIII

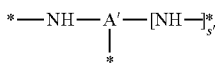

In which A′ is chosen from the radicals according to formula VIII′, VIII″ or VIII‴

Formula VIII′

Formula VIII″

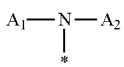

Formula VIII‴

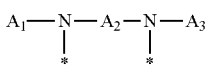

GpL is chosen from the radicals according to formula XII

Formula XII

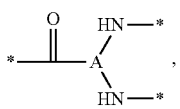,

GpC is a radical according to formula IX:

Formula IX

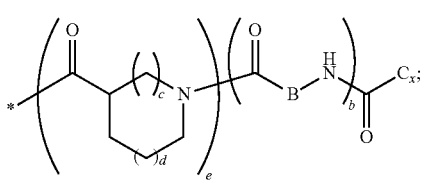

The * indicates the attachment sites of the different groups bonded by the amide functions;

a is an integer equal to 0 or to 1 and a′=1 if a=0 and a′=1, 2 or 3 if a=1;

a′ is an integer equal to 1, to 2, or to 3 b is an integer equal to 0 or to 1;

c is an integer equal to 0 or to 1, and if c is equal to 0, then d is equal to 1 or to 2;

d is an integer equal to 0, to 1, or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6;

l is an integer equal to 0 or 1 and l′=1 if l=0, and l′=2 if l=1;

r is an integer equal to 0, to 1, or to 2, and s′ is an integer equal to 0 or 1, and if e is different from 0, then at least one of g, h or l is different from 0; and if a=0, then l=0;

A, $A_1$, $A_2$ and $A_3$, identical or different, are linear or branched alkyl radicals, and optionally substituted by a radical derived from a saturated, unsaturated or aromatic ring, comprising from 1 to 8 carbon atoms.

B is a linear or branched alkyl radical, optionally comprising an aromatic nucleus, comprising from 1 to 9 carbon atoms or a unsubstituted ether or polyether radical comprising from 4 to 14 carbon atoms and from 1 to 5 oxygen atoms;

$C_x$ is a linear or branched monovalent alkyl radical, optionally comprising a ring part, in which x indicates the number of carbon atoms and:

When the hydrophobic radical -Hy carries 1-GpC, then $9 \leq x \leq 25$,

When the hydrophobic radical -Hy carries 2-GpC, then $9 \leq x \leq 15$,

When the hydrophobic radical -Hy carries 3-GpC, then $7 \leq x \leq 13$,

When the hydrophobic radical -Hy carries 4-GpC, then $7 \leq x \leq 11$,

When the hydrophobic radical -Hy carries 5-GpC, then $6 \leq x \leq 11$,

G is a branched alkyl radical of 1 to 8 carbon atoms, with said alkyl radical bearing one or more free carboxylic acid functions.

R is a radical chosen from the group consisting of a divalent alkyl radical, linear or branched, comprising 1 to 12 carbon atoms, a divalent alkyl radical, linear or branched, comprising 1 to 12 carbon atoms bearing one or more —$CONH_2$ functions, or a unsubstituted ether or polyether radical comprising from 4 to 14 carbon atoms and from 1 to 5 oxygen atoms:

the hydrophobic radical(s) -Hy according to formula X being bonded to the PLG:

via a covalent bond between a carbonyl of the hydrophobic radical -Hy and a nitrogen atom borne by the PLG, thus forming an amide function resulting from the reaction of an amine function borne by the PLG and an acid function borne by the precursor-Hy′ of the hydrophobic radical Hy, and via a covalent bond between a nitrogen atom of the hydrophobic radical -Hy and a carbonyl borne by the PLG, thus forming an amide function resulting from the reaction of an amine function of the precursor -Hy′ of the hydrophobic radical -Hy and an acid function borne by the PLG, the ratio M between the number of hydrophobic radicals and the number of glutamic or aspartic units being from $0 < M \leq 0.5$;

when several hydrophobic radicals are borne by a co-polyamino acid, they are then identical or different, the degree of polymerization DP in glutamic or aspartic units for PLG chains is comprised from 5 and 250;

the free carboxylic acid functions being in the form of an alkali metal salt chosen from the group consisting of $Na^+$ and $K^+$.

The invention also concerns a method for the preparation of stable, injectable compositions.

The pH of the compositions according to the invention is comprised from 6.0 to 8.0, and preferably from 6.6 to 7.8, or even more preferably, from 6.8 to 7.6.

Said co-polyamino acid bearing carboxylate charges and hydrophobic Hy radicals is soluble in an aqueous solution of pH from 6.0 to 8.0, at a temperature of 25° C. and at a concentration of less than 100 mg/ml.

Said co-polyamino acid bearing carboxylate charges and hydrophobic Hy radicals is soluble in an aqueous solution of pH from 6.0 to 8.0, at a temperature of 25° C. and at a concentration of less than 60 mg/ml.

The co-polyamino acid is a statistical co-polyamino acid in the chain of glutamic and/or aspartic units.

By "alkyl radical" is meant a carbon-comprising chain, linear or branched, which does not include a heteroatom.

In the formulas, the * indicates the attachment sites of the various elements represented.

By "physically stable composition" is meant compositions that meet the visual inspection criteria described in European, American and international pharmacopoeia, that is, compositions that are clear and that do not contain visible particles, but are also colorless.

By "injectable aqueous solution" is meant solutions for which the solvent is water and which meet the pharmacopoeia conditions of Europe and the US.

Compositions in the form of an injectable aqueous solution according to the invention are clear solutions. By "clear solution" is meant compositions that meet the criteria described in American and European pharmacopoeia regarding injectable solutions. In US pharmacopoeia, solutions are defined in part <1151>, referring to injection <1> (referring to <788> according to USP 35 and specified in <788> according to USP 35 and in <787>, <788> and <790> USP 38 (beginning on Aug. 1, 2014), according to USP 38). In European pharmacopoeia, injectable solutions must meet the criteria provided in sections 2.9.19 and 2.9.20.

By "co-polyamino acid being constituted of glutamic or aspartic units" is meant non-cyclic linear chains of glutamic or aspartic acid units bonded to each other by peptidic bonds, said chains presenting a C-terminal, corresponding to the carboxylic acid at one end, and an N-terminal part, corresponding to the amine at the other end of the chain.

By "soluble" is meant suitable to make possible the preparation of a clear solution, free of particles, at a concentration of less than 100 mg/ml in distilled water at 25° C.

The radicals Hy, GpR, GpG, GpH, GpA, GpL and GpC are each independently identical or different from one residue to another.

In one embodiment, the composition according to the invention is characterized in that the Hy comprises from 15 to 100 atoms of carbon.

In one embodiment, the composition according to the invention is characterized in that the Hy comprises from 30 to 70 atoms of carbon.

In one embodiment, the composition according to the invention is characterized in that the Hy comprises from 40 to 60 atoms of carbon.

In one embodiment, the composition according to the invention is characterized in that the Hy comprises from 20 to 30 atoms of carbon.

In one embodiment, the composition according to the invention is characterized in that the Hy comprises more than 30 atoms of carbon.

In the formulas, the * indicates the attachment sites of hydrophobic radicals to the PLG or between the different GpR, GpG, GpH, GpA, GpL and GpC to form amide functions.

Hy radicals are attached to the PLG via amide functions.

In one embodiment, r=0 and the hydrophobic radical according to formula X is bonded to the PLG via a covalent bond between a carbonyl of the hydrophobic radical and a nitrogen atom borne by the PLG, thus forming an amide function resulting from the reaction of an amine function borne by the PLG precursor and an acid function borne by the precursor Hy' of the hydrophobic radical.

In one embodiment, r=1 or 2 and the hydrophobic radical according to formula X is bonded to the PLG:

via a covalent bond between a nitrogen atom of the hydrophobic radical and a carbonyl borne by the PLG, thus forming an amide function resulting from the reaction of an amine function of the precursor -Hy' of the hydrophobic radical and an acid function borne by the PLG, via a covalent bond between a carbonyl of the hydrophobic radical and a nitrogen atom borne by the PLG, thus forming an amide function resulting from the reaction of an amine function of the precursor Hy' of the hydrophobic radical-Hy and an amine function of the PLG.

In one embodiment, if GpA is a radical according to formula VIIIc and r=1, then:

the GpC are directly or indirectly bonded to $N_{\alpha 1}$ and $N_{\alpha 2}$ and the PLG is directly or indirectly bonded via GpR to $N_{\beta 1}$, or the GpC are directly or indirectly bonded to $N_{\alpha 1}$ and $N_{\beta 1}$ and the PLG is directly or indirectly bonded via GpR to $N_{\alpha 2}$, or the GpC are directly or indirectly bonded to $N_{\alpha 2}$ and $N_{\beta 1}$ and the PLG is directly or indirectly bonded via GpR to $Na_{\alpha 1}$.

In one embodiment, if GpA is a radical according to formula VIIIc and r=0, then:

the GpC are directly or indirectly bonded to $N_{\alpha 1}$ and $N_{\alpha 2}$ and $N_{\alpha 2}$ and the PLG is directly or indirectly bonded to $N_{\beta 1}$; or the GpC are directly or indirectly bonded to $Na_{\alpha 1}$ and $N_{\beta 1}$ and the PLG is directly or indirectly bonded to $N_{\alpha 2}$; or the GpC are directly or indirectly bonded to $N_{\alpha 2}$ and $N_{\beta 1}$, and the PLG is directly or indirectly bonded to $N_{\alpha 1}$.

In one embodiment, if GpA is a radical according to formula VIIId and r=1, then the GpC are directly or indirectly bonded to $N_{\alpha 1}$, $N_{\alpha 2}$ and $N_{\beta 1}$ and the PLG is directly or indirectly bonded via GpR to $N_{\beta 2}$; or the GpC are directly or indirectly bonded to $N_{\alpha 1}$, $Na_{\beta 1}$ and $N_{\beta 2}$ and the PLG is directly or indirectly bonded via GpR to $N_{\beta 1}$; or the GpC are directly or indirectly bonded to $N_{\alpha 1}$, $N_{\beta 1}$ and $N_{\beta 2}$ and the PLG is directly or indirectly bonded via GpR to $N_{\alpha 2}$; or the GpC are directly or indirectly bonded to $N_{\alpha 2}$, $N_{\beta 1}$ and $N_{\beta 2}$ and the PLG is directly or indirectly bonded via GpR $N_{\alpha 1}$.

In one embodiment, if GpA is a radical according to formula VIIId and r=0, then
- the GpC are directly or indirectly bonded to $N_{\alpha 1}$, $N_{\alpha 2}$, and $N_{\beta 1}$ the PLG is directly or indirectly bonded to $N_{\beta 2}$; or
- the GpC are directly or indirectly bonded to $N_{\alpha 1}$, $N_{\alpha 2}$ and $N_{\beta 2}$ and $N_{\beta 2}$ and the PLG is directly or indirectly bonded to $N_{\beta 1}$; or
- the GpC are directly or indirectly bonded to $N_{\alpha 1}$, $N_{\beta 1}$ and $N_{\beta 2}$ and the PLG is directly or indirectly bonded to $N_{\alpha 2}$; or
- the GpC are directly or indirectly bonded to $N_{\alpha 2}$, $N_{\beta 1}$ and $N_{\beta 2}$ and the PLG is directly or indirectly bonded to $N_{\alpha 1}$.

In one embodiment, when r=2, then the GpR group bonded to the PLG is chosen from the GpR according to formula VII.

In one embodiment, when r=2, then the GpR group bonded to the PLG is chosen from the GpR according to formula VII and the second GpR is chosen from the GpR according to formula VII".

In one embodiment, an embodiment, when r=2 then the GpR bonded to the PLG is chosen from the GpR according to formula VII".

In one embodiment, an embodiment, when r=2, then the GpR group bonded to the PLG is chosen from the GpR according to formula VII" and the second GpR is chosen from the GpR according to formula VII.

In one embodiment, a=0,
In one embodiment, h=1 and g=0,
In one embodiment, h=0 and g=1,
In one embodiment, r=0, g=1 and h=0.
In one embodiment, at least one of g, h or l is different from 0.
In one embodiment, at least one of g and of h is equal to 1.
In one embodiment, at least one of g and h is equal to 1.
In one embodiment, a=1 and l=1.
In one embodiment, if l=0, at least one of g or h is equal to 0.
In one embodiment, if l=1, at least one of g or h is equal to 0.
In one embodiment, g+h≥2.
In one embodiment, g is greater than or equal to 2 (g≥2).
In one embodiment, h is greater than or equal to 2 (h≥2).
In one embodiment, g+h≥2 and a and 1 are equal to 0 (a=1=0).
In one embodiment, g+h≥2 and b is equal to 0 (b=0).
In one embodiment, g or h is greater than or equal to 2 (g≥2) and b is equal to 0.
In one embodiment, g+h≥2, b is equal to 0 (b=0) and e is equal to 1 (e=1).
In one embodiment, g or h is greater than or equal to 2 (g≥2) b is equal to 0 (b=0) and e is equal to 1 (e=1).

In one embodiment, said at least one hydrophobic radical -Hy is chosen from the radicals according to formula X in which r=2 according to formula Xc', as defined below:

Formula Xc'
$$*-GpR_1-GpR-(GpG)_g-(GpA)_a-[(GpL)_l-(GpH)_h-GpC]_r]_{a'}$$

in which $GpR_1$ is a radical according to formula VII.

Formula VII
$$*-\overset{H}{N}-R-\overset{H}{N}-*$$

in which GpR, GpG, GpA, GpL, GpH, GpC, R, a, a', g, h, l and l' have the definitions given above.

In one embodiment, said at least one hydrophobic radical -Hy is chosen from the radicals according to formula X in which r=2 according to formula Xc', as defined below:

Formula Xc'
$$*-GpR_1-GpR-(GpG)_g-(GpA)_a-[(GpL)_l-(GpH)_h-GpC]_r]_{a'}$$

in which GpR, is a radical according to formula VII".

Formula VII"
$$*-\overset{O}{\underset{\|}{C}}-R-\overset{O}{\underset{\|}{C}}-*$$

in which GpR, GpG, GpA, GpL, GpH, GpC, R, a, a', g, h, l and l' have the definitions given above.

In one embodiment, g=h=0, a=1, GpA is a radical according to according to formula VIII with s'=1 and A' according to formula VIII' or VIII", and l=1.

In one embodiment, said at least one hydrophobic radical -Hy is chosen from the radicals according to formula X in which r=2 according to formula Xc', as defined below:

Formula Xc'
$$*-GpR_1-GpR-(GpG)_g-(GpA)_a-[(GpL)_l-(GpH)_h-GpC]_r]_{a'}$$

in which GpR is a radical according to formula VII.

Formula VII
$$*-\overset{H}{N}-R-\overset{H}{N}-*$$

in which GpR, GpG, GpA, GpL, GpH, GpC, R, a, a', g, h, l and l' have the definitions given above.

In one embodiment, said at least one hydrophobic radical -Hy is chosen from the radicals according to formula X in which r=2 according to formula Xc', as defined below:

Formula Xc'
$$*-GpR_1-GpR-(GpG)_g-(GpA)_a-[(GpL)_l-(GpH)_h-GpC]_r]_{a'}$$

in which GpR, is a radical according to formula VII".

Formula VII"
$$*-\overset{O}{\underset{\|}{C}}-R-\overset{O}{\underset{\|}{C}}-*$$

in which GpR, GpG, GpA, GpL, GpH, GpC, R, a, a', g, h, l and l' have the definitions given above.

In one embodiment, said at least one hydrophobic radical -Hy is chosen from the radicals according to formula X in which
l=0,
according to formula Xb' as defined below.

Formula Xb'

in which
GpR is chosen from the radicals according to formulas VII, VII' or VII":

Formula VII

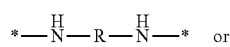 or

Formula VII'

 or

Formula VII"

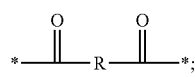;

GpG is chosen from the radicals according to formula XI XII':

Formula XI

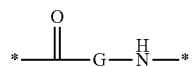

Formula XI'

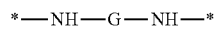

GpA is chosen from the radicals according to formula VIII in which s'=1 represented by formula VIIIa or formula VIII in which and s'=0 represented by formula VIIIb.

Formula VIIIa

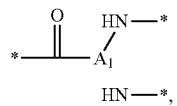

Formula VIIIb

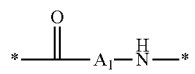

GpC is a radical according to formula IX:

Formula IX

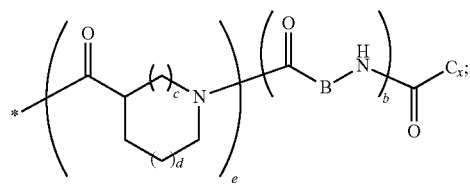

The * indicate the attachment sites of the different groups bonded by amide functions;

a is an integer equal to 0 or to 1 and a'=1 if a=0 and a'=1 or a'=2 if a=1;

a' is an integer equal to 1 or 2 and
If a' is equal to 1 then a is equal to 0 or to 1 and GpA is a radical according to formula VIIIb and,
if a' is equal to 2 then a is equal to 1 and GpA is a radical according to formula VIIIa;

b is an integer equal to 0 or to 1;

c is an integer equal to 0 or to 1, and if c is equal to 0, then d is equal to 1 or to 2;

d is an integer equal to 0, to 1, or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6, and at least one of g or h is different from 0;

r is an integer equal to 0, to 1, or to 2, and s' is an integer equal to 0 or 1;

$A_1$ is a linear or branched alkyl radical, and optionally substituted by a radical from a saturated, unsaturated or aromatic ring, comprising 1 to 6 carbon atoms.

B is a linear or branched alkyl radical optionally comprising an aromatic nucleus, comprising 1 to 9 carbon atoms or a unsubstituted ether or polyether radical comprising 4 to 14 carbon atoms and 1 to 5 oxygen atoms;

$C_x$ is a linear or branched monovalent alkyl radical, optionally comprising a cyclic part, in which x indicates the number of carbon atoms and:
When the hydrophobic radical -Hy carries 1-GpC, then $9 \leq x \leq 25$,
When the hydrophobic radical -Hy carries 2-GpC, then $9 \leq x \leq 15$,
When the hydrophobic radical -Hy carries 3-GpC, then $7 \leq x \leq 13$,
When the hydrophobic radical -Hy carries 4-GpC, then $7 \leq x \leq 11$,
When the hydrophobic radical -Hy carries at least 5-GpC, then $6 \leq x \leq 11$, G is a branched alkyl radical of 1 to 8 carbon atoms, with said alkyl radical bearing one or more free carboxylic acid functions, R is a radical chosen from the group consisting of a divalent alkyl radical, linear or branched, comprising 1 to 12 carbon atoms, a divalent alkyl radical, linear or branched, comprising 1 to 12 carbon atoms bearing one or more —$CONH_2$ functions, or a unsubstituted ether or polyether radical comprising from 4 to 14 carbon atoms and from 1 to 5 oxygen atoms:

The hydrophobic Hy radical(s) according to formula X being bonded to the PLG:
via a covalent bond between a carbonyl of the hydrophobic radical and a nitrogen atom borne by the PLG, thus forming an amide function resulting from the reaction of an amine function borne by the PLG and an acid function borne by the precursor of the hydrophobic radical, and
via a covalent bond between a nitrogen atom of the hydrophobic radical and a carbonyl borne by the PLG, thus forming an amide function resulting from the reaction of an amine function of the precursor -Hy' of the hydrophobic radical and an acid function borne by the PLG, the ratio M between the number of hydrophobic radicals and the number of glutamic or aspartic units being from $0 < M \leq 0.5$;

when several hydrophobic radicals are borne by a co-polyamino acid, then they are identical or different, free carboxylic acid functions being in the form of an alkali metal salt chosen from the group consisting of $Na^+$ and $K^+$.

In one embodiment, said at least one hydrophobic radical -Hy is chosen from the radicals according to formula X as defined below in which l=0, GpA is chosen from the radicals in formula VIII in which s'=1 and A' is chosen from the radicals according to formula VIII'' or VIII''', according to formula Xb' as defined below:

$$*-(\text{GpR})_r-(\text{GpG})_g-(\text{GpA})_a-[(\text{GpH})_h-\text{GpC}]_{a'} \quad \text{Formula Xb'}$$

in which

GpR is chosen from the radicals according to formulas VII, VII' or VII'':

$$*-\underset{H}{\overset{H}{N}}-R-\underset{H}{\overset{H}{N}}-* \quad \text{Formula VII}$$

or $$*-\underset{O}{\overset{\|}{C}}-R-\underset{H}{\overset{H}{N}}-* \quad \text{Formula VII'}$$

or $$*-\underset{O}{\overset{\|}{C}}-R-\underset{O}{\overset{\|}{C}}-*; \quad \text{Formula VII''}$$

GpG is chosen from the radicals according to formula XI or XI':

$$*-\underset{O}{\overset{\|}{C}}-G-\underset{H}{\overset{H}{N}}-* \quad \text{Formula XI}$$

$$*-NH-G-NH-* \quad \text{Formula XI'}$$

GpA is chosen from the radicals according to formulas VIIIc or VIIId:

Formula VIIIc $$*-N_{\beta 1}\begin{matrix}A_1-N_{\alpha 1}H-* \\ \\ A_2-N_{\alpha 2}H-*\end{matrix}$$

Formula VIIId $$*-N_{\beta 1}\begin{matrix}A_1-N_{\alpha 1}H-* \\ | \\ A_2 \\ | \\ -N_{\beta 2} \\ \\ A_3-N_{\alpha 2}H-*\end{matrix};$$

GpC is a radical according to formula IX:

Formula IX

The * indicate the attachment sites of the different groups bonded by the amide functions;

a is an integer equal to 0 or to 1 and a'=1 if a=0, and a'=2 or 3 if a=1;

a' is an integer equal to 2 or 3 and
 if a' is equal to 1 then a is equal to 0 and,
 if a' is equal to 2 or 3 then a is equal to 1 and GpA is a radical according to formula VIIIc or VIIId;

b is an integer equal to 0 or to 1;

c is an integer equal to 0 or to 1, and if c is equal to 0, then d is equal to 1 or to 2;

d is an integer equal to 0, to 1, or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6, and at least one of g or h is different from 0;

r is an integer equal to 0, to 1, or to 2, and s' is an integer equal to 1;

A, $A_2$, $A_3$ identical or different, are linear or branched alkyl radicals, and optionally substituted by a radical from a saturated, unsaturated or aromatic ring, comprising 1 to 6 carbon atoms.

B is a linear or branched alkyl radical optionally comprising an aromatic nucleus, comprising 1 to 9 carbon atoms or a unsubstituted ether or polyether radical comprising 4 to 14 carbon atoms and 1 to 5 oxygen atoms;

$C_x$ is a linear or branched monovalent alkyl radical, optionally comprising a cyclic part, in which x indicates the number of carbon atoms and:
 When the hydrophobic radical -Hy carries 1-GpC, then $9 \leq x \leq 25$,
 When the hydrophobic radical -Hy carries 2-GpC, then $9 \leq x \leq 15$,
 When the hydrophobic radical -Hy carries 3-GpC, then $7 \leq x \leq 13$,
 When the hydrophobic radical -Hy carries 4-GpC, then $7 \leq x \leq 11$,
 When the hydrophobic radical -Hy carries 5-GpC, then $6 \leq x \leq 11$, The hydrophobic Hy radical(s) according to formula X being bonded to the PLG:

via a covalent bond between a carbonyl of the hydrophobic radical and a nitrogen atom borne by the PLG, thus forming an amide function resulting from the reaction of an amine function borne by the PLG and an acid function borne by the precursor -Hy' of the hydrophobic radical, and via a covalent bond between a nitrogen atom of the hydrophobic radical and a carbonyl borne by the PLG. Thus forming an amide function resulting from the reaction of an amine function of the precursor -Hy' of the hydrophobic radical and an acid function borne by the PLG, G is a branched alkyl radical of 1 to 8 carbon atoms, with said alkyl radical bearing one or more free carboxylic acid functions, R is a radical chosen from the group consisting of a divalent alkyl radical, linear or branched, comprising 1 to 12 carbon atoms, a divalent alkyl radical, linear or branched, comprising 1 to 12 carbon atoms bearing one or more —$CONH_2$ functions, or a unsubstituted ether or polyether radical comprising from 4 to 14 carbon atoms and 1 to 5 oxygen atoms:

the ratio M between the number of hydrophobic radicals and the number of glutamic or aspartic units being from $0<M\leq0.5$;

when several hydrophobic radicals are borne by a co-polyamino acid, then they are identical or different, free carboxylic acid functions being in the form of an alkali metal salt chosen from the group consisting of $Na^+$ and $K^+$.

In one embodiment, said at least one hydrophobic radical -Hy is chosen from the radicals according to formula X in which a=1 and a'=1 according to formula Xa, as defined below:

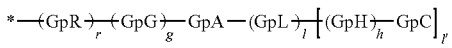

Formula Xa in which GpA is a radical according to formula VIII and A' is chosen from the radicals according to formula VIII' with s'=0 and GpA is a radical according to formula VIIIb

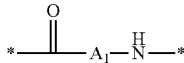

Formula VIIIb

And GpR, GpG, GpL, GpL, GpC, $A_1$, r, g, h, l and l' have the definitions given above.

In one embodiment, said at least one hydrophobic radical -Hy is chosen from the radicals according to formula X in which a=1 according to formula Xb, as defined below:

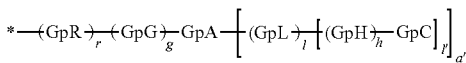

Formula Xb in which GpA is a radical according to formula VIII and A' is chosen from the radicals according to formula VIII' with s'=1 and GpA is a radical according to formula VIIIa

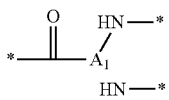

Formula VIIIa

And GpR, GpG, GpL, GpH, GpC, $A_1$, a', r, g, h, l and l' have the definitions given above.

In one embodiment, said at least one hydrophobic radical -Hy is chosen from the radicals according to formula X in which a=1, as defined below:

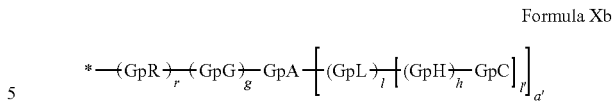

Formula Xb

In which GpA is a radical according to formula VIII and A is chosen from the radicals of
Formula VIII' with s'=1 and GpA is a radical according to formula VIIIc

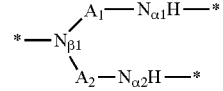

Formula VIIIc

And GpR, GpG, GpL, GpH, GpC, $A_1$, $A_2$, r, g, h, a', l and l' have the definitions given above.

In one embodiment, said at least one hydrophobic radical -Hy is chosen from the radicals according to formula X in which a=1, as defined below:

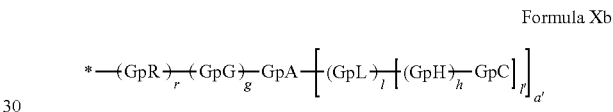

Formula Xb in which GpA is a radical according to formula VIII and A is chosen from the radicals according to formula VIII''' with s'=1, and GpA is a radical according to formula VIIId.

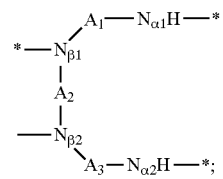

Formula VIIId

And GpR, GpG, GpL, GpH, GpC, $A_1$, $A_2$, $A_3$, a', r, g, h, l and l' have the definitions given above.

In one embodiment, the composition according to the invention is characterized in that said hydrophobic radicals are chosen from the hydrophobic radicals according to formula X in which GpA is a radical according to formula VIIIb, a'=1 and l=0, represented by the following formula Xe:

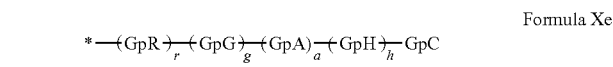

Formula Xe

GpR, GpG, GpA, GpH, GpC, r, g, h, and a have the definitions given above.

In one embodiment, r=-0, and GpA is chosen from the radicals according to formulas VIIIa and VIIIb.

In one embodiment, r=-0, and GpA is chosen from the radicals according to formula VIIIa and VIIIb.

In one embodiment, r=-0, and GpA is chosen from the radicals according to formulas VIIIa and VIIIb and h=0.

In one embodiment, said at least one hydrophobic radical -Hy is chosen from the radicals according to formula X in which r=1 according to formula Xc, as defined below:

Formula Xc

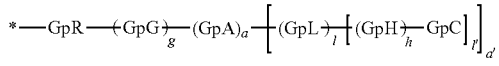

in which GpR is a radical according to formula VII.

Formula VII

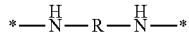

And GpG, GpA, GpL, GpH, GpC, R, a, a', g, h, l, a' and l' have the definitions given above.

In one embodiment, said at least one hydrophobic radical -Hy is chosen from the radicals according to formula X in which r=1 according to formula Xc, as defined below:

Formula Xc

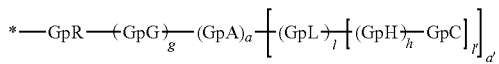

in which GpR is a radical according to formula VII'.

Formula VII'

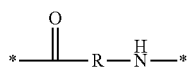

And GpG, GpA, GpL, GpH, GpC, R, a, a', g, h, l, a' and l' have the definitions given above.

In one embodiment, said at least one hydrophobic radical -Hy is chosen from the radicals according to formula X in which r=1 according to formula Xc, as defined below:

Formula Xc

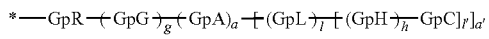

in which GpR is a radical according to formula VII".

Formula VII"

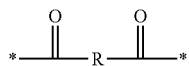

In one embodiment, r=1, and GpR is chosen from the radicals according to formulas VII' and VII" and h=0.

In one embodiment, r=1, g=0 and GpR is a radical according to formula VII' and h=0.

In one embodiment, r=1, g=0 and GpR is a radical according to formula VII' and h=1.

In one embodiment, r=1, g=0 and GpR is a radical according to formula VII', GpA is chosen from the radicals according to formula VIIIa or VIIIb and h=0.

In one embodiment, r=1, g=0, GpR is a radical according to formula VII', GpA is a radical according to formula VIIIa or VIIIb and h=1.

In one embodiment, r=1, g=0 GpR is a radical according to formula VII', GpA is a radical according to formula VIIIa and h=0.

In one embodiment, r=1, g=0 GpR is a radical according to formula VII', GpA is a radical according to formula VIIIa and h=1.

In one embodiment, r=1, g=0, GpR is a radical according to formula VII', GpA is a radical according to formula VIIIb and h=0.

In one embodiment, r=1, g=0, GpR is a radical according to formula VII', GpA is a radical according to formula VIIIb and h=1.

In one embodiment, said at least one hydrophobic radical -Hy is chosen from the radicals according to formula X, as defined below:

Formula X

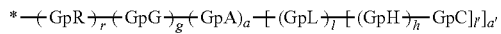

in which GpC is a radical according to formula IX in which e=0 and GpC is a radical according to formula IXa.

Formula IXa

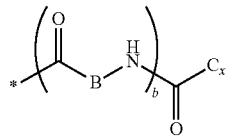

In one embodiment, said at least one hydrophobic radical -Hy is chosen from the radicals according to formula X, as defined below:

Formula X

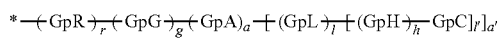

in which GpC is a radical according to formula IX in which e=1, b=0 and GpC is a radical according to formula IXd.

Formula IXd

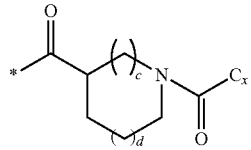

In one embodiment, said at least one hydrophobic radical -Hy is chosen from the radicals according to formula X, as defined below:

Formula X

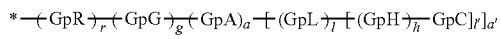

in which GpC is a radical according to formula IX in which e=1 and GpC is a radical according to formula IXb Formula IXb

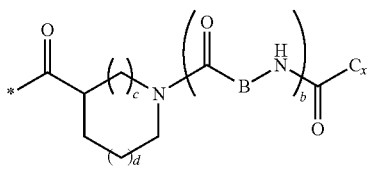

In one embodiment, said at least one hydrophobic radical -Hy is chosen from the radicals according to formula X in which r, g, a, l, h are equal to 0 according to formula Xd, as defined below:

\*-GpC     Formula Xd, in which GpC is a radical according to formula IX in which e=0, b=0 and GpC is a radical according to formula IXc.

 IXc

In one embodiment, the composition according to the invention is characterized in that said hydrophobic radicals are chosen from the hydrophobic radicals according to formula X in which a'=2 and a=1 and l=0, represented by the following formula Xf:

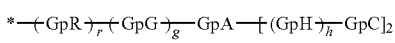 Formula Xf

GpR, GpG, GpA, GpH, GpC, r, g and h have the definitions given above.

In one embodiment, the composition according to the invention is characterized in that said hydrophobic radicals are chosen from the hydrophobic radicals according to formula X in which h=0, l=0 and l'=1, represented by the following formula Xg:

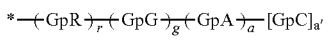 Formula Xg

GpR, GpG, GpA, GpC, r, g, a, and a' have the definitions given above.

In one embodiment, the composition according to the invention is characterized in that said hydrophobic radicals are chosen from the hydrophobic radicals according to formula X in which h=0, a'=1 represented by the following formula Xh:

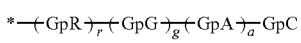 Formula Xh

GpR, GpG, GpA, GpC, r, a and g have the definitions given above.

In one embodiment, the composition according to the invention is characterized in that said hydrophobic radicals are chosen from the hydrophobic radicals according to formula X in which h=0, a'=2 and a=1, represented by the following formula Xi:

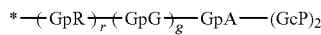 Formula Xi

GpR, GpG, GpA, GpC, r and g have the definitions given above.

In one embodiment, the composition is characterized in that the hydrophobic radical according to formulas X, Xa, Xb, Xb', Xc, Xe, Xf, Xg, Xh and Xi is a radical in which R is a divalent linear alkyl radical comprising from 2 to 12 atoms of carbon.

In one embodiment, the composition is characterized in that the hydrophobic radical according to formulas X, Xa, Xb, Xb', Xc, Xe, Xf, Xg, Xh and Xi is a radical in which R is a divalent linear alkyl radical comprising from 2 to 6 atoms of carbon.

In one embodiment, the composition is characterized in that the hydrophobic radical according to formulas X, Xa, Xb, Xb', Xc, Xe, Xf, Xg, Xh and Xi is a radical in which R is a divalent linear alkyl radical comprising from 2 to 6 atoms of carbon.

In one embodiment, the composition is characterized in that the hydrophobic radical according to formulas X, Xa, Xb, Xb', Xc, Xe, Xf, Xg, Xh and Xi is a radical in which R is a divalent linear alkyl radical comprising from 2 to 4 atoms of carbon.

In one embodiment, the composition is characterized in that the hydrophobic radical according to formulas X, Xa, Xb, Xb', Xc, Xe, Xf, Xg, Xh and Xi is a radical in which R is a divalent, linear alkyl radical comprising from 2 to 4 atoms of carbon.

In one embodiment, the composition is characterized in that the hydrophobic radical according to formulas X, Xa, Xb, Xb', Xc, Xe, Xf, Xg, Xh and Xi is a radical in which R is a divalent alkyl radical comprising from 2 atoms of carbon.

In one embodiment, the composition is characterized in that the hydrophobic radical according to formulas X, Xa, Xb, Xb', Xc, Xe, Xf, Xg, Xh and Xi is a radical in which R is a divalent, linear alkyl radical comprising from 1 to 11 atoms of carbon.

In one embodiment, the composition is characterized in that the hydrophobic radical according to formulas X, Xa, Xb, Xb', Xc, Xe, Xf, Xg, Xh and Xi is a radical in which R is a divalent, linear alkyl radical comprising from 1 to 6 atoms of carbon.

In one embodiment, the composition is characterized in that the hydrophobic radical according to formulas X, Xa, Xb, Xb', Xc, Xe, Xf, Xg, Xh and Xi is a radical in which R is a divalent alkyl radical comprising from 2 to 5 atoms of carbon and bearing one or more amide functions (—$CONH_2$).

In one embodiment, the composition is characterized in that the hydrophobic radical according to formulas X, Xa, Xb, Xb', Xc, Xe, Xf, Xg, Xh and Xi is a radical in which R is a divalent, linear alkyl radical comprising 2 to 5 atoms of carbon and bearing one or more amide functions (—$CONH_2$).

In one embodiment, the composition is characterized in that the hydrophobic radical according to formulas X, Xa, Xb, Xb', Xc, Xe, Xf, Xg, Xh and Xi is a radical in which R is a radical chosen from the group consisting of the radicals represented by the formulas below:

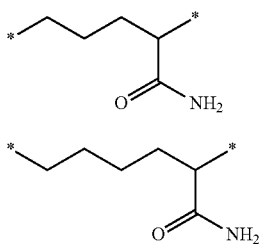

Formula X1

Formula X2

In one embodiment, the composition is characterized in that the hydrophobic radical according to formulas X, Xa, Xb, Xb', Xc, Xe, Xf, Xg, Xh and Xi is a radical in which R is a radical according to formula X1.

In one embodiment, the composition is characterized in that the hydrophobic radical according to formulas X, Xa, Xb, Xb', Xc, Xe, Xf, Xg, Xh and Xi is a radical in which R is a radical according to formula X2.

In one embodiment, the composition is characterized in that the hydrophobic radical according to formulas X, Xa, Xb, Xb', Xc, Xe, Xf, Xg, Xh and Xi is a radical in which R is bonded to the co-polyamino acid via an amide function borne by the carbon in delta or epsilon position (or in position 4 or 5) in relation to the amide function (—CONH$_2$).

In one embodiment, the composition is characterized in that the hydrophobic radical according to formulas X, Xa, Xb, Xb', Xc, Xe, Xf, Xg, Xh and Xi is a radical in which R is an unsubstituted linear ether or polyether radical comprising 4 to 14 carbon atoms and from 1 to 5 oxygen atoms.

In one embodiment, the composition is characterized in that the hydrophobic radical according to formulas X, Xa, Xb, Xb', Xc, Xe, Xf, Xg, Xh and Xi is a radical in which R is an ether radical.

In one embodiment, the composition is characterized in that the hydrophobic radical according to formulas X, Xa, Xb, Xb', Xc, Xe, Xf, Xg, Xh and Xi is a radical in which R is an ether radical comprising 4 to 6 carbon atoms.

In one embodiment, the composition is characterized in that the hydrophobic radical according to formulas X, Xa, Xb, Xb', Xc, Xe, Xf, Xg, Xh and Xi is a radical in which R is a divalent alkyl radical comprising 6 atoms of carbon.

In one embodiment, the composition is characterized in that the hydrophobic radical according to formulas X, Xa, Xb, Xb', Xc, Xe, Xf, Xg, Xh and Xi is a radical in which R is an ether radical represented by formula,

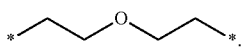

In one embodiment, the composition is characterized in that the hydrophobic radical according to formulas X, Xa, Xb, Xb', Xc, Xe, Xf, Xg, Xh and Xi is a radical in which R is a polyether radical.

In one embodiment, the composition is characterized in that the hydrophobic radical according to formulas X, Xa, Xb, Xb', Xc, Xe, Xf, Xg, Xh and Xi is a radical in which R is a linear polyether or polyether radical comprising from 6 to 10 carbon atoms and from 2 to 3 oxygen atoms.

In one embodiment, the composition is characterized in that the hydrophobic radical according to formulas X, Xa, Xb, Xb', Xc, Xe, Xf, Xg, Xh and Xi is a radical in which R is a polyether radical chosen from the group consisting of the radicals represented by the formulas below:

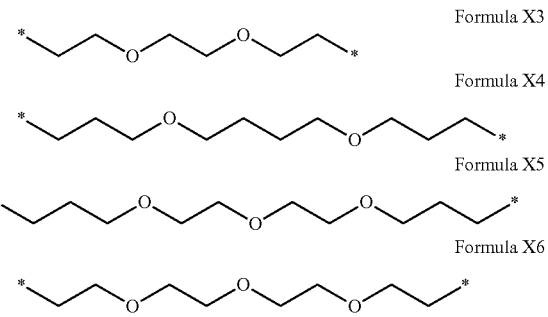

Formula X3

Formula X4

Formula X5

Formula X6

In one embodiment, the composition is characterized in that the hydrophobic radical according to formulas X, Xa, Xb, Xb', Xc, Xe, Xf, Xg, Xh and Xi is a radical in which R is a radical according to formula X3.

In one embodiment, the composition is characterized in that the hydrophobic radical according to formulas X, Xa, Xb, Xb', Xc, Xe, Xf, Xg, Xh and Xi is a radical in which R is a radical according to formula X4.

In one embodiment, the composition is characterized in that the hydrophobic radical according to formulas X, Xa, Xb, Xb', Xc, Xe, Xf, Xg, Xh and Xi is a radical in which R is a polyether radical chosen from the group consisting of the radicals represented by the formulas X5 and X6 below:

In one embodiment, the composition is characterized in that the hydrophobic radical according to formulas X, Xa, Xb, Xb', Xc, Xe, Xf, Xg, Xh and Xi is a radical in which R is a polyether radical according to formula X5.

In one embodiment, the composition is characterized in that the hydrophobic radical according to formulas X, Xa, Xb, Xb', Xc, Xe, Xf, Xg, Xh and Xi is a radical in which R is a polyether radical according to formula X6.

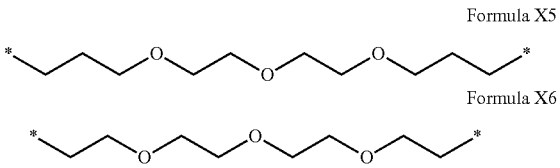

Formula X5

Formula X6

In one embodiment, the composition is characterized in that the hydrophobic radical according to formulas X, Xa, Xb, Xb', Xc, Xe, Xf, Xg, Xh and Xi is a radical in which the radical GpG and/or GpH is according to formula XI' in which G is an alkyl radical comprising 6 carbon atoms represented by formula Z below:

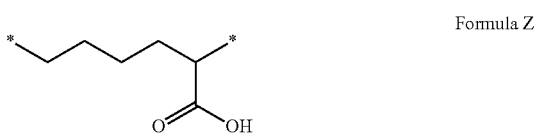 [SMILES: *CCCCC(*)C(=O)O]

Formula Z

In one embodiment, the composition is characterized in that the hydrophobic radical according to formulas X, Xa, Xb, Xb', Xc, Xe, Xf, Xg, Xh and Xi is a radical in which the radical GpG and/or GpH is according to formula XI in which G is an alkyl radical comprising 4 carbon atoms represented by formula Z below:

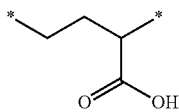
Formula Z'

In one embodiment, the composition is characterized in that the hydrophobic radical according to formulas X, Xa, Xb, Xb', Xc, Xe, Xf, Xg, Xh and Xi is a radical in which the radical GpG and/or GpH is according to formula XI in which G is an alkyl radical comprising 4 carbon atoms represented by —(CH$_2$)$_2$—CH(COOH)—.

In one embodiment, the composition is characterized in that the hydrophobic radical according to formulas X, Xa, Xb, Xb', Xc, Xe, Xf, Xg, Xh and Xi is a radical in which the radical GpG and/or GpH is according to formula XI in which G is an alkyl radical comprising 4 carbon atoms represented by —CH((CH$_2$)$_2$COOH)—.

In one embodiment, the composition is characterized in that the hydrophobic radical according to formulas X, Xa, Xb, Xb', Xc, Xe, Xf, Xg, Xh and Xi is a radical in which the radical GpG and/or GpH is according to formula XI in which G is an alkyl radical comprising 3 carbon atoms represented by —CH$_2$—CH—(COOH).

In one embodiment, the composition is characterized in that the hydrophobic radical according to formulas X, Xa, Xb, Xb', Xc, Xe, Xf, Xg, Xh and Xi is a radical in which the radical GpG and/or GpH is according to formula XI in which G is an alkyl radical comprising 3 carbon atoms represented —CH(CH$_2$)COOH)—.

In one embodiment, the composition is characterized in that the hydrophobic radical according to formulas X, Xa, Xb, Xb', Xc, Xe, Xf, Xg, Xh and Xi is a radical in which GpA is according to formula VIII and in which A$_1$, A$_2$ or A$_3$ is chosen from the group consisting of the radicals represented by the formulas below:

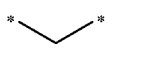
Formula Y1

Formula Y2

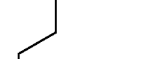
Formula Y3

Formula Y4

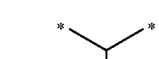
Formula Y5

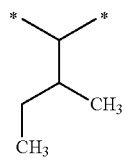
Formula Y6

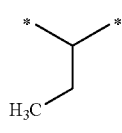
Formula Y7

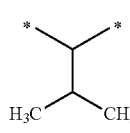
Formula Y8

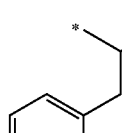
Formula Y9

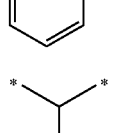
Formula Y10

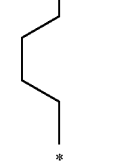

In one embodiment, the composition is characterized in that the hydrophobic radical according to formulas X, Xa, Xb, Xb', Xc, Xd, Xe, Xf, Xg, Xh and Xi is a radical in which the radical GpC according to formula IX is chosen from the group consisting of the radicals according to formulas IXe, IXf or IXg represented below:

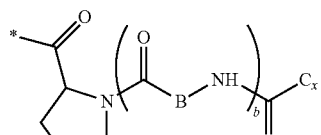
Formula IXe

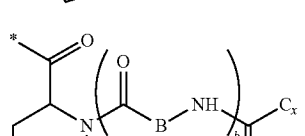
Formula IXf

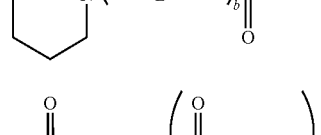
Formula IXg

In one embodiment, the composition is characterized in that the hydrophobic radical according to formulas X, Xa, Xb, Xb', Xd, Xc, Xd, Xe, Xf, Xg, Xh and Xi is a radical in which the radical GpC according to formula IX is chosen from the group consisting of the radicals according to formulas IXe, IXf or IXg in which b is equal to 0, respectively responding to formulas IXh, IXi, and IXj below:

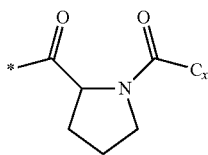

Formula IXh

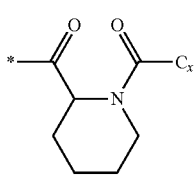

Formula IXi

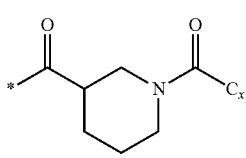

Formula IXj

In one embodiment, the composition is characterized in that the hydrophobic radical according to formulas X, Xa, Xb, Xb', Xc, Xd, Xe, Xf, Xg, Xh and Xi is a radical in which the radical GpC responds to the formula IX or IXe in which b=0, and responds to the formula IXh.

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of the linear alkyl radicals.

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of branched alkyl radicals.

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of alkyl radicals comprising from 19 to 14 carbon atoms.

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of the radicals represented by the formulas below:

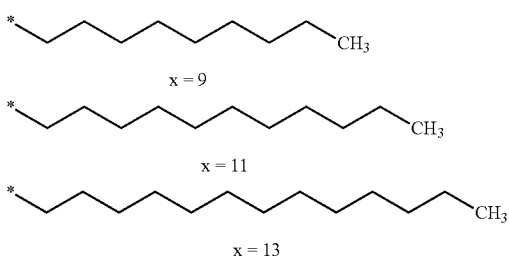

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of alkyl radicals comprising from 15 to 16 carbon atoms.

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of the radicals represented by the formulas below:

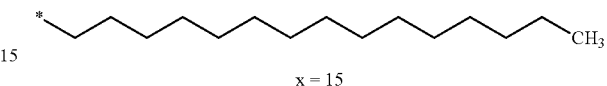

x = 15

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of the radicals represented by the formulas below:

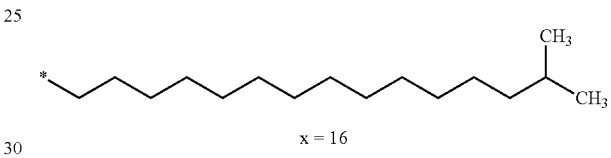

x = 16

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of alkyl radicals comprising from 17 to 25 carbon atoms.

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of alkyl radicals comprising from 17 to 18 carbon atoms.

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of the alkyl radicals represented by the formulas below:

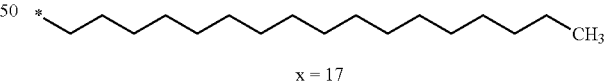

x = 17

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of alkyl radicals comprising from 18 to 25 carbon atoms.

In one embodiment, the composition is characterized in that the hydrophobic radical according to formulas X, Xa, Xb, Xb', Xc, Xd, Xe, Xf, Xg, Xh and Xi is a radical in which Cx is chosen from the group consisting of the alkyl radicals represented by the formulas below:

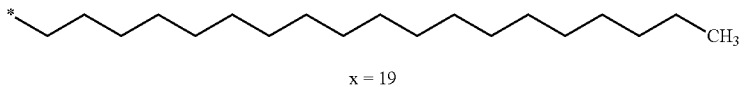

x = 19

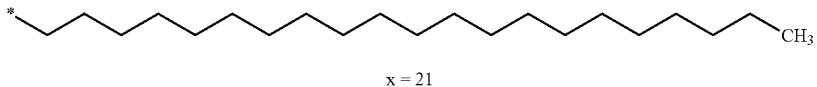

x = 21

In one embodiment, the composition is characterized in that the hydrophobic radical according to formulas X, Xa, Xb, Xb', Xc, Xd, Xe, Xf, Xg, Xh and Xi is a radical in which in which the radical GpC according to formula IX is chosen from the group constituted of radicals in which Cx is chosen from the group consisting of alkyl radicals comprising from 14 to 15 carbon atoms.

In one embodiment, the composition is characterized in that the hydrophobic radical according to formulas X, Xa, Xb, Xb', Xc, Xd, Xe, Xf, Xg, Xh and Xi is a radical in which the radical GpC according to formula IX is chosen from the group constituted of radicals in which Cx is chosen from the group consisting of the radicals represented by the formulas below:

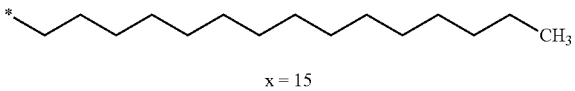 [SMILES: *CCCCCCCCCCCCCCC]

x = 15

In one embodiment, when a'=1, x is comprised from 11 to 25 ($11 \leq x \leq 25$). In particular, when x is comprised from 15 to 16 (x=15 or 16) then r=1 and R is an ether or polyether radical and when x is greater than 17 ($x \geq 17$) then r=1 and R is an ether or polyether radical.

In one embodiment, when a'=2, x is comprised from 9 to 15 ($9 \leq x \leq 15$).

In one embodiment, the co-polyamino acid is chosen from the co-polyamino acids according to formula XXXb in which the hydrophobic radical -Hy is chosen from the group of hydrophobic radicals according to formulas X, Xc', Xa, Xb', Xc, Xe, Xg and Xh in which a'=1 and l'=1 and GpC is a radical according to formula IXe.

In one embodiment, the co-polyamino acid is chosen from the co-polyamino acids according to formula XXXb in which the hydrophobic radical -Hy is chosen from the group of hydrophobic radicals according to formulas X, Xc', Xa, Xb', Xc, Xe, Xg and Xh in which a'=1 and l'=1 and GpC is a radical according to formula IX in which e=0.

In one embodiment, the co-polyamino acid is chosen from the co-polyamino acids according to formula XXXb in which the hydrophobic radical -Hy is chosen from the group of hydrophobic radicals according to formulas X, Xc', Xa, Xb', Xc, Xf, Xg and Xi in which a'=2 or l'=2 and GpC is a radical according to formula IXe.

In one embodiment, the co-polyamino acid is chosen from the co-polyamino acids according to formula XXXb in which the hydrophobic radical -Hy is chosen from the group of hydrophobic radicals according to formulas X, Xc', Xa, Xb', Xc, Xf, Xg and Xi in which a'=2 and l'=2 and GpC is a radical according to formula IX in which e=0.

In one embodiment, the co-polyamino acid is chosen from the co-polyamino acids according to formula XXXa in which the hydrophobic radical -Hy is chosen from the group of hydrophobic radicals according to formulas X, Xc', Xa, Xb', Xc, Xe, Xg and Xh in which a'=1 and l'=1 and GpC is a radical according to formula IXe.

In one embodiment, the co-polyamino acid is chosen from the co-polyamino acids according to formula XXXa in which the hydrophobic radical -Hy is chosen from the group of hydrophobic radicals according to formulas X, Xc', Xa, Xb, Xc, Xf, Xg and Xi in which a'=2 and l'=2 and GpC is a radical according to formula IXe.

In one embodiment, the hydrophobic radical Hy is chosen from the group of hydrophobic radicals according to formula X, in which h is greater than or equal to 2 and GpC is according to formula Ixe.

In one embodiment, the hydrophobic radical Hy is chosen from the group of hydrophobics according to formula X in which g is greater than or equal to 2 and a, 1 and h are equal to 0 and GpC is according to formula Ixe.

In one embodiment, the composition is characterized in that the hydrophobic radical from the hydrophobic radicals according to formulas X, Xc', Xa, Xb, Xb', Xc, Xe, Xg and Xh in which a'=1 and l'=1 and in which Cx is chosen from the group consisting of the linear alkyl radicals.

In one embodiment, the composition is characterized in that the hydrophobic radical is chosen from the hydrophobic radicals according to formulas X, Xc', Xa, Xb, Xb', Xc, Xf, Xg and Xi in which a'=2 or l'=2 and in which Cx is chosen from the group consisting of the linear alkyl radicals.

In one embodiment, the hydrophobic radical -Hy is chosen from the group of hydrophobic radicals according to formula X in which GpR is a radical according to formula VII, GpH is a radical from XI and GpC is according to formula IX in which e=1, b=0 and x=13.

In one embodiment, the co-polyamino acid is a poly-L-sodium glutamate modified at one of its extremities according to the formula represented below, described in example B1.

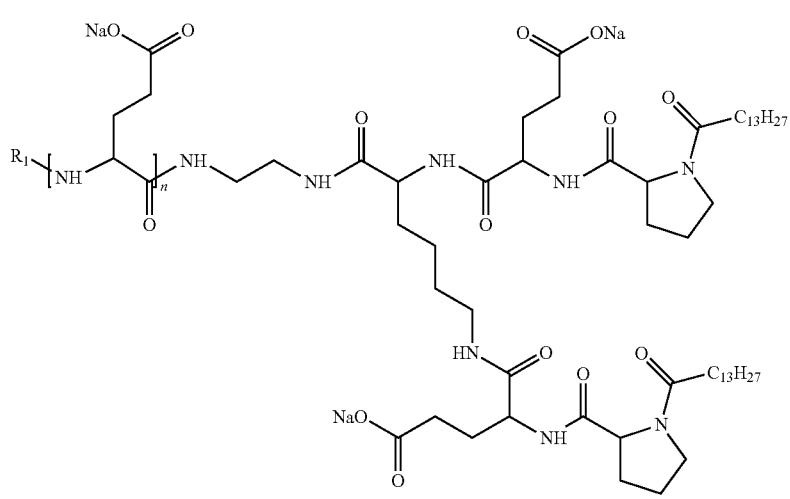

B1 i = 0.038, DP = 26
R₁ = H or pyroglutamate

In one embodiment, the co-polyamino acid is a poly-L-sodium glutamate modified at one of its extremities according to the formula represented below, described in example B18.

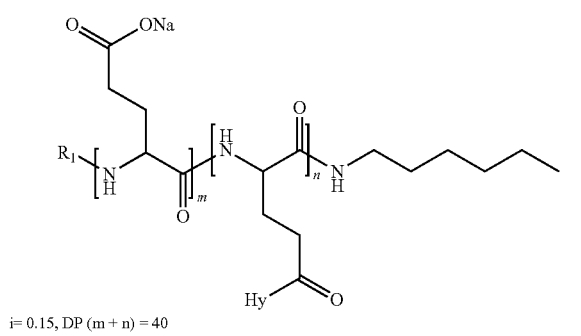

i = 0.15, DP (m + n) = 40

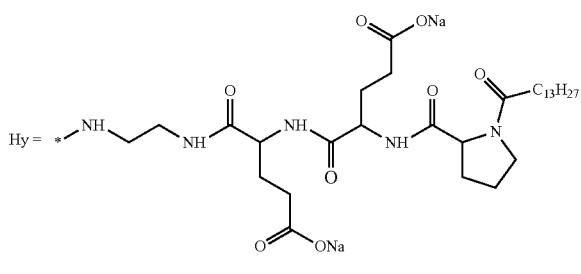

R₁ = H or pyroglutamate

In one embodiment, the composition according to the invention is characterized in that the ratio M between the number of hydrophobic radicals and the number of glutamate or aspartic units is comprised from 0.007 to 0.3.

In one embodiment, the composition according to the invention is characterized in that the ratio M between the number of hydrophobic radicals and the number of glutamate or aspartic units is comprised from 0.01 to 0.3.

In one embodiment, the composition according to the invention is characterized in that the ratio M between the number of hydrophobic radicals and the number of glutamate or aspartic units is comprised from 0.02 to 0.2.

In one embodiment, the composition according to the invention is characterized in that the hydrophobic radical responds to formula X and the ratio M between the number of hydrophobic radicals and the number of glutamate or aspartic units is comprised from 0.007 to 0.15.

In one embodiment, the composition according to the invention is characterized in that the hydrophobic radical responds to formula X and the ratio M between the number of hydrophobic radicals and the number of glutamate or aspartic units is comprised from 0.01 to 0.1.

In one embodiment, the composition according to the invention is characterized in that the hydrophobic radical responds to formula X and the ratio M between the number of hydrophobic radicals and the number of glutamate or aspartic units is comprised from 0.02 to 0.08.

In one embodiment, the composition according to the invention is characterized in that the hydrophobic radical responds to formula X in which radical Cx comprises from 9 to 10 atoms and the ratio M between the number of hydrophobic radicals and the number of glutamate or aspartic units is comprised from 0.03 to 0.15.

In one embodiment, the composition according to the invention is characterized in that the hydrophobic radical responds to formula X in which radical Cx comprises from 11 to 12 atoms and the ratio M between the number of hydrophobic radicals and the number of glutamate or aspartic units is comprised from 0.015 to 0.1.

In one embodiment, the composition according to the invention is characterized in that the hydrophobic radical responds to formula X in which radical Cx comprises from 11 to 12 atoms and the ratio M between the number of hydrophobic radicals and the number of glutamate or aspartic units is comprised from 0.02 to 0.08.

In one embodiment, the composition according to the invention is characterized in that the hydrophobic radical responds to formula X in which radical Cx comprises from 13 to 15 atoms and the ratio M between the number of hydrophobic radicals and the number of glutamate or aspartic units is comprised from 0.01 to 0.1.

In one embodiment, the composition according to the invention is characterized in that the hydrophobic radical responds to formula X in which radical Cx comprises from 13 to 15 atoms and the ratio M between the number of hydrophobic radicals and the number of glutamate or aspartic units is comprised from 0.01 to 0.06.

In one embodiment, the composition according to the invention is characterized in that the hydrophobic radical responds to formula X and the ratio M between the number of hydrophobic radicals and the number of glutamate or aspartic units is comprised from 0.007 to 0.3.

In one embodiment, the composition according to the invention is characterized in that the hydrophobic radical responds to formula X and the ratio M between the number of hydrophobic radicals and the number of glutamate or aspartic units is comprised from 0.01 to 0.3.

In one embodiment, the composition according to the invention is characterized in that the hydrophobic radical responds to formula X and the ratio M between the number of hydrophobic radicals and the number of glutamate or aspartic units is comprised from 0.015 to 0.2.

In one embodiment, the composition according to the invention is characterized in that the hydrophobic radical responds to formula X in which radical Cx comprises from 11 to 14 atoms and the ratio M between the number of hydrophobic radicals and the number of glutamate or aspartic units is comprised from 0.1 to 0.2.

In one embodiment, the composition according to the invention is characterized in that the hydrophobic radical responds to formula X in which radical Cx comprises from 15 to 16 atoms and the ratio M between the number of hydrophobic radicals and the number of glutamate or aspartic units is comprised from 0.04 to 0.15.

In one embodiment, the composition according to the invention is characterized in that the hydrophobic radical responds to formula X in which radical Cx comprises between 17 and 18 atoms and the ratio M between the number of hydrophobic radicals and the number of glutamate or aspartic units is comprised from 0.02 to 0.06.

In one embodiment, the composition according to the invention is characterized in that the hydrophobic radical responds to formula X in which radical Cx comprises from 19 to 25 atoms and the ratio M between the number of hydrophobic radicals and the number of glutamate or aspartic units is comprised from 0.01 to 0.06.

In one embodiment, the composition according to the invention is characterized in that the hydrophobic radical responds to formula X in which radical Cx comprises between 19 and 25 carbon atoms and the ratio M between the number of hydrophobic radicals and the number of glutamate or aspartic units is comprised from 0.01 to 0.05.

In one embodiment, the composition according to the invention is characterized in that the co-polyamino acid bearing carboxylate charges and hydrophobic radicals is chosen from the co-polyaminoacids according to formula XXXa' below:

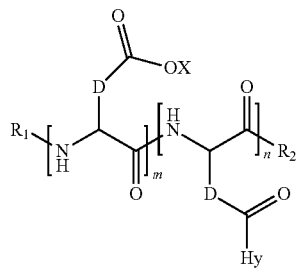

formula XXXa' in which

D represents, independently, either a —CH$_2$— group (aspartic unit) or a —CH$_2$—CH$_2$— group (glutamic unit), Hy is a hydrophobic radical chosen from the hydrophobic radicals according to formula X, in which r=1 and GpR is a radical according to formula VII, R$_1$ is a hydrophobic radical chosen from the hydrophobic radicals according to formula X in which r=-0 or r=1 and GpR is a radical according to formula VII', or a radical chosen from the group consisting of an H, a linear acyl group in C2 to C10, a branched acyl group in C4 to C10, a benzyl, a terminal "amino acid" unit and a pyroglutamate, R$_2$ is a hydrophobic radical chosen from the hydrophobic radicals according to formula X in which r=1 and GpR is a radical according to formula VII, or a radical —NR'R", with R' and R", either identical or different, being chosen from the group comprised by H, the linear or branched or cyclic alkyls in C2 to C10, the benzyl and said alkyls R' and R" which may form together one or more saturated, unsaturated and/or aromatic carbonated cycles, and/or may comprise hetero-atoms, chosen from the group comprised of O, N and S;

X represents a cationic entity chosen from the group comprising alkaline cations;

n+m represents the degree of polymerization DP of the co-polyamino acid, namely, the average number of monomeric units per co-polyamino acid chain and 5≤n+m≤250.

When the co-polyamino-acid comprises one or more aspartic unit(s), the latter may be subject to structural rearrangements.

In one embodiment, the composition according to the invention is characterized in that when the co-polyamino acid comprises aspartic units, then the co-polyamino acid may also comprise monomeric units according to formula XXXI and/or XXXI'.

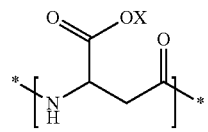

Formula XXXI

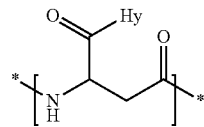

Formula XXXI'

We call "a statistically grafted co-polyamino-acid" a co-polyamino acid bearing carboxylate charges and at least one hydrophobic radical, a co-polyamino acid according to formula XXXa.

In one embodiment, the composition according to the invention is characterized in that the co-polyamino acid bearing carboxylate charges and hydrophobic radicals is chosen from the co-polyamino acids according to formula XXXa', in which R$_1$=R'$_1$ and R$_2$=R'$_2$, according to formula XXXa below:

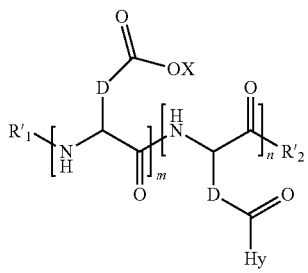

formula XXXa

In which m, n, X, D and Hy have the definitions given above,

R'$_1$ is a radical chosen from the group consisting of an H, a linear acyl group in C2 to C10, a branched acyl group in C4 to C10, a benzyl, a terminal "amino acid" unit and a pyroglutamate, R$_2$ is a —NR'R" radical, R' and R", either identical or different, being chosen from the group comprised by H, the linear or branched or cyclic alkyls in C2 to C10, the benzyl and said R' and R" alkyls optionally forming together one or more carbonated, saturated, unsaturated and/or aromatic cycles, optionally comprising heteroatoms, chosen from the group comprised of O, N and S;

In one embodiment, the composition according to the invention is characterized in that the co-polyamino acid bearing carboxylate charges and hydrophobic radicals is chosen from the co-polyamino acids according to formula XXXa in which Hy is a radical according to formula X.

In one embodiment, the composition according to the invention is characterized in that the co-polyamino acid bearing carboxylate charges and hydrophobic radicals is chosen from the co-polyamino acids according to formula XXXa in which Hy is a radical according to formula X, in which r=1.

In one embodiment, the composition according to the invention is characterized in that the co-polyamino acid bearing carboxylate charges and hydrophobic radicals is chosen from the co-polyamino acids according to formula XXXa, in which Hy is a radical according to formula X, in which r=1, and for GpC, b=0.

In one embodiment, the composition according to the invention is characterized in that the co-polyamino acid bearing carboxylate charges and hydrophobic radicals is chosen from the co-polyamino acids according to formula XXXa in which Hy is a radical according to formula X and in which GpC is a radical according to formula IX.

In one embodiment, the composition according to the invention is characterized in that the co-polyamino acid bearing carboxylate charges and hydrophobic radicals is chosen from the co-polyamino acids according to formula XXXa in which Hy is a radical according to formula X and in which GpC is a radical according to formula IX and r=1.

We call "a defined grafted co-polyamino-acid" a co-polyamino acid bearing carboxylate charges and at least one hydrophobic radical, a co-polyamino acid according to formula XXXb.

In one embodiment, the composition according to the invention is characterized in that the co-polyamino acid bearing carboxylate charges and hydrophobic radicals is chosen from the co-polyamino acids according to formula XXXa', in which n=0 according to the following formula XXXb:

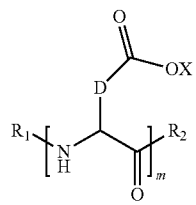

formula XXXb in which m, X, D, R$_1$ and R$_2$ have the definitions given above and at least R$_1$ or R$_2$ is a radical hydrophobic according to formula X.

In one embodiment, the composition according to the invention is characterized in that the co-polyamino acid bearing carboxylate charges and hydrophobic radicals is chosen from the co-polyamino acids according to formula XXXa' in which n=0 according to formula XXXb and R$_1$ or R$_2$ is a radical hydrophobic according to formula X.

In one embodiment, the composition according to the invention is characterized in that the co-polyamino acid bearing carboxylate charges and hydrophobic radicals is chosen from the co-polyamino acids according to formula XXXb in which R1=R'1 according to formula XXXb':

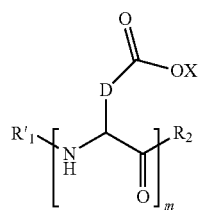

formula XXXb' in which m, X, D, R'$_1$ and R$_2$ have the definitions given above and R$_2$ is a hydrophobic radical according to formula X.

In one embodiment, the composition according to the invention is characterized in that the co-polyamino acid bearing carboxylate charges and hydrophobic radicals is chosen from the co-polyamino acids according to formula XXXb in which R2=R'2 according to formula XXXb":

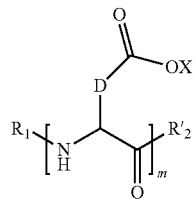

formula XXXb"

in which m, X, D, R$_1$ and R'$_2$ have the definitions given above and R$_1$ is a hydrophobic radical according to formula X.

In one embodiment, the composition according to the invention is characterized in that the co-polyamino acid bearing carboxylate charges and hydrophobic radicals is chosen from the co-polyamino acids according to formula XXXb or XXXb" in which R$_1$ is a radical according to formula X and in which GpR is according to formula VII'.

In one embodiment, the composition according to the invention is characterized in that the co-polyamino acid bearing carboxylate charges and hydrophobic radicals is chosen from the co-polyamino acids according to formula XXXb or XXXb" in which $R_1$ is a radical according to formula X and in which GpR is according to formula VII".

In one embodiment, the composition according to the invention is characterized in that the co-polyamino acid bearing carboxylate charges and hydrophobic radicals is chosen from the co-polyamino acids according to formula XXXb or XXXb" in which $R_1$ is a hydrophobic radical according to formula X and GpR is according to formula VII' and GpC is according to formula IX.

In one embodiment, the composition according to the invention is characterized in that the co-polyamino acid bearing carboxylate charges and hydrophobic radicals is chosen from the co-polyamino acids according to formula XXXb or XXXb" in which $R_1$ is a hydrophobic radical according to formula X and GpR is according to formula VII' and GpC is according to formula IX.

In one embodiment, the composition according to the invention is characterized in that the co-polyamino acid bearing carboxylate charges and hydrophobic radicals is chosen from the co-polyamino acids according to formula XXXb or XXXb' in which $R_2$ is a hydrophobic radical according to formula X and in which r=1 and GpR is according to formula VII.

In one embodiment, the composition is characterized in that the co-polyamino acid bearing carboxylate charges and hydrophobic radicals is chosen from the co-polyamino acids according to formula XXXa' in which at least one of $R_1$ or $R_2$ is a hydrophobic radical as defined above, according to the following formula XXX:

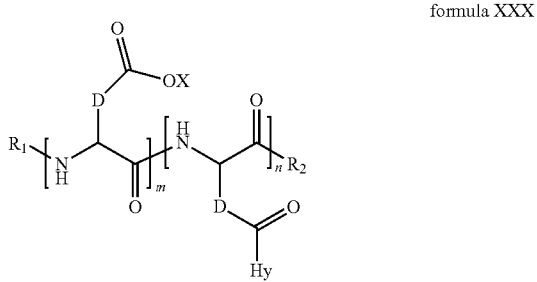

formula XXX in which
- D represents, independently, either a —$CH_2$— group (aspartic unit) or a —$CH_2$—$CH_2$— group (glutamic unit),
- Hy is a hydrophobic radical chosen from the hydrophobic radicals according to formulas X, in which r=1 and GpR is a radical according to formula VII,
- $R_1$ is a hydrophobic radical chosen from the hydrophobic radicals according to formulas X in which r=0 or r=1 and GpR is a radical according to formula VII', or a radical chosen from the group consisting of an H, a linear acyl group in C2 to C10, a branched acyl group in C4 to C10, a benzyl, a terminal "amino acid" unit and a pyroglutamate,
- $R_2$ is a hydrophobic radical chosen from the hydrophobic radicals according to formula X in which r=1 and GpR is a radical according to formula VII, or a —NR'R" radical, with R' and R", either identical or different, being chosen from the group comprised by H, the linear or branched or cyclic alkyls in C2 to C10, the benzyl and said R' and R" alkyls optionally forming together one or more carbonated, saturated, unsaturated and/or aromatic cycles, optionally comprising heteroatoms, chosen from the group comprised of O, N and S,
- at least one of $R_1$ or $R_2$ is a hydrophobic radical as defined above,
- X represents an H or a cationic entity chosen from the group comprising the metallic cations;
- n+m represents the degree of polymerization DP of the co-polyamino acid, namely, the average number of monomeric units per co-polyamino acid chain and 5≤n+m≤250.

In one embodiment, the composition according to the invention is characterized in that the co-polyamino acid bearing carboxylate charges and hydrophobic radicals is chosen from the co-polyamino acids according to formulas XXX, XXXa, XXXa', XXXb, XXXb' or XXXb" in which group D is a —$CH_2$— group (aspartic unit).

In one embodiment, the composition according to the invention is characterized in that the co-polyamino acid bearing carboxylate charges and hydrophobic radicals is chosen from the co-polyamino acids according to formulas XXX, XXXa, XXXa', XXXb, XXXb' or XXXb" in which group D is a —$CH_2$—$CH_2$— group (glutamic unit).

In one embodiment, the composition according to the invention is characterized in that $R_1$ is a radical chosen from the group comprised by a linear acyl group in $C_2$ to $C_{10}$, a branched acyl group in $C_4$ to $C_{10}$, a benzyl, a terminal "amino acid" unit and a polyglutamate.

In one embodiment, the composition according to the invention is characterized in that $R_1$ is a radical chosen from the group comprised by a linear acyl group in $C_2$ to $C_{10}$, or a branched acyl group in $C_4$ to $C_{10}$.

In one embodiment, the composition according to the invention is characterized in that the co-polyamino acid bearing carboxylate charges and hydrophobic radicals is chosen from the co-polyamino acids according to formulas XXXa, XXXb, XXXb' or XXXb" in which group D is a —$CH_2$— group (aspartic unit).

In one embodiment, the composition according to the invention is characterized in that the co-polyamino acid bearing carboxylate charges and hydrophobic radicals is chosen from the co-polyamino acids according to formulas XXXa, XXXb, XXXb' or XXXb" in which the co-polyamino acid is chosen from the co-polyamino acids in which group D is a —$CH_2$—$CH_2$— group (glutamic unit).

In one embodiment, the composition according to the invention is characterized in that n+m is comprised from 10 to 200.

In one embodiment, the composition according to the invention is characterized in that n+m is comprised from 15 to 150.

In one embodiment, the composition according to the invention is characterized in that n+m is comprised from 15 to 100.

In one embodiment, the composition according to the invention is characterized in that n+m is comprised from 15 to 80.

In one embodiment, the composition according to the invention is characterized in that n+m is comprised from 15 to 65.

In one embodiment, the composition according to the invention is characterized in that n+m is comprised from 20 to 60.

In one embodiment, the composition according to the invention is characterized in that n+m is comprised from 20 to 50.

In one embodiment, the composition according to the invention is characterized in that n+m is comprised from 20 to 40.

The invention also concerns a co-polyamino acid bearing carboxylate charges and hydrophobic radicals-Hy, said co-polyamino acid being constituted of glutamic or aspartic units and said hydrophobic radicals Hy being chosen from the radicals according to formula X as defined below:

Formula X

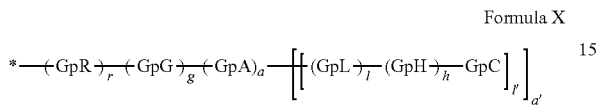

in which
GpR is chosen from the radicals according to formulas VII, VII' or VII":

Formula VII

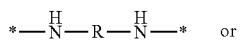    or

Formula VII'

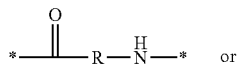    or

Formula VII"

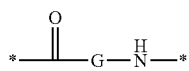;

Identical or different GpG and GpH are chosen from the radicals according to formulas XI or XI';

Formula XI

Formula XI'

*—NH—G—NH—*

GpA is chosen from the radicals according to formula VIII

Formula VIII

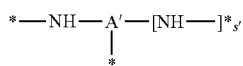

In which A' is chosen from the radicals according to formula VIII', VIII" or VIII'''

Formula VIII'

Formula VIII"

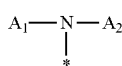

Formula VIII'''

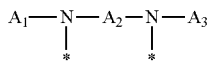

GpL is chosen from the radicals according to formula XII

Formula XII

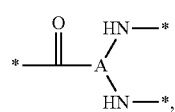

GpC is a radical according to formula IX:

Formula IX

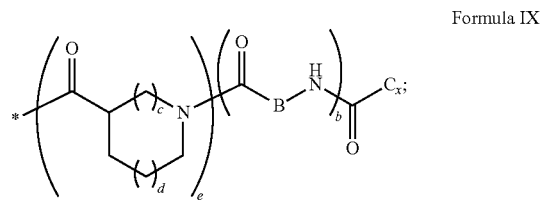

The * indicate the attachment sites of the different groups bonded by the amide functions;

a is an integer equal to 0 or to 1 and a'=1 if a=0, and a'=1, 2 or 3 if a=1;

a' is an integer equal to 1, to 2, or to 3;

b is an integer equal to 0 or to 1;

c is an integer equal to 0 or to 1, and if c is equal to 0, then d is equal to 1 or to 2;

d is an integer equal to 0, to 1, or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6, and at least one of g, h or l is different from 0;

l is an integer equal to 0 or 1 and l'=1 if l=0, and l'=2 if l=1;

r is integer equal to 0, to 1, or to 2, and s' is an integer equal to 0 or 1;

and if e is different from 0, then at least one of g, h or l is different from 0;

and if a=0, then l=0;

A, $A_1$, $A_2$ and $A_3$, identical or different, are linear or branched alkyl radicals comprising from 1 to 8 carbon atoms, and optionally substituted by a radical from a saturated, unsaturated or aromatic cycle;

B is an unsubstituted ether or polyether comprising 4 to 14 carbon atoms and from 1 to 5 oxygen atoms or a linear or branched alkyl radical, optionally including an aromatic nucleus, comprising 1 to 9 carbon atoms.

$C_x$ is a linear or branched monovalent alkyl radical, optionally comprising a cyclic part, in which x indicates the number of carbon atoms and:

When the hydrophobic radical -Hy carries 1-GpC, then $9 \leq x \leq 25$,

When the hydrophobic radical -Hy carries 2-GpC, then $9 \leq x \leq 15$,

When the hydrophobic radical -Hy carries 3-GpC, then $7 \leq x \leq 13$,

When the hydrophobic radical -Hy carries 4-GpC, then $7 \leq x \leq 11$,

When the hydrophobic radical -Hy carries at least 5-GpC, then $6 \leq x \leq 11$, G is a linear or branched alkyl radical of 1 to 8 carbon atoms, said alkyl radical bearing one or more free carboxylic acid function(s), R is a radical chosen from the group consisting of a divalent, linear or branched alkyl radical comprising 1 to 12 carbon atoms, a divalent linear or branched alkyl radical comprising 1 to 12 carbon atoms bearing one or more —$CONH_2$ functions, or an unsubstituted ether or polyether radical comprising from 4 to 14 carbon atoms and from 1 to 5 oxygen atoms, The hydrophobic radical(s) -Hy according to formula X being bonded to the PLG:

via a covalent bond between a carbonyl of the hydrophobic radical -Hy and a nitrogen atom borne by the PLG, thus forming an amide function resulting from the reaction of an amine function borne by the PLG and an acid function borne by the precursor -Hy' of the hydrophobic radical -Hy, and via a covalent bond between a nitrogen atom of the hydrophobic radical -Hy and a carbonyl borne by the PLG, thus forming an amide function resulting from the reaction of an amine function of the precursor -Hy' of the hydrophobic radical -Hy and an acid function borne by the PLG, the ratio M between the number of hydrophobic radicals and the number of glutamic or aspartic units being between 0<M≤0.5;

when several hydrophobic radicals are borne by a co-polyamino acid, then they are identical or different, the degree of polymerization DP in glutamic or aspartic units for PLG chains is between 5 and 250;

free carboxylic acid functions being in the form of an alkali metal salt chosen from the group consisting of $Na^+$ and $K^+$.

The invention also concerns the precursor Hy' of the hydrophobic radical -Hy according to formula X' as defined below:

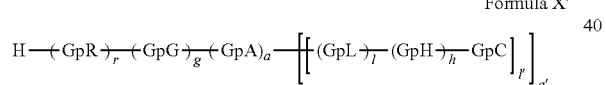

Formula X' in which

GpR is chosen from the radicals according to formulas VII, VII' or VII":

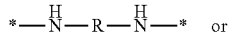

Formula VII

Formula VII'

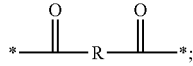

Formula VII"

Identical or different GpG and GpH are chosen from the radicals according to formulas XI or XI';

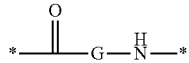

Formula XI

Formula XI'

GpA is chosen from the radicals according to formula VIII

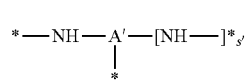

Formula VIII

In which A' is chosen from the radicals according to formula VIII', VIII" or VIII'"

Formula VIII'

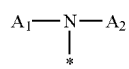

Formula VIII"

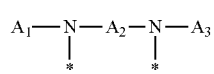

Formula VIII'"

GpL is chosen from the radicals according to formula XII

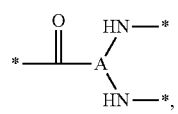

Formula XII

GpC is a radical according to formula IX:

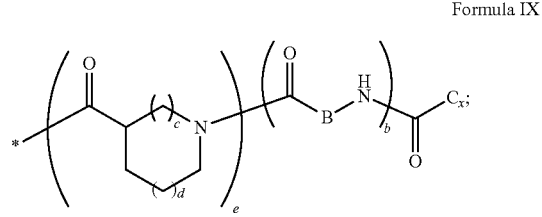

Formula IX

The * indicate the attachment sites of the different groups bonded by the amide functions;

a is an integer equal to 0 or to 1 and a'=1 if a=0 and a'=1, 2 or 3 if a=1;

a' is an integer equal to 1, to 2, or to 3;

b is an integer equal to 0 or to 1;

c is an integer equal to 0 or to 1, and if c is equal to 0, then d is equal to 1 or to 2;

d is an integer equal to 0, to 1, or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6, and at least one of g, h or l is different from 0;

l is an integer equal to 0 or 1 and l'=1 if l=0, and l'=2 if l=1;

r is integer equal to 0, to 1, or to 2, and s' is an integer equal to 0 or 1;

and if e is different from 0, then at least one of g, h or l is different from 0;

and if a=0, then l=0;

A, $A_1$, $A_2$ and $A_3$, identical or different, are linear or branched alkyl radicals comprising from 1 to 8 carbon atoms, and optionally substituted by a radical from a saturated, unsaturated or aromatic cycle;

B is an unsubstituted ether or polyether radical comprising from 4 to 14 carbon atoms and from 1 to 5 oxygen atoms or a linear or branched alkyl radical, optionally including an aromatic nucleus, comprising from 1 to 9 carbon atoms.

Cx is a linear or branched monovalent alkyl radical, optionally comprising a cyclic part, in which x indicates the number of carbon atoms and:

When the hydrophobic radical -Hy bears 1-GpC, then $9 \leq x \leq 25$,

When the hydrophobic radical -Hy bears 2-GpC, then $9 \leq x \leq 15$,

When the hydrophobic radical -Hy bears 3-GpC, then $7 \leq x \leq 13$,

When the hydrophobic radical -Hy bears 4-GpC, then $7 \leq x \leq 11$,

When the hydrophobic radical -Hy bears at least 5-GpC, then $6 \leq x \leq 11$,

G is a divalent linear or branched alkyl radical of 1 to 8 carbon atoms, said alkyl radical bearing one or more free carboxylic acid function(s), R is a radical chosen from the group consisting of a divalent linear or branched alkyl radical comprising 1 to 12 carbon atoms, a divalent linear or branched alkyl radical comprising 1 to 12 carbon atoms bearing one or more —$CONH_2$ function(s), or an unsubstituted ether or polyether radical comprising from 4 to 14 carbon atoms and from 1 to 5 oxygen atoms, the hydrophobic radical(s) -Hy according to formula X being bonded to the PLG:

via a covalent bond between a carbonyl of the hydrophobic radical -Hy and a nitrogen atom borne by the PLG, thus forming an amide function resulting from the reaction of an amine function borne by the PLG and an acid function borne by the precursor -Hy' of the hydrophobic radical -Hy, and via a covalent bond between a nitrogen atom of the hydrophobic radical -Hy and a carbonyl borne by the PLG, thus forming an amide function resulting from the reaction of an amine function of the precursor -Hy' of the hydrophobic radical -Hy and an acid function borne by the PLG, the ratio M between the number of hydrophobic radicals and the number of glutamic or aspartic units being between $0 < M \leq 0.5$;

when several hydrophobic radicals are borne by a co-polyamino acid, they are then identical or different, free carboxylic acid functions being in the form of an alkali metal salt chosen from the group consisting of $Na^+$ and $K^+$.

In one embodiment, the composition according to the invention is characterized in that the co-polyamino acid is derived from a polyamino acid obtained by polymerization.

In one embodiment, the composition according to the invention is characterized in that the co-polyamino acid is derived from a polyamino acid obtained by ring-opening polymerization of a derivative of N-carboxyanhydride glutamic acid or of a derivative of N-carboxyanhydride aspartic acid.

In one embodiment, the composition according to the invention is characterized in that the co-polyamino acid is derived from a polyamino acid obtained by polymerization of a derivative of N-carboxyanhydride glutamic acid or of a derivative of N-carboxyanhydride aspartic acid, as described in the article from the journal Adv. Polym. Sci. 2006, 202, 1-18 (Deming, T. J.).

In one embodiment, the composition according to the invention is characterized in that the co-polyamino acid is derived from a polyamino acid obtained by polymerization of a derivative of glutamic acid N-carboxyanhydride.

In one embodiment, the composition according to the invention is characterized in that the co-polyamino acid is derived from a polyamino acid obtained by polymerization of a derivative of glutamic acid N-carboxyanhydride chosen from the group consisting of polymethyl glutamate N-carboxyanhydride (GluOMe-NCA), polybenzyl glutamate N-carboxyanhydride (GluOBzl-NCA) and poly-t-butyl glutamate N-carboxy anhydride (GluOtBu-NCA).

In one embodiment, the glutamic acid N-carboxyanhydride derivative is poly-L methyl glutamate N-carboxyanhydride (L-GluOMe-NCA).

In one embodiment, the glutamic acid N-carboxyanhydride derivative is poly-L benzyl glutamate N-carboxyanhydride (L-GluOBzl-NCA).

In one embodiment, the composition according to the invention is characterized in that the co-polyamino acid is derived from a polyamino acid obtained by polymerization of a derivative of glutamic acid N-carboxyanhydride or of a derivative of aspartic acid N-carboxyanhydride by using an organometallic compound of a transition metal as initiator, as described in the publication Nature 1997, 390, 386-389 (Deming, T. J.).

In one embodiment, the composition according to the invention is characterized in that the co-polyamino acid is derived from a polyamino acid obtained by polymerization of a derivative of glutamic acid N-carboxyanhydride or of a derivative of aspartic acid N-carboxyanhydride by using ammonia or a primary amine as initiator, as described in French patent FR 2,801,226 (Touraud, F., et al.) and the references cited by this patent.

In one embodiment, the composition according to the invention is characterized in that the co-polyamino acid is derived from a polyamino acid obtained by polymerization of a derivative of glutamic acid N-carboxyanhydride or of a derivative of aspartic acid N-carboxyanhydride by using hexamethyldisilazane as initiator, as described in the publication J. Am. Chem. Soc. 2007, 129, 14114-14115 (Lu H.; et al.) or a silylated amine, as described in the publication J. Am. Chem. Soc. 2008, 130, 12562-12563 (Lu H.; et al.).

In one embodiment, the composition according to the invention is characterized in that the process for synthesizing the polyamino acid obtained by polymerization of a derivative of glutamic acid N-carboxyanhydride or of a derivative of aspartic acid N-carboxyanhydride from which the co polyamino acid is derived, comprises a step of ester functions hydrolysis.

In one embodiment, this hydrolysis step of the ester groups may consist of hydrolysis in an acidic medium or hydrolysis in a base medium or be conducted by hydrogenation.

In one embodiment, this ester groups hydrolysis step is a hydrolysis in an acidic medium.

In one embodiment, this ester groups hydrolysis step is conducted by hydrogenation.

In one embodiment, the composition according to the invention is characterized in that the co-polyamino acid is derived from a polyamino acid obtained by depolymerization of a polyamino acid of a higher molecular weight.

In one embodiment, the composition according to the invention is characterized in that the co-polyamino acid is derived from a polyamino acid obtained by enzymatic depolymerization of a polyamino acid of a higher molecular weight.

In one embodiment, the composition according to the invention is characterized in that the co-polyamino acid is derived from a polyamino acid obtained by chemical depolymerization of a polyamino acid of a higher molecular weight.

In one embodiment, the composition according to the invention is characterized in that the co-polyamino acid is derived from a polyamino acid obtained by enzymatic and chemical depolymerization of a polyamino acid of a higher molecular weight.

In one embodiment, the composition according to the invention is characterized in that the co-polyamino acid is derived from a polyamino acid obtained by depolymerization of a polyamino acid of a higher molecular weight chosen from the group consisting of sodium polyglutamate and sodium polyaspartate.

In one embodiment, the composition according to the invention is characterized in that the co-polyamino acid is derived from a polyamino acid obtained by depolymerization of a sodium polyglutamate of a higher molecular weight.

In one embodiment, the composition according to the invention is characterized in that the co-polyamino acid is derived from a polyamino acid obtained by depolymerization of a sodium polyaspartate of a higher molecular weight.

In one embodiment, the composition according to the invention is characterized in that the co-polyamino acid is obtained by grafting a hydrophobic group onto a poly-L-glutamic acid or a poly-L-aspartic acid by using the amide bond formation process well-known to the person versed in the art.

In one embodiment, the composition according to the invention is characterized in that the co-polyamino acid is obtained by grafting a hydrophobic group onto a poly-L-glutamic acid or a poly-L-aspartic acid by using the amide bond formation processes used for peptide synthesis.

In one embodiment, the composition according to the invention is characterized in that the co-polyamino acid is obtained by grafting a hydrophobic group onto a poly-L-glutamic acid or a poly-L-aspartic acid, as described in French patent FR 2,840,614 (Chan, Y. P.; et al.).

Subsequently, the units used for insulins are those recommended by the pharmacopoeias, their mg/ml equivalences being given in the table below:

| Insulin | EP Pharmacopoeia 8.0 (2014) | US Pharmacopoeia - USP38 (2015) |
|---|---|---|
| Aspart | 1U = 0.0350 mg of insulin aspart | 1 USP = 0.0350 mg of insulin aspart |
| Lispro | 1U = 0.0347 mg of insulin lispro | 1 USP = 0.0347 mg of insulin lispro |
| Human | IUI = 0.0347 mg of human insulin | 1 USP = 0.0347 mg of human insulin |
| Glargine | 1U = 0.0364 mg of insulin glargine | 1 USP = 0.0364 mg of insulin glargine |
| Porcine | IUI = 0.0345 mg of porcine insulin | 1 USP = 0.0345 mg of porcine insulin |
| Bovine | IUI = 0.0342 mg of bovine insulin | 1 USP = 0.0342 mg of bovine insulin |

By basal insulin with an isoelectric point from 5.8 to 8.5 is meant an insoluble insulin at pH 7 and whose duration of action is comprised from 8 to 24 hours or longer in standard diabetes models.

These basal insulins, whose isoelectric point is comprised from 5.8 to 8.5, are recombinant insulins whose primary structure has been modified mainly by introducing basic amino acids such as Arginine or Lysine. They are described, for example, in the following patents, patent applications or publications: WO 2003/053339, WO 2004/096854, U.S. Pat. Nos. 5,656,722 and 6,100,376, the content of which is incorporated by reference.

In one embodiment, the basal insulin with an isoelectric point from 5.8 to 8.5 is insulin glargine. Insulin glargine is marketed under the brand Lantus® (100 U/ml) or Toujeo® (300 U/ml) by SANOFI.

In one embodiment, the basal insulin with an isoelectric point from 5.8 to 8.5 is a bio-similar insulin glargine.

Bio-similar insulin glargine is being marketed under the brand Abasaglar® or Basaglar® by ELI LILLY.

In one embodiment, the compositions according to the invention comprise from 40 to 500 U/ml of basal insulin whose isoelectric point is comprised from 5.8 to 8.5.

In one embodiment, the compositions according to the invention comprise 40 U/ml of basal insulin whose isoelectric point is comprised from 5.8 to 8.5.

In one embodiment, the compositions according to the invention comprise 75 U/ml of basal insulin whose isoelectric point is comprised from 5.8 to 8.5.

In one embodiment, the compositions according to the invention comprise a total of 100 U/ml (or about 3.6 mg/mL) of basal insulin whose isoelectric point is comprised from 5.8 to 8.5.

In one embodiment, the compositions according to the invention comprise 150 U/ml of basal insulin whose isoelectric point is comprised from 5.8 to 8.5.

In one embodiment, the compositions according to the invention comprise a total of 200 U/ml of basal insulin whose isoelectric point is comprised from 5.8 to 8.5.

In one embodiment, the compositions according to the invention comprise 225 U/ml of basal insulin whose isoelectric point is comprised from 5.8 to 8.5.

In one embodiment, the compositions according to the invention comprise 250 U/ml of basal insulin whose isoelectric point is comprised from 5.8 to 8.5.

In one embodiment, the compositions according to the invention comprise 300 U/ml of basal insulin whose isoelectric point is comprised from 5.8 to 8.5.

In one embodiment, the compositions according to the invention comprise 400 U/ml of basal insulin whose isoelectric point is comprised from 5.8 to 8.5.

In one embodiment, the compositions according to the invention comprise 500 U/ml of basal insulin whose isoelectric point is comprised from 5.8 to 8.5.

In one embodiment, the mass ratio between basal insulin whose isoelectric point is comprised from 5.8 to 8.5, and the co-polyamino acid, or co-polyamino acid/basal insulin, is comprised from 0.2 to 8.

In one embodiment, the mass ratio is comprised from 0.2 to 6.

In one embodiment, the mass ratio is comprised from 0.2 to 5.

In one embodiment, the mass ratio is comprised from 0.2 to 4.

In one embodiment, the mass ratio is comprised from 0.2 to 3.

In one embodiment, the mass ratio is comprised from 0.2 to 2.

In one embodiment, the mass ratio is comprised from 0.2 to 1.

In one embodiment, the concentration of co-polyamino acid bearing carboxylate charges and hydrophobic radicals is at most 60 mg/ml.

In one embodiment, the concentration of co-polyamino acid bearing carboxylate charges and hydrophobic radicals is at most 40 mg/ml.

In one embodiment, the concentration of co-polyamino acid bearing carboxylate charges and hydrophobic radicals is at most than 20 mg/ml.

In one embodiment, the concentration of co-polyamino acid bearing carboxylate charges and hydrophobic radicals is at most 10 mg/ml.

In one embodiment, the concentration of co-polyamino acid bearing carboxylate charges and hydrophobic radicals is at most 5 mg/ml.

In one embodiment, the concentration of co-polyamino acid bearing carboxylate charges and hydrophobic radicals is at most 2.5 mg/ml.

In one embodiment, the compositions according to the invention also comprise a prandial insulin. Prandial insulins are soluble at pH 7.

Prandial insulin means a so-called rapid or "regular" insulin.

So-called rapid prandial insulins are insulins which must respond to the needs caused by the ingestion of proteins and sugars during a meal; they must act in less than 30 minutes.

In one embodiment, the so-called "regular" prandial insulin is human insulin.

In one embodiment, the prandial insulin is a recombinant human insulin as described in European Pharmacopeia and American Pharmacopeia.

Human insulin is marketed, for example, under the brands Humulin® (ELI LILLY) and Novolin® (NOVO NORDISK).

So-called fast acting prandial insulins are insulins which are obtained by recombination and whose primary structure has been modified to decrease their acting time.

In one embodiment, so-called fast acting prandial insulins are chosen from the group comprising insulin lispro (Humalog®), insulin glulisine (Apidra®) and insulin aspart (NovoLog®).

In one embodiment, the prandial insulin is insulin lispro.

In one embodiment, the prandial insulin is insulin glulisine.

In one embodiment, the prandial insulin is insulin aspart.

In one embodiment, the compositions according to the invention comprise in total from 60 to 800 U/ml of insulin with a combination of prandial insulin and basal insulin whose isoelectric point is comprised from 5.8 to 8.5.

In one embodiment, the compositions according to the invention comprise in total from 100 to 500 U/ml of insulin with a combination of prandial insulin and basal insulin whose isoelectric point is comprised from 5.8 to 8.5.

In one embodiment, the compositions according to the invention comprise a total of 800 U/ml of insulin with a combination of prandial insulin and basal insulin whose isoelectric point is comprised from 5.8 to 8.5.

In one embodiment, the compositions according to the invention comprise a total of 700 U/ml of insulin with a combination of prandial insulin and basal insulin whose isoelectric point is comprised from 5.8 to 8.5.

In one embodiment, the compositions according to the invention comprise a total of 600 U/ml of insulin with a combination of prandial insulin and basal insulin whose isoelectric point is comprised from 5.8 to 8.5.

In one embodiment, the compositions according to the invention comprise a total of 500 U/ml of insulin with a combination of prandial insulin and basal insulin whose isoelectric point is comprised from 5.8 to 8.5.

In one embodiment, the compositions according to the invention comprise a total of 400 U/ml of insulin with a combination of prandial insulin and basal insulin whose isoelectric point is comprised from 5.8 to 8.5.

In one embodiment, the compositions according to the invention comprise a total of 300 U/ml of insulin with a combination of prandial insulin and basal insulin whose isoelectric point is comprised from 5.8 to 8.5.

In one embodiment, the compositions according to the invention comprise a total of 266 U/ml of insulin with a combination of prandial insulin and basal insulin whose isoelectric point is comprised from 5.8 to 8.5.

In one embodiment, the compositions according to the invention comprise a total of 200 U/ml of insulin with a combination of prandial insulin and basal insulin whose isoelectric point is comprised from 5.8 to 8.5.

In one embodiment, the compositions according to the invention comprise a total of 100 U/ml of insulin with a combination of prandial insulin and basal insulin whose isoelectric point is comprised from 5.8 to 8.5.

The proportions between basal insulin with an isoelectric point from 5.8 to 8.5 and prandial insulin are, for example, by percentage, 25/75, 30/70, 40/60, 50/50, 60/40, 63/37, 70/30, 75/25, 80/20, 83/17, 90/10 for formulations as described above comprising from 60 to 800 U/mL. However, any other proportion may be achieved.

In one embodiment, the basal insulin with an isoelectric point from 5.8 to 8.5, and the prandial insulin are present respectively in the following concentrations (in U/ml) 75/25, 150/50, 200/66 or 300/100.

In one embodiment, the basal insulin with an isoelectric point from 5.8 to 8.5, and the prandial insulin are present respectively in the following concentrations (in U/ml) 75/25.

In one embodiment, the basal insulin with an isoelectric point from 5.8 to 8.5, and the prandial insulin are present respectively in the following concentrations (in U/ml) 150/50.

The ratio of hydrophobic radical to basal insulin is defined as being the ratio of their respective molar concentrations: [Hy]/[basal insulin] (mol/mol) to obtain the expected performances, that is, the solubilization of basal insulin at a pH from 6.0 to 8.0, the precipitation of the basal insulin and the stability of the compositions according to the invention.

The minimum measured value of the ratio hydrophobic radical to basal insulin [Hy]/[basal insulin], is the value at which the basal insulin is solubilized, because solubilization is the minimum effect to be obtained; this solubilization is a condition for all other technical effects which can only be observed if the basal insulin is solubilized at a pH from 6.0 to 8.0.

In the compositions according to the invention, the ratio hydrophobic radical to basal insulin [Hy]/[basal insulin] may be greater than the minimum value determined by the solubilization limit.

In one embodiment, the hydrophobic radical to basal insulin ratio [Hy]/basal insulin]≤3.

In one embodiment, the hydrophobic radical to basal insulin ratio [Hy]/basal insulin]≤2.

In one embodiment, the hydrophobic radical to basal insulin ratio [Hy]/basal insulin]≤1.75.

In one embodiment, the hydrophobic radical to basal insulin ratio [Hy]/basal insulin]≤1.5.

In one embodiment, the hydrophobic radical to basal insulin ratio [Hy]/basal insulin]≤1.25.

In one embodiment, the hydrophobic radical to basal insulin ratio [Hy]/basal insulin]≤1.00.

In one embodiment, the hydrophobic radical to basal insulin ratio [Hy]/basal insulin]≤0.75.

In one embodiment, the hydrophobic radical to basal insulin ratio [Hy]/basal insulin]≤0.5.

In one embodiment, the hydrophobic radical to basal insulin ratio [Hy]/basal insulin]≤0.25.

In one embodiment, the compositions according to the invention also comprise a gastrointestinal hormone.

By "gastrointestinal hormones" is meant hormones chosen from the group consisting of GLP-1 RA (Glucagon-like peptide-1 receptor agonist) and GIP (Glucose-dependent insulinotropic peptide), oxyntomodulin (a derivative of proglucagon), YY peptide, amylin, cholecystokinin, pancreatic peptide (PP), ghrelin and enterostatin, their analogs or derivatives and/or their pharmaceutically acceptable salts.

In one embodiment, the gastrointestinal hormones are analogs or derivatives of GLP-1 RA chosen from the group consisting of exenatide or Byetta® (ASTRA-ZENECA), liraglutide or Victoza® (NOVO NORDISK), lixisenatide or Lyxumia® (SANOFI), albiglutide or Tanzeum® (GSK) or dulaglutide or Trulicity® (ELI LILLY & CO), their analogs or derivatives and/or their pharmaceutically acceptable salts.

In one embodiment, the gastrointestinal hormone is pramlintide or Symlin® ® (ASTRA-ZENECA).

In one embodiment, the gastrointestinal hormone is exenatide or Byetta®, its analogs or derivatives and their pharmaceutically acceptable salts.

In one embodiment, the gastrointestinal hormone is liraglutide or Victoza®, its analogs or derivatives and their pharmaceutically acceptable salts.

In one embodiment, the gastrointestinal hormone is lixisenatide or Lyxumia®, its analogs or derivatives and their pharmaceutically acceptable salts.

In one embodiment, the gastrointestinal hormone is albiglutide or Tanzeum®, its analogs or derivatives and their pharmaceutically acceptable salts.

In one embodiment, the gastrointestinal hormone is dulaglutide or Trulicity®, its analogs or derivatives and their pharmaceutically acceptable salts.

In one embodiment, the gastrointestinal hormone is pramlintide or Symlin®, its analogs or derivatives and their pharmaceutically acceptable salts.

By "analog", when used in reference to a peptide or a protein, is meant a peptide or a protein in which one or more constituent residual amino acids were substituted by other residual amino acids and/or in which one or more constituent residual amino acids were deleted and/or in which one or more constituent residual amino acids were added. The percentage of homology allowed for this definition of an analog is 50%.

By "derivative", when used in reference to a peptide or protein, is meant a peptide or protein, or an analog chemically modified by a substituent which is not present in the peptide or the protein or the analog of reference, namely, a peptide or a protein which was modified by creating covalent bonds in order to introduce substituents.

In one embodiment, the substituent is chosen from the group consisting of fatty chains.

In one embodiment, the concentration of gastrointestinal hormone is comprised from 0.01 to 100 mg/mL.

In one embodiment, the concentration of exenatide, its analogs or derivatives and their pharmaceutically acceptable salts, is comprised from 0.04 to 0.5 mg/mL.

In one embodiment, the concentration of liraglutide, its analogs or derivatives and their pharmaceutically acceptable salts, is comprised from 1 to 10 mg/mL.

In one embodiment, the concentration of lixisenatide, its analogs or derivatives and their pharmaceutically acceptable salts, is comprised from 0.01 to 1 mg/mL.

In one embodiment, the concentration of albiglutide, its analogs or derivatives and their pharmaceutically acceptable salts is comprised from 5 to 100 mg/mL.

In one embodiment, the concentration of dulaglutide, its analogs or derivatives and their pharmaceutically acceptable salts is comprised from 0.1 to 10 mg/mL.

In one embodiment, the concentration of pramlintide, its analogs or derivatives and their pharmaceutically acceptable salts, is comprised from 0.1 to 5 mg/mL.

In one embodiment, compositions according to the invention are made by mixing commercial solutions of basal insulin whose isoelectric point is comprised from 5.8 to 8.5, and commercial solutions of GLP-1 RA of analog or derivative of GLP-1 RA, in volume ratios between 10/90 and 90/10.

In one embodiment, the composition according to the invention comprises a daily dose of basal insulin and a daily dose of gastrointestinal hormone.

In one embodiment, the compositions according to the invention comprise from 40 to 500 U/ml of basal insulin whose isoelectric point is comprised from 5.8 to 8.5 and from 0.05 to 0.5 mg/mL of exenatide.

In one embodiment, the compositions according to the invention comprise from 40 to 500 U/ml of basal insulin whose point is comprised from 5.8 to 8.5 and from 1 to 10 mg/mL of liraglutide.

In one embodiment, the compositions according to the invention comprise from 40 to 500 U/ml of basal insulin whose isoelectric point is comprised from 5.8 to 8.5 and from 0.01 to 1 mg/mL of lixisenatide.

In one embodiment, the compositions according to the invention comprise from 40 to 500 U/ml of basal insulin whose isoelectric point is comprised from 5.8 to 8.5, and from 5 to 100 mg/mL of albiglutide.

In one embodiment, the compositions according to the invention comprise from 40 to 500 U/ml of basal insulin whose isoelectric point is comprised from 5.8 to 8.5, and from 0.1 to 10 mg/mL of dulaglutide.

In one embodiment, the compositions according to the invention comprise 500 U/ml of basal insulin whose isoelectric point is comprised from 5.8 to 8.5 and from 0.04 to 0.5 mg/mL of exenatide.

In one embodiment, the compositions according to the invention comprise 500 U/ml of basal insulin whose isoelectric point is comprised from 5.8 to 8.5 and from 1 to 10 mg/mL of liraglutide.

In one embodiment, the compositions according to the invention comprise 500 U/ml of basal insulin whose isoelectric point is comprised from 5.8 to 8.5, and from 0.01 to 1 mg/mL of lixisenatide.

In one embodiment, the compositions according to the invention comprise 500 U/ml of basal insulin whose isoelectric point is comprised from 5.8 to 8.5 and from 5 to 100 mg/mL of albiglutide.

In one embodiment, the compositions according to the invention comprise 500 U/ml of basal insulin whose isoelectric point is comprised from 5.8 to 8.5 and from 0.1 to 10 mg/mL of dulaglutide.

In one embodiment, the compositions according to the invention comprise 400 U/ml of basal insulin whose isoelectric point is comprised from 5.8 to 8.5 and from 0.04 to 0.5 mg/mL of exenatide.

In one embodiment, the compositions according to the invention comprise 400 U/ml of basal insulin whose isoelectric point is comprised from 5.8 to 8.5 and from 1 to 10 mg/mL of liraglutide.

In one embodiment, the compositions according to the invention comprise 400 U/ml of basal insulin whose isoelectric point is comprised from 5.8 to 8.5, and from 0.01 to 1 mg/mL of lixisenatide.

In one embodiment, the compositions according to the invention comprise 400 U/ml of basal insulin whose isoelectric point is comprised from 5.8 to 8.5 and from 5 to 100 mg/mL of albiglutide.

In one embodiment, the compositions according to the invention comprise 400 U/ml of basal insulin whose isoelectric point is comprised from 5.8 to 8.5 and from 0.1 to 10 mg/mL of dulaglutide.

In one embodiment, the compositions according to the invention comprise 300 U/ml of basal insulin whose isoelectric point is comprised from 5.8 to 8.5 and from 0.04 to 0.5 mg/mL of exenatide.

In one embodiment, the compositions according to the invention comprise 300 U/ml of basal insulin whose isoelectric point is comprised from 5.8 to 8.5 and from 1 to 10 mg/mL of liraglutide.

In one embodiment, the compositions according to the invention comprise 300 U/ml of basal insulin whose isoelectric point is comprised from 5.8 to 8.5, and from 0.01 to 1 mg/mL of lixisenatide.

In one embodiment, the compositions according to the invention comprise 300 U/ml of basal insulin whose isoelectric point is comprised from 5.8 to 8.5 and from 5 to 100 mg/mL of albiglutide.

In one embodiment, the compositions according to the invention comprise 300 U/ml of basal insulin whose isoelectric point is comprised from 5.8 to 8.5 and from 0.1 to 10 mg/mL of dulaglutide.

In one embodiment, the compositions according to the invention comprise 225 U/ml of basal insulin whose isoelectric point is comprised from 5.8 to 8.5 and from 0.04 to 0.5 mg/mL of exenatide.

In one embodiment, the compositions according to the invention comprise 225 U/ml of basal insulin whose isoelectric point is comprised from 5.8 to 8.5 and from 1 to 10 mg/mL of liraglutide.

In one embodiment, the compositions according to the invention comprise 225 U/ml of basal insulin whose isoelectric point is comprised from 5.8 to 8.5, and from 0.01 to 1 mg/mL of lixisenatide.

In one embodiment, the compositions according to the invention comprise 225 U/ml of basal insulin whose isoelectric point is comprised from 5.8 to 8.5 and from 5 to 100 mg/mL of albiglutide.

In one embodiment, the compositions according to the invention comprise 225 U/ml of basal insulin whose isoelectric point is comprised from 5.8 to 8.5 and from 0.1 to 10 mg/mL of dulaglutide.

In one embodiment, the compositions according to the invention comprise 200 U/ml of basal insulin whose isoelectric point is comprised from 5.8 to 8.5 and from 0.04 to 0.5 mg/mL of exenatide.

In one embodiment, the compositions according to the invention comprise 200 U/ml of basal insulin whose isoelectric point is comprised from 5.8 to 8.5 and from 1 to 10 mg/mL of liraglutide.

In one embodiment, the compositions according to the invention comprise 200 U/ml of basal insulin whose isoelectric point is comprised from 5.8 to 8.5, and from 0.01 to 1 mg/mL of lixisenatide.

In one embodiment, the compositions according to the invention comprise 200 U/ml of basal insulin or which the isoelectric point is comprised from 5.8 to 8.5 and from 5 to 100 mg/mL of albiglutide.

In one embodiment, the compositions according to the invention comprise 200 U/ml of basal insulin whose isoelectric point is comprised from 5.8 to 8.5 and from 0.1 to 10 mg/mL of dulaglutide.

In one embodiment, the compositions according to the invention comprise 100 U/ml (or about 3.6 mg/mL) of basal insulin whose isoelectric point is comprised from 5.8 to 8.5 and from 0.04 to 0.5 mg/mL of exenatide.

In one embodiment, the compositions according to the invention comprise 100 U/ml (or about 3.6 mg/mL) of basal insulin whose isoelectric point is comprised from 5.8 to 8.5 and from 1 to 10 mg/mL of liraglutide.

In one embodiment, the compositions according to the invention comprise 100 U/ml (or about 3.6 mg/mL) of basal insulin whose isoelectric point is comprised from 5.8 to 8.5, and from 0.01 to 1 mg/mL of lixisenatide.

In one embodiment, the compositions according to the invention comprise 100 U/ml of basal insulin whose isoelectric point is comprised from 5.8 to 8.5 and from 5 to 100 mg/mL of albiglutide.

In one embodiment, the compositions according to the invention comprise 100 U/ml of basal insulin whose isoelectric point is comprised from 5.8 to 8.5 and from 0.1 to 10 mg/mL of dulaglutide.

In one embodiment, the compositions according to the invention comprise 40 U/ml of basal insulin whose isoelectric point is comprised from 5.8 to 8.5 and from 0.04 to 0.5 mg/mL of exenatide.

In one embodiment, the compositions according to the invention comprise 40 U/ml of basal insulin whose isoelectric point is comprised from 5.8 to 8.5 and from 1 to 10 mg/mL of liraglutide.

In one embodiment, the compositions according to the invention comprise 40 U/ml of basal insulin whose isoelectric point is comprised from 5.8 to 8.5, and from 0.01 to 1 mg/mL of lixisenatide.

In one embodiment, the compositions according to the invention comprise 40 U/ml of basal insulin whose isoelectric point is comprised from 5.8 to 8.5 and from 5 to 100 mg/mL of albiglutide.

In one embodiment, the compositions according to the invention comprise 40 U/ml of basal insulin whose isoelectric point is comprised from 5.8 to 8.5 and from 0.1 to 10 mg/mL of dulaglutide.

The invention also relates to compositions which further comprise ionic species, the said ionic species allowing to improve the stability of the compositions.

The invention also relates to the use of ionic species chosen from the group of anions, cations and or zwitterions to improve the physico-chemical stability of the compositions.

In one embodiment, the ionic species comprise less than 10 carbon atoms.

Said ionic species are chosen from the group of anions, cations and/or zwitterions. By zwitterion is meant a species bearing at least one positive charge and at least one negative charge on two non-adjacent atoms.

Said ionic species are used alone or in mixture and preferably in mixture.

In one embodiment, the anions are chosen from organic anions.

In one embodiment, the ionic organic anions comprise less than 10 carbon atoms.

In one embodiment, the organic anions are chosen from the group consisting of acetate, citrate and succinate.

In one embodiment, the anions are chosen from anions of mineral origin.

In one embodiment, the anions of mineral origin are chosen from the group consisting of sulphates, phosphates and halides, specifically chlorides.

In one embodiment, the cations are chosen from organic cations.

In one embodiment, the organic cations comprise less than 10 carbon atoms.

In one embodiment, the organic cations are chosen from the group consisting of ammoniums, for example, 2-Amino-2-(hydroxymethyl)propane-1,3 where the amine is in the form of ammonium.

In one embodiment, the cations are chosen from cations of mineral origin.

In one embodiment, the cations of mineral origin are chosen from the group consisting of zinc, in particular $Zn^{2+}$ and alkaline metals, in particular, $Na^+$ and $K^+$, In one embodiment, the zwitterions are chosen from zwitterions of organic origin.

In one embodiment, the zwitterions of organic origin are chosen from the amino acids.

In one embodiment, the amino acids are chosen from the aliphatic amino acids in the group consisting of glycine, alanine, valine, isoleucine and leucine.

In one embodiment, the amino acids are chosen from the cyclic amino acids in the group consisting of proline In one embodiment, the amino acids are chosen from the hydroxylated or sulphur-containing amino acids in the group consisting of cysteine, serine, threonine and methionine.

In one embodiment, the amino acids are chosen from the aromatic amino acids in the group consisting of phenylalanine, tyrosine and tryptophan.

In one embodiment, the amino acids are chosen from the amino acids whose carboxyl function of the side chain is amidated in the group consisting of asparagine and glutamine.

In one embodiment, the zwitterions of organic origin are chosen from the group consisting of amino acids with an uncharged side chain.

In one embodiment, the zwitterions of organic origin are chosen from the group consisting of aminoacids or acidic amino acids.

In one embodiment, the aminoacids are chosen from the group consisting of glutamic acid and aspartic acid, optionally in the form of salts.

In one embodiment, the zwitterions of organic origin are chosen from the group consisting of basic or so-called "cationic" amino acids.

In one embodiment, the so-called "cationic" amino acids are chosen from arginine, histidine and lysine, in particular, arginine and lysine.

Particularly, zwitterions comprise as many negative charges as positive charges, and therefore a zero overall charge at the isoelectric point and/or at a pH comprised from 6.0 to 8.0.

Said ionic species are introduced into the compositions in the form of salts.

The introduction of these salts may be done in solid form before their dissolution in the compositions, or in the form of a solution, in particular, a concentrated solution.

For example, cations of mineral origin are added in the form of salts chosen from sodium chloride, zinc chloride, sodium phosphate, sodium sulphate, etc.

As examples, anions of organic origin are added in the form of salts chosen from sodium or potassium citrate, sodium acetate.

For example, the amino acids are added in the form of salts chosen from arginine hydrochloride, histidine hydrochloride or in non-salified form such as, for example, histidine, arginine.

In one embodiment, the total molar concentration in ionic species in the composition is greater than or equal to 10 mM.

In one embodiment, the total molar concentration in ionic species in the composition is greater than or equal to 20 mM.

In one embodiment, the total molar concentration in ionic species in the composition is greater than or equal to 30 mM.

In one embodiment, the total molar concentration in ionic species in the composition is greater than or equal to 50 mM.

In one embodiment, the total molar concentration in ionic species in the composition is greater than or equal to 75 mM.

In one embodiment, the total molar concentration in ionic species in the composition is greater than or equal to 100 mM.

In one embodiment, the total molar concentration in ionic species in the composition is greater than or equal to 200 mM.

In one embodiment, the total molar concentration in ionic species in the composition is greater than or equal to 300 mM.

In one embodiment, the total molar concentration in ionic species in the composition is greater than or equal to 500 mM.

In one embodiment, the total molar concentration in ionic species in the composition is greater than or equal to 600 mM.

In one embodiment, the total molar concentration in ionic species in the composition is greater than or equal to 700 mM.

In one embodiment, the total molar concentration in ionic species in the composition is greater than or equal to 800 mM.

In one embodiment, the total molar concentration in ionic species in the composition is greater than or equal to 900 mM.

In one embodiment, the total molar concentration in ionic species in the composition is less than or equal to 1000 mM.

In one embodiment, the total molar concentration in ionic species in the composition is less than or equal to 1500 mM.

In one embodiment, the total molar concentration in ionic species in the composition is less than or equal to 1200 mM.

In one embodiment, the total molar concentration in ionic species in the composition is less than or equal to 1000 mM.

In one embodiment, the total molar concentration in ionic species in the composition is less than or equal to 900 mM.

In one embodiment, the total molar concentration in ionic species in the composition is less than or equal to 800 mM.

In one embodiment, the total molar concentration in ionic species in the composition is less than or equal to 700 mM.

In one embodiment, the total molar concentration in ionic species in the composition is less than or equal to 600 mM.

In one embodiment, the total molar concentration in ionic species in the composition is less than or equal to 500 mM.

In one embodiment, the total molar concentration in ionic species in the composition is less than or equal to 400 mM.

In one embodiment, the total molar concentration in ionic species in the composition is less than or equal to 300 mM.

In one embodiment, the total molar concentration in ionic species in the composition is less than or equal to 200 mM.

In one embodiment, the total molar concentration in ionic species in the composition is less than or equal to 100 mM.

In one embodiment, the total molar concentration in ionic species in the composition is comprised from 10 to 1000 mM.

In one embodiment, the total molar concentration in ionic species in the composition is comprised from 20 to 1000 mM.

In one embodiment, the total molar concentration in ionic species in the composition is comprised from 30 to 1000 mM.

In one embodiment, the total molar concentration in ionic species in the composition is comprised from 50 to 1000 mM.

In one embodiment, the total molar concentration in ionic species in the composition is comprised from 75 to 1000 mM.

In one embodiment, the total molar concentration in ionic species in the composition is comprised from 100 to 1000 mM.

In one embodiment, the total molar concentration in ionic species in the composition is comprised from 200 to 1000 mM.

In one embodiment, the total molar concentration in ionic species in the composition is comprised from 300 to 1000 mM.

In one embodiment, the total molar concentration in ionic species in the composition is comprised from 400 to 1000 mM.

In one embodiment, the total molar concentration in ionic species in the composition is comprised from 500 to 1000 mM.

In one embodiment, the total molar concentration in ionic species in the composition is comprised from 600 to 1000 mM.

In one embodiment, the total molar concentration in ionic species in the composition is comprised from 10 to 900 mM.

In one embodiment, the total molar concentration in ionic species in the composition is comprised from 20 to 900 mM.

In one embodiment, the total molar concentration in ionic species in the composition is comprised from 30 to 900 mM.

In one embodiment, the total molar concentration in ionic species in the composition is comprised from 50 to 900 mM.

In one embodiment, the total molar concentration in ionic species in the composition is comprised from 75 to 900 mM.

In one embodiment, the total molar concentration in ionic species in the composition is comprised from 100 to 900 mM.

In one embodiment, the total molar concentration in ionic species in the composition is comprised from 200 to 900 mM.

In one embodiment, the total molar concentration in ionic species in the composition is comprised from 300 to 900 mM.

In one embodiment, the total molar concentration in ionic species in the composition is comprised from 400 to 900 mM.

In one embodiment, the total molar concentration in ionic species in the composition is comprised from 500 to 900 mM.

In one embodiment, the total molar concentration in ionic species in the composition is comprised from 600 to 900 mM.

In one embodiment, the total molar concentration in ionic species in the composition is comprised from 10 to 900 mM.

In one embodiment, the total molar concentration in ionic species in the composition is comprised from 20 to 800 mM.

In one embodiment, the total molar concentration in ionic species in the composition is comprised from 30 to 800 mM.

In one embodiment, the total molar concentration in ionic species in the composition is comprised from 50 to 800 mM.

In one embodiment, the total molar concentration in ionic species in the composition is comprised from 75 to 800 mM.

In one embodiment, the total molar concentration in ionic species in the composition is comprised from 100 to 800 mM.

In one embodiment, the total molar concentration in ionic species in the composition is comprised from 200 to 800 mM.

In one embodiment, the total molar concentration in ionic species in the composition is comprised from 300 to 800 mM.

In one embodiment, the total molar concentration in ionic species in the composition is comprised from 400 to 800 mM.

In one embodiment, the total molar concentration in ionic species in the composition is comprised from 500 to 800 mM.

In one embodiment, the total molar concentration in ionic species in the composition is comprised from 600 to 800 mM.

In one embodiment, the total molar concentration in ionic species in the composition is comprised from 10 to 700 mM.

In one embodiment, the total molar concentration in ionic species in the composition is comprised from 20 to 700 mM.

In one embodiment, the total molar concentration in ionic species in the composition is comprised from 30 to 700 mM.

In one embodiment, the total molar concentration in ionic species in the composition is comprised from 50 to 700 mM.

In one embodiment, the total molar concentration in ionic species in the composition is comprised from 75 to 700 mM.

In one embodiment, the total molar concentration in ionic species in the composition is comprised from 100 to 700 mM.

In one embodiment, the total molar concentration in ionic species in the composition is comprised from 200 to 700 mM.

In one embodiment, the total molar concentration in ionic species in the composition is comprised from 300 to 700 mM.

In one embodiment, the total molar concentration in ionic species in the composition is comprised from 400 to 700 mM.

In one embodiment, the total molar concentration in ionic species in the composition is comprised from 500 to 700 mM.

In one embodiment, the total molar concentration in ionic species in the composition is comprised from 600 to 700 mM.

In one embodiment, the total molar concentration in ionic species in the composition is comprised from 10 to 600 mM.

In one embodiment, the total molar concentration in ionic species in the composition is comprised from 20 to 600 mM.

In one embodiment, the total molar concentration in ionic species in the composition is comprised from 30 to 600 mM.

In one embodiment, the total molar concentration in ionic species in the composition is comprised from 50 to 600 mM.

In one embodiment, the total molar concentration in ionic species in the composition is comprised from 75 to 600 mM.

In one embodiment, the total molar concentration in ionic species in the composition is comprised from 100 to 600 mM.

In one embodiment, the total molar concentration in ionic species in the composition is comprised from 200 to 600 mM.

In one embodiment, the total molar concentration in ionic species in the composition is comprised from 300 to 600 mM.

In one embodiment, the total molar concentration in ionic species in the composition is comprised from 40 to 600 mM.

In one embodiment, the total molar concentration in ionic species in the composition is comprised from 500 to 600 mM.

In one embodiment, the total molar concentration in ionic species in the composition is comprised from 10 to 500 mM.

In one embodiment, the total molar concentration in ionic species in the composition is comprised from 20 to 500 mM.

In one embodiment, the total molar concentration in ionic species in the composition is comprised from 30 to 500 mM.

In one embodiment, the total molar concentration in ionic species in the composition is 50 to 500 mM.

In one embodiment, the total molar concentration in ionic species in the composition is comprised from 75 to 500 mM.

In one embodiment, the total molar concentration in ionic species in the composition is comprised from 100 to 500 mM.

In one embodiment, the total molar concentration in ionic species in the composition is comprised from 200 to 500 mM.

In one embodiment, the total molar concentration in ionic species in the composition is comprised from 300 to 500 mM.

In one embodiment, the total molar concentration in ionic species in the composition is comprised from 400 to 500 mM.

In one embodiment, the total molar concentration in ionic species in the composition is comprised from 10 to 400 mM.

In one embodiment, the total molar concentration in ionic species in the composition is comprised from 20 to 400 mM.

In one embodiment, the total molar concentration in ionic species in the composition is comprised from 30 to 400 mM.

In one embodiment, the total molar concentration in ionic species in the composition is comprised from 50 to 400 mM.

In one embodiment, the total molar concentration in ionic species in the composition is comprised from 75 to 400 mM.

In one embodiment, the total molar concentration in ionic species in the composition is comprised from 100 to 400 mM.

In one embodiment, the total molar concentration in ionic species in the composition is comprised from 200 to 400 mM.

In one embodiment, the total molar concentration in ionic species in the composition is comprised from 300 to 400 mM.

In one embodiment, the total molar concentration in ionic species in the composition is comprised from 10 to 300 mM.

In one embodiment, the total molar concentration in ionic species in the composition is comprised from 20 to 300 mM.

In one embodiment, the total molar concentration in ionic species in the composition is comprised from 30 to 300 mM.

In one embodiment, the total molar concentration in ionic species in the composition is comprised from 50 to 300 mM.

In one embodiment, the total molar concentration in ionic species in the composition is comprised from 75 to 300 mM.

In one embodiment, the total molar concentration in ionic species in the composition is comprised from 100 to 300 mM.

In one embodiment, the total molar concentration in ionic species in the composition is comprised from 200 to 300 mM.

In one embodiment, the total molar concentration in ionic species in the composition is comprised from 10 to 200 mM.

In one embodiment, the total molar concentration in ionic species in the composition is comprised from 20 to 200 mM.

In one embodiment, the total molar concentration in ionic species in the composition is comprised from 30 to 200 mM.

In one embodiment, the total molar concentration in ionic species in the composition is comprised from 50 to 200 mM.

In one embodiment, the total molar concentration in ionic species in the composition is comprised from 75 to 200 mM.

In one embodiment, the total molar concentration in ionic species in the composition is comprised from 100 to 200 mM.

In one embodiment, the total molar concentration in ionic species in the composition is comprised from 10 to 100 mM.

In one embodiment, the total molar concentration in ionic species in the composition is comprised from 20 to 100 mM.

In one embodiment, the total molar concentration in ionic species in the composition is comprised from 30 to 100 mM.

In one embodiment, the total molar concentration in ionic species in the composition is comprised from 50 to 100 mM.

In one embodiment, the total molar concentration in ionic species in the composition is comprised from 75 to 100 mM.

In one embodiment, the total molar concentration in ionic species in the composition is comprised from 10 to 75 mM.

In one embodiment, the total molar concentration in ionic species in the composition is comprised from 20 to 75 mM.

In one embodiment, the total molar concentration in ionic species in the composition is comprised from 30 to 75 mM.

In one embodiment, the total molar concentration in ionic species in the composition is comprised from 50 to 75 mM.

In one embodiment, the total molar concentration in ionic species in the composition is comprised from 10 to 50 mM.

In one embodiment, the total molar concentration in ionic species in the composition is comprised from 20 to 50 mM.

In one embodiment, the total molar concentration in ionic species in the composition is comprised from 30 to 50 mM.

In one embodiment, said ionic species are present in a concentration of 5 to 400 mM.

In one embodiment, said ionic species are present in a concentration of 5 to 300 mM.

In one embodiment, said ionic species are present in a concentration of 5 to 200 mM.

In one embodiment, said ionic species are present in a concentration of 5 to 100 mM.

In one embodiment, said ionic species are present in a concentration of 5 to 75 mM.

In one embodiment, said ionic species are present in a concentration of 5 to 50 mM.

In one embodiment, said ionic species are present in a concentration of 5 to 25 mM.

In one embodiment, said ionic species are present in a concentration of 5 to 20 mM.

In one embodiment, said ionic species are present in a concentration of 5 to 10 mM.

In one embodiment, said ionic species are present in a concentration of 10 to 400 mM.

In one embodiment, said ionic species are present in a concentration of 10 to 300 mM.

In one embodiment, said ionic species are present in a concentration of 10 to 200 mM.

In one embodiment, said ionic species are present in a concentration of 10 to 100 mM.

In one embodiment, said ionic species are present in a concentration of 10 to 75 mM.

In one embodiment, said ionic species are present in a concentration of 10 to 50 mM.

In one embodiment, said ionic species are present in a concentration of 10 to 25 mM.

In one embodiment, said ionic species are present in a concentration of 10 to 20 mM.

In one embodiment, said ionic species are present in a concentration of 20 to 300 mM.

In one embodiment, said ionic species are present in a concentration of 20 to 200 mM.

In one embodiment, said ionic species are present in a concentration of 20 to 100 mM.

In one embodiment, said ionic species are present in a concentration of 20 to 75 mM.

In one embodiment, said ionic species are present in a concentration of 20 to 50 mM.

In one embodiment, said ionic species are present in a concentration of 20 to 25 mM.

In one embodiment, said ionic species are present in a concentration of 50 to 300 mM.

In one embodiment, said ionic species are present in a concentration of 50 to 200 mM.

In one embodiment, said ionic species are present in a concentration of 50 to 100 mM.

In one embodiment, said ionic species are present in a concentration of 50 to 75 mM.

Regarding cations of mineral origin, and in particular, $Zn^{2+}$, its molar concentration in the composition may be from 0.25 to 20 mM, in particular, from 0.25 to 10 mM or from 0.25 to 5 mM.

In one embodiment, the composition comprises zinc.

In one embodiment, the composition comprises from 0.2 to 2 mM of zinc.

In one embodiment, the composition comprises NaCl.

In one embodiment, the NaCl is present in a concentration of 2 to 25 mM.

In one embodiment, the NaCl is present in a concentration of 2.5 to 20 mM.

In one embodiment, the NaCl is present in a concentration of 4 to 15 mM.

In one embodiment, the NaCl is present in a concentration of 5 to 10 mM.

In one embodiment, the compositions according to the invention also comprise buffers.

In one embodiment, the composition according to the invention comprises buffers at concentrations from 0 to 100 mM.

In one embodiment, the composition according to the invention comprises buffers at concentrations from 15 to 50 mM.

In one embodiment, the compositions according to the invention comprise a buffer chosen from the group consisting of a phosphate buffer, Tris (trishydroxymethyl)aminomethane and sodium citrate.

In one embodiment, the buffer is sodium phosphate.

In one embodiment, the buffer is Tris (trishydroxymethyl) aminomethane.

In one embodiment, the buffer is sodium citrate.

In one embodiment, compositions according to the invention also comprise zinc salts at concentrations from 0 to 5000 μM.

In one embodiment, the composition according to the invention comprises zinc salts at concentrations from 0 to 4000 μM.

In one embodiment, compositions according to the invention also comprise zinc salts at concentrations from 0 to 3000 μM.

In one embodiment, compositions according to the invention also comprise zinc salts at concentrations from 0 to 2000 μM.

In one embodiment, compositions according to the invention also comprise zinc salts at concentrations from 0 to 1000 μM.

In one embodiment, compositions according to the invention also comprise zinc salts at concentrations from 50 to 600 μM.

In one embodiment, compositions according to the invention also comprise zinc salts at concentrations from 100 to 500 μM.

In one embodiment, the composition according to the invention comprises zinc salts at concentrations from 200 to 500 μM.

In one embodiment, the compositions according to the invention also comprise preservatives.

In one embodiment, the preservatives are chosen from the group consisting of m-cresol and phenol, alone or in mixture.

In one embodiment, the concentration of the preservatives is comprised from 10 to 50 mM.

In one embodiment, the concentration of the preservatives is comprised from 10 to 40 mM.

In one embodiment, the compositions according to the invention further comprise a surfactant.

In one embodiment, the surfactant is chosen from the group consisting of propylene glycol and polysorbate.

Compositions according to the invention may further comprise additives such as tonicity agents.

In one embodiment, the tonicity agents are chosen from the group consisting of glycerine, sodium chloride, mannitol and glycine.

Compositions according to the invention may further comprise all excipients compliant with pharmacopoeias and compatible with the insulins used at the customary concentrations.

The invention also relates to a pharmaceutical formulation according to the invention, characterized in that it is obtained by drying and/or lyophilization.

In the case of local and systemic releases, the routes of administration considered are intravenous, subcutaneous, intradermal or intramuscular.

Transdermal, oral, nasal, vaginal, ocular, oral and pulmonary routes of administration are also considered.

In one embodiment, the composition according to the invention is characterized in that it is administered 1 time per day.

In one embodiment, the composition according to the invention is characterized in that it is administered 2 times per day.

In one embodiment, the composition according to the invention is characterized in that it is administered 2 times per day.

In one embodiment, the composition according to the invention is characterized in that it also comprises a prandial insulin.

In one embodiment, the composition according to the invention further comprising at least one prandial insulin is characterized in that it is administered 1 time per day.

In one embodiment, the composition according to the invention further comprising at least one prandial insulin is characterized in that it is administered at least 2 times per day.

In one embodiment, the composition according to the invention further comprising at least one prandial insulin is characterized in that it is administered 2 times per day.

In one embodiment, the composition according to the invention is characterized in that it also comprises a gastrointestinal hormone.

In one embodiment, the composition according to the invention further comprising at least one gastrointestinal hormone is characterized in that it is administered 1 time per day.

In one embodiment, the composition according to the invention further comprising at least one gastrointestinal hormone is characterized in that it is administered at least 2 times per day.

In one embodiment, the composition according to the invention further comprising at least one gastro-intestinal hormone is characterized in that it is administered 2 times per day.

In one embodiment, the composition according to the invention is characterized in that the gastrointestinal hormone is a GLP-1 RA.

In one embodiment, the composition according to the invention further comprising a GLP-1 RA is characterized in that it is administered 1 time per day.

In one embodiment, the composition according to the invention further comprising at least one GLP-1 RA is administered at least 2 times per day.

In one embodiment, the composition according to the invention further comprising at least one GLP-1 RA is characterized in that it is administered 2 times per day.

The invention also relates to single-dose formulations at pH from 6.0 to 8.0 comprising a basal insulin whose isoelectric point is comprised from 5.8 to 8.5.

The invention also relates to single-dose formulations at pH from 6.0 to 8.0 comprising a basal insulin whose isoelectric point is comprised from 5.8 to 8.5, and one prandial insulin.

The invention also relates to single-dose formulations at pH from 6.0 to 8.0 comprising a basal insulin whose isoelectric point is comprised from 5.8 to 8.5, and a gastrointestinal hormone, as defined above.

The invention also relates to single-dose formulations at pH from 6.0 to 8.0 comprising a basal insulin whose isoelectric point is comprised from 5.8 to 8.5, a prandial insulin and a gastrointestinal hormone, as defined above.

The invention also relates to single-dose formulations at pH from 6.6 to 7.8 comprising a basal insulin whose isoelectric point is comprised from 5.8 to 8.5.

The invention also relates to single-dose formulations at pH from 6.6 to 7.8 comprising a basal insulin whose isoelectric point is comprised from 5.8 to 8.5, and one prandial insulin.

The invention also relates to single-dose formulations at pH from 6.6 to 7.8 comprising a basal insulin whose isoelectric point is comprised from 5.8 to 8.5, and a gastrointestinal hormone, as defined above.

The invention also relates to single-dose formulations at pH from 6.6 to 7.8 comprising a basal insulin whose isoelectric point is comprised from 5.8 to 8.5, a prandial insulin and a gastrointestinal hormone, as defined above.

The invention also relates to single-dose formulations at pH from 6.6 to 7.6 comprising a basal insulin whose isoelectric point is comprised from 5.8 to 8.5.

The invention also relates to single-dose formulations at pH from 6.6 to 7.6 comprising a basal insulin whose isoelectric point is comprised from 5.8 to 8.5, and a prandial insulin.

The invention also relates to single-dose formulations at pH from 6.6 to 7.6 comprising a basal insulin whose isoelectric point is comprised from 5.8 to 8.5, and a gastrointestinal hormone, as defined above.

The invention also relates to single-dose formulations at pH from 6.6 to 7.6 comprising a basal insulin whose isoelectric point is comprised from 5.8 to 8.5, a prandial insulin and a gastrointestinal hormone, as defined above.

In one embodiment, the single-dose formulations further comprise a co-polyamino acid as defined above.

In one embodiment, the formulations are in the form of an injectable solution.

In one embodiment, the basal insulin whose isoelectric point is comprised from 5.8 to 8.5 is insulin glargine.

In one embodiment, the GLP-1 RA, analog or derivative of GLP-1 RA, is chosen from the group comprising exenatide (Byetta®), liraglutide (Victoza®), lixisenatide (Lyxumia®), albiglutide (Tanzeum®), dulaglutide (Trulicity®) or one of their derivatives.

In one embodiment, the gastrointestinal hormone is exenatide.

In one embodiment, the gastrointestinal hormone is liraglutide.

In one embodiment, the gastrointestinal hormone is lixisenatide.

In one embodiment, the gastrointestinal hormone is albiglutide.

In one embodiment, the gastrointestinal hormone is dulaglutide.

Solubilization at a pH from 6.0 to 8.0 of basal insulins whose isoelectric point is comprised from 5.8 to 8.5, by co-polyamino acids bearing carboxylate charges and at least one hydrophobic radical according to the invention, may be simply observed and monitored, with the naked eye, through a change in the appearance of the solution.

Solubilization at a pH from 6.6 to 7.8 of basal insulins whose isoelectric point is comprised from 5.8 to 8.5, by co-polyamino acids bearing carboxylate charges and at least one hydrophobic radical according to the invention, may be simply observed and monitored, with the naked eye, through a change in the appearance of the solution.

Furthermore, and just as importantly, the applicant has been able to verify that a basal insulin whose isoelectric point is comprised from 5.8 to 8.5, solubilized at a pH from 6.0 to 8.0 in the presence of a co-polyamino acid bearing carboxylate charges and at least one hydrophobic radical according to the invention, preserves its slow-acting insulin action, whether alone or in combination with a prandial insulin or a gastrointestinal hormone.

The applicant was also able to verify that a prandial insulin mixed at pH from 6.0 to 8.0 in the presence of a co-polyamino acid bearing carboxylate charges and at least one hydrophobic radical according to the invention and a basal insulin whose isoelectric point is comprised from 5.8 to 8.5, preserves its rapid-release insulin action.

It is advantageously possible to prepare a composition according to the invention by simply mixing an aqueous solution of basal insulin whose isoelectric point is comprised from 5.8 to 8.5 and a co-polyamino acid bearing carboxylate charges and at least one hydrophobic radical according to the invention, in aqueous solution or in lyophilized form. If necessary, the pH of the preparation is adjusted to a pH from 6.0 to 8.0.

It is advantageously possible to prepare a composition according to the invention by simply mixing an aqueous solution of basal insulin whose isoelectric point is comprised from 5.8 to 8.5 and a solution of prandial insulin, and a co-polyamino acid bearing carboxylate charges and at least one hydrophobic radical according to the invention, in aqueous solution or in lyophilized form. If necessary, the pH of the preparation is adjusted to a pH from 6.0 to 8.0.

It is advantageously possible to prepare a composition according to the invention by simply mixing an aqueous solution of basal insulin whose isoelectric point is comprised from 5.8 to 8.5, and a solution of GLP-1 RA, an analog or derivative of GLP-1 RA and a co-polyamino acid bearing carboxylate charges and at least one hydrophobic radical according to the invention, in aqueous solution or in lyophilized form. If necessary, the pH of the preparation is adjusted to a pH from 6.0 to 8.0.

It is advantageously possible to prepare a composition according to the invention by simply mixing an aqueous solution of basal insulin whose isoelectric point is comprised from 5.8 to 8.5 and a solution of prandial insulin, and a solution of GLP-1 RA or an analog or derivative of GLP-1 RA, and a co-polyamino acid bearing carboxylate charges and at least one hydrophobic radical according to the invention, in aqueous solution or in lyophilized form. If necessary, the pH of the preparation is adjusted to a pH from 6.0 to 8.0.

In one embodiment, the mixture of basal insulin and co-polyamino acid is concentrated by ultrafiltration before mixing with the prandial insulin in aqueous solution or in lyophilized form.

If necessary, the composition of the mixture is adjusted with excipients such as glycerine, m-cresol, zinc chloride and polysorbate (Tween®) by addition of concentrated solutions of these excipients to the mixture. If necessary, the pH of the preparation is adjusted to a pH from 6.0 to 8.0.

Part A—Synthesis of Intermediate Hydrophobic Compounds Hy Allowing to Obtain Radicals -Hy.

| No. | INTERMEDIATE HYDROPHOBIC COMPOUNDS |
|---|---|
| A1 | 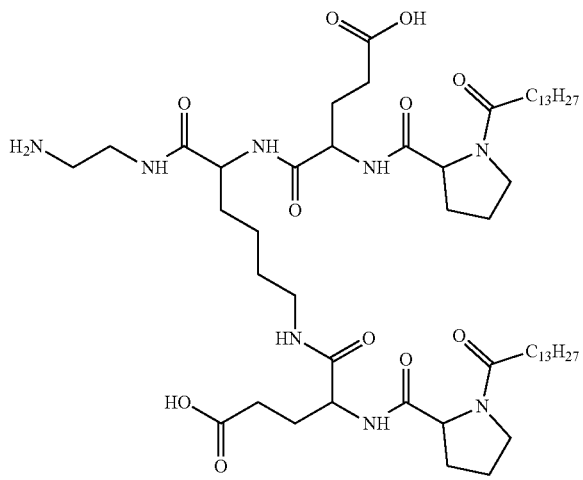 |
| A2 | 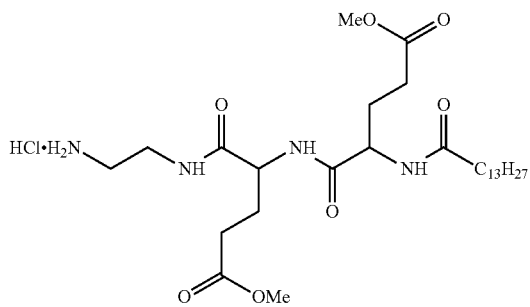 |

| No. | INTERMEDIATE HYDROPHOBIC COMPOUNDS |
|---|---|
| A3 | 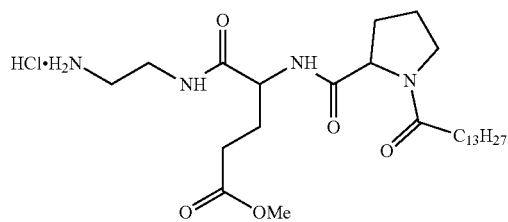 |
| A4 | 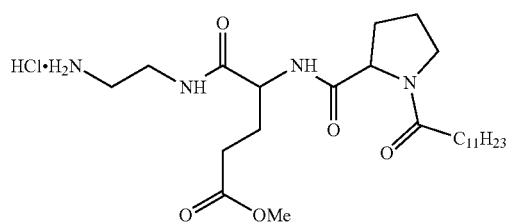 |
| A5 | 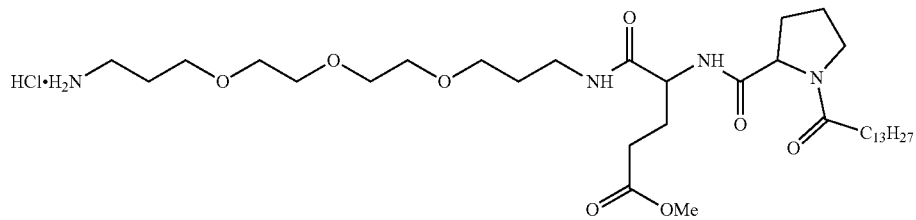 |
| A7 | 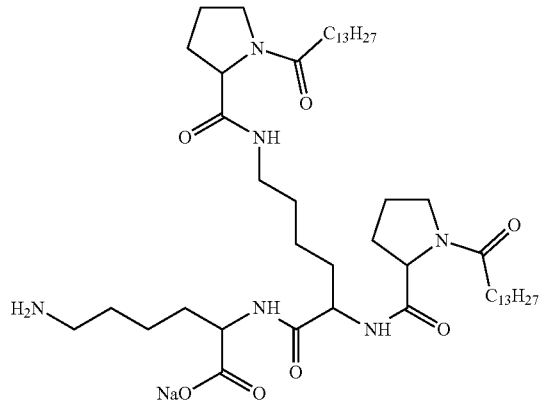 |
| A5a | 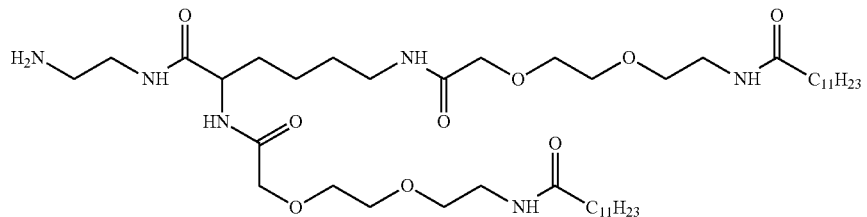 |
| A6a | 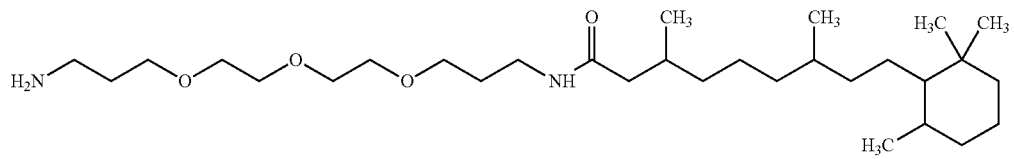 [SMILES: CC(CCCC(C)CC(=O)NCCCOCCOCCOCCCN)CCC1C(C)CCCC1(C)C] |

| No. | INTERMEDIATE HYDROPHOBIC COMPOUNDS |
|---|---|
| A8 | 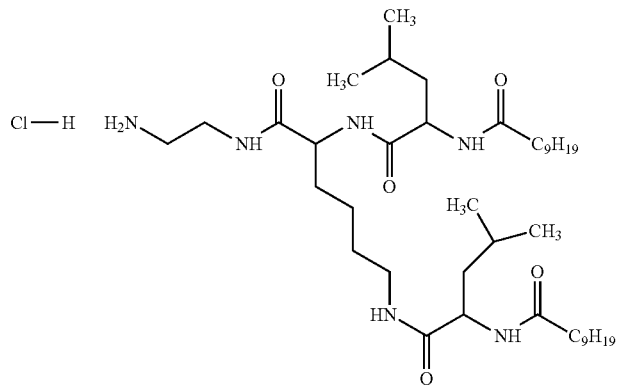 |
| A9 | 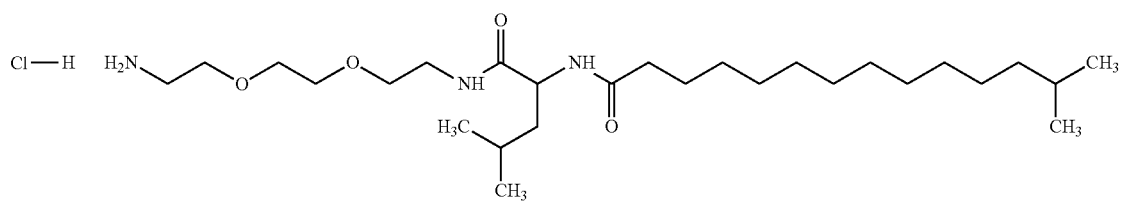 [SMILES: Cl ; CC(C)CCCCCCCCCCCC(=O)NC(CC(C)C)C(=O)NCCOCCOCCN] |
| A10 | 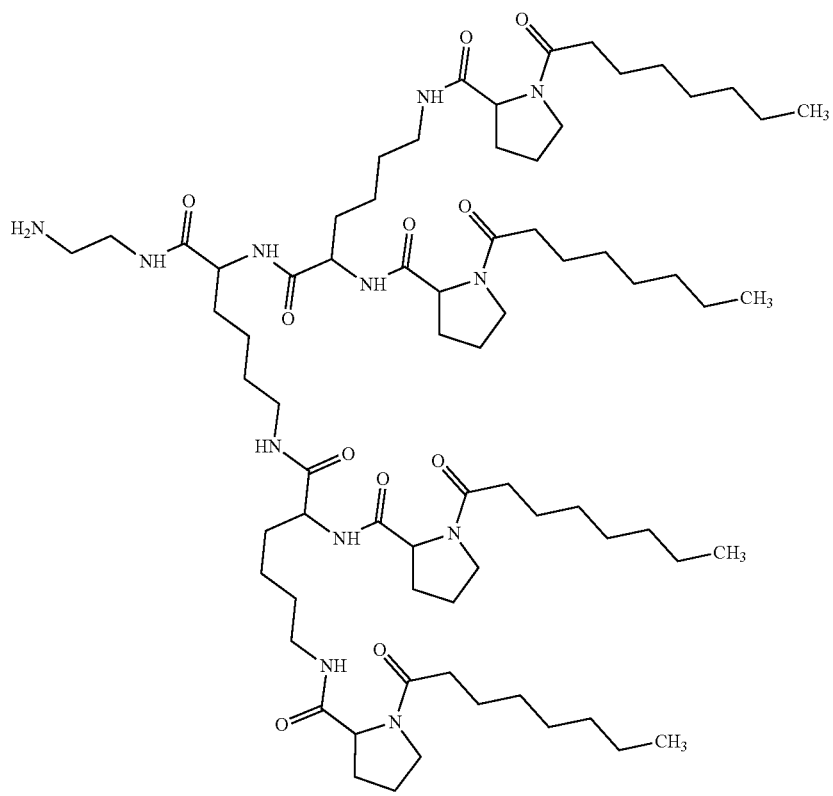 [SMILES: CCCCCCCC(=O)N1CCCC1C(=O)NCCCCC(NC(=O)C1CCCN1C(=O)CCCCCCC)C(=O)NCCCCC(NC(=O)C(CCCCNC(=O)C1CCCN1C(=O)CCCCCCC)NC(=O)C1CCCN1C(=O)CCCCCCC)C(=O)NCCN] |

-continued
| No. | INTERMEDIATE HYDROPHOBIC COMPOUNDS |
|---|---|
| A11 | 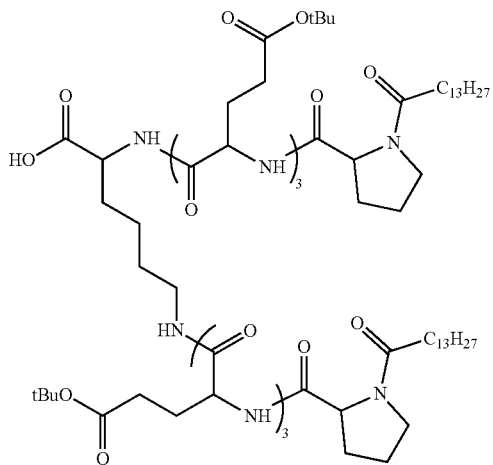 |
| A12 | 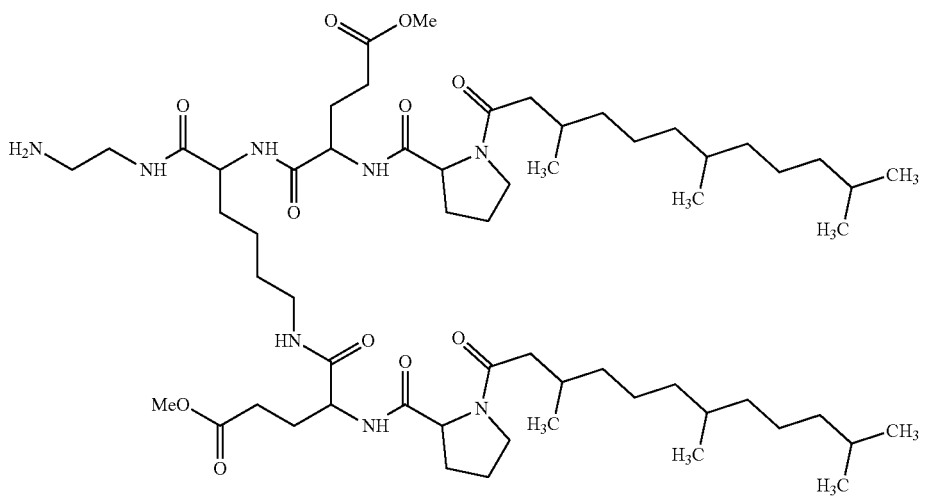 [SMILES: COC(=O)CCC(NC(=O)C1CCCN1C(=O)CC(C)CCCC(C)CCCC(C)C)C(=O)NCCCCC(NC(=O)C(CCC(=O)OC)NC(=O)C1CCCN1C(=O)CC(C)CCCC(C)CCCC(C)C)C(=O)NCCN] |
| A13 | 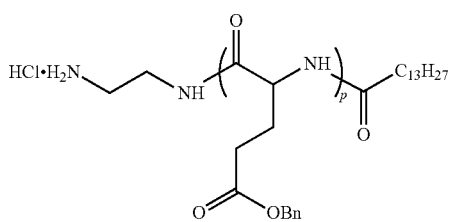
DP (p) = 5,2 |
| A14 | 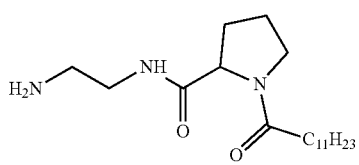 |

| No. | INTERMEDIATE HYDROPHOBIC COMPOUNDS |
|---|---|
| A15 | 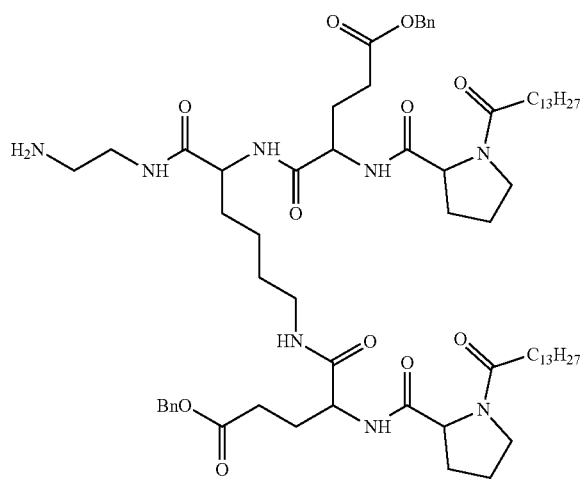 |
| A16 | 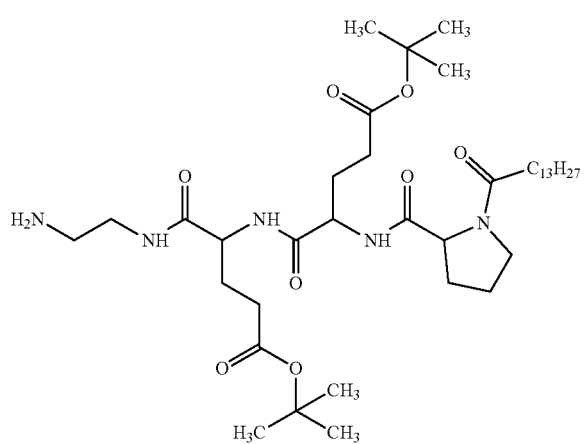 |
| A17 | 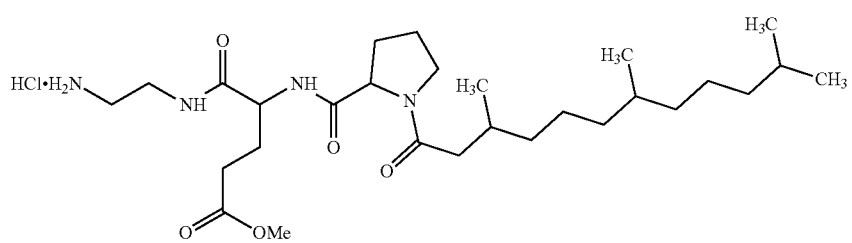 |
| A18 | 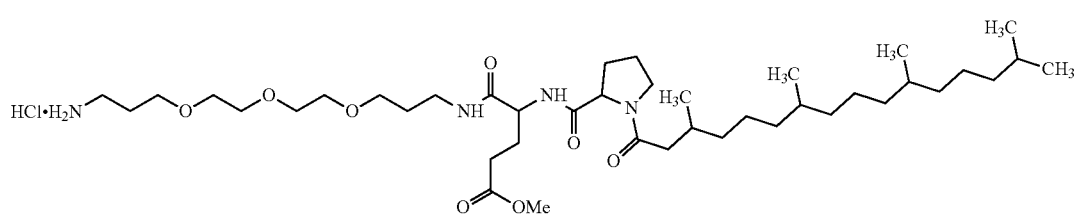 |

| No. | INTERMEDIATE HYDROPHOBIC COMPOUNDS |
|---|---|
| A19 | 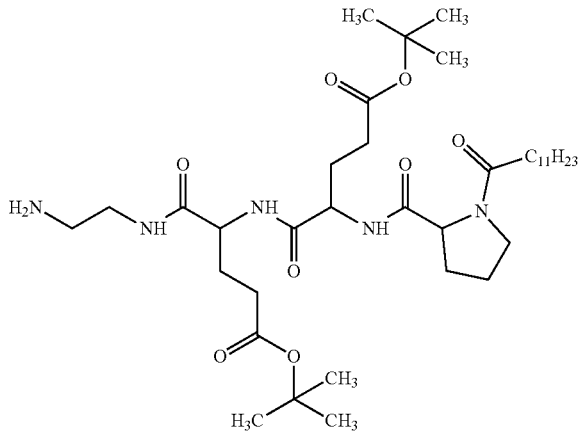 |
| A20 | 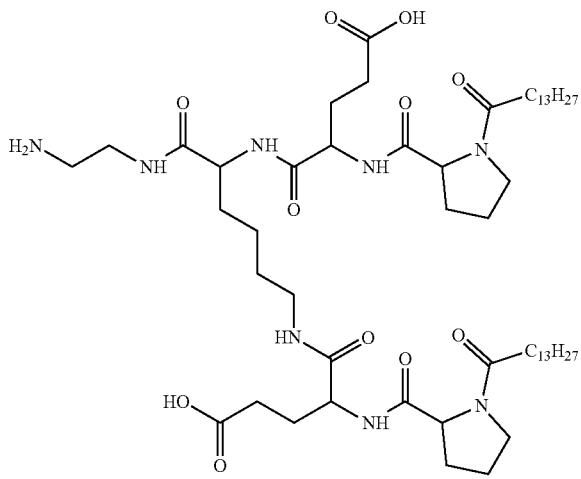 |

Example A1: Molecule A1

Molecule 1: Product Obtained by the Reaction Between Fmoc-Lys (Fmoc)-OH and the 2-C1-Trityl Chloride Resin.

To a suspension of Fmoc-Lys (Fmoc)-OH (7.32 g, 12.40 mmol) in dichloromethane (60 mL) at room temperature is added DIPEA (4.32 mL, 24.80 mmol). After complete solubilization (10 min), the solution obtained is poured onto the 2-Cl-trityl chloride resin, previously washed with dichloromethane (100-200 mesh, 1% DVB, 1.24 mmol/g) (4.00 g, 4.96 mmol), in a reactor adapted for peptide synthesis on a solid medium. After stirring for 2 hours at room temperature, HPLC grade methanol (0.8 mL/g resin, 3.2 mL) is added and the medium is stirred at room temperature for 15 min. The resin is filtered, washed successively with dichloromethane (3×60 mL), DMF (2×60 mL), dichloromethane (2×60 mL), isopropanol (1×60 mL) and dichloromethane (3×60 mL).

Molecule 2: Product Obtained by the Reaction Between Molecule 1 and an 80:20 DMF/Piperidine Mixture.

Molecule 1, previously washed with DMF, is treated with an 80:20 DMF/piperidine mixture (60 mL). After stirring for 30 minutes at room temperature, the resin is filtered, washed successively with DMF (3×60 mL), isopropanol (1×60 mL) and dichloromethane (3×60 mL).

Molecule 3: Product Obtained by the Reaction Between Molecule 2 and a Fmoc-Glu (OtBu)-OH.

DIPEA (8.64 mL, 49.60 mmol) is added to a suspension of Fmoc-Glu (OtBu)-OH (10.55 g, 24.80 mmol) and 1-[bis(dimethylamino)methylene]-1H-1,2,3-triazolo[4,5-b]pyridinium 3-oxide hexafluorophosphate (HATU, 9.43 g, 24.80 mmol) in a 1:1 DMF/dichloromethane mixture (60 mL) mixture. After complete solubilization, the solution obtained is poured onto molecule 2. After stirring for 2 hours at room temperature, the resin is filtered, washed successively with DMF (3×60 mL), isopropanol (1×60 mL) and dichloromethane (3×60 mL).

Molecule 4: Product Obtained by the Reaction Between Molecule 3 and a 50:50 DMF/Morpholine Mixture.

Molecule 3, previously washed with DMF, is treated with a 50:50 DMF/morpholine mixture (60 mL). After stirring for 1 hour 15 minutes at room temperature, the resin is filtered, washed successively with DMF (3×60 mL), isopropanol (1×60 mL) and dichloromethane (3×60 mL).

Molecule 5: Product Obtained by the Reaction Between Molecule 4 and Molecule 11.

Molecule 5 is obtained using a process similar to the one used for molecule 3, applied to molecule 4 and molecule 11 (8.07 g, 24.80 mmol) in DMF (60 mL).

Molecule 6: Product Obtained by the Reaction Between the Molecule 5 and an 80:20 Dichloromethane/1,1,1,3,3,3-Hexafluoro-2-Propanol (HFIP) Mixture.

Molecule 5 is treated with an 80:20 dichloromethane/1,1,1,3,3,3-hexafluoro-2-propanol (HFIP) mixture (60 mL). After stirring for 20 minutes at room temperature, the resin is filtered and washed with dichloromethane (2×60 mL). The solvents are evaporated under reduced pressure. Two co-evaporations are then carried out on the residue with dichloromethane (60 mL) then diisopropyl ether (60 mL). The product is purified by chromatography on silica gel (dichloromethane, methanol). A white solid of molecule 6 is obtained.

Yield: 2.92 g (52% in 6 steps)

RMN $^1$H (CD$_3$OD, ppm): 0.90 (6H); 1.22-2.47 (88H); 3.13-3.25 (2H); 3.45-3.76 (4H); 4.24-4.55 (5H).

LC/MS (ESI+): 1131.9 (calculated ([M+H]$^+$): 1131.8).

Molecule 7: Product Obtained by the Reaction Between Molecule 6 and N-Boc Ethylenediamine.

To a solution of molecule 6 (2.82 g, 2.49 mmol) in Me-THF (20 mL) at room temperature are successively added N-hydroxy benzotriazole (HOBt, 496 mg, 3.24 mmol) and N-Boc ethylenediamine (BocEDA, 440 mg, 2.74 mmol). The mixture is cooled to 0° C., then (3-dimethylaminopropyl)-N'-ethyl carbodiimide (EDC, 621 mg, 3.24 mmol) is added. The reaction medium is stirred for 15 min at 0° C., then 18 hours at room temperature. The organic phase is diluted with dichloromethane (30 mL) and washed with an aqueous solution saturated in NH$_4$Cl (2×20 mL), an aqueous solution saturated in NaHCO$_3$ (2×20 mL), and an aqueous solution saturated in NaCl (2×20 mL). The organic phase is dried over Na2SO4, filtered and concentrated under reduced pressure. A white solid of molecule 7 is obtained after recrystallization in acetonitrile.

Yield: 2.47 g (78%)

RMN $^1$H (CDCl$_3$, ppm): 0.87 (6H); 1.09-1.77 (77H); 1.84-2.49 (20H); 2.99-3.83 (10H); 4.16-4.25 (1H); 4.27-4.47 (4H); 5.68 (0.1H); 5.95-6.08 (0.9H); 6.91-7.14 (2H); 7.43-7.57 (1H); 7.68-7.78 (1H); 8.22-8.35 (1H).

LC/MS (ESI+): 1273.9 (calculated ([M+H]$^+$): 1273.9).

Molecule A1

To a solution of molecule 7 (2.47 g, 1.94 mmol) in dichloromethane (20 mL) at room temperature is added a solution of HCl 4 N in dioxane (7.27 mL), then the medium is stirred for 16 hours at room temperature. After concentration under reduced pressure, coevaporation and washing with diisopropyl ether, a white solid of molecule A1 in the form of HCl salt is obtained. This solid is solubilized in water (100 mL) then the pH is adjusted to 7 by adding an aqueous solution of NaOH 1 N. The solution is lyophilized then the lyophilizate is dried by coevaporation in toluene. A white solid of molecule A1 is obtained.

Yield: 1.64 g (80%)

RMN $^1$H (D$_2$O, ppm): 0.90 (6H); 1.15-2.59 (70H); 3.06-3.86 (10H); 4.19-4.43 (5H).

LC/MS (ESI+): 1061.8 (calculated ([M+H]$^+$): 1061.8).

Example A2: Molecule A2

Molecule 8: Product Obtained by Coupling Between Myristic Acid and Methyl L-Glutamate.

To a solution of myristic acid (35.0 g, 153.26 mmol) in tetrahydrofuran (THF, 315 mL) at 0° C. are successively added N-hydroxysuccinimide (NHS, 17.81 g, 154 g). 79 mmol) and N,N-dicyclohexylcarbodiimide (DCC, 31.94 g, 154.79 mmol). The medium is stirred for 48 hours while raising the temperature to room temperature, sinter filtered, then added to a solution of methyl L-glutamate (24.95 g, 154.79 mmol) and N,N-diisopropylethylamine (DIPEA, 99.0 g, 766.28 mmol) in water (30 mL). The reaction mixture is stirred at 20° C. for 48 hours, then concentrated under reduced pressure. Water (200 mL) is added and the mixture obtained is treated by successive addition of ethyl acetate (AcOEt, 100 mL) then a 5% aqueous solution of Na$_2$CO$_3$%(50 mL). The aqueous phase is then washed again in AcOEt (100 mL), acidified by adding an aqueous solution of 10% HCl and the product is extracted with dichloromethane (DCM, 3×150 mL). The organic phase is dried over Na$_2$SO$_4$, filtered and concentrated under reduced pressure. A white solid of molecule 8 is obtained.

Yield: 47.11 g (84%)

RMN $^1$H (CDCl$_3$, ppm): 0.87 (3H); 1.07-1.66 (22H); 2.02-2.11 (1H); 2.18-2.36 (3H); 2.39-2.47 (1H); 2.50-2.58 (1H); 3.69 (3H); 4.54-4.59 (1H); 6.62 (1H); 8.26 (1H).

LC/MS (ESI+): 372.2 (calculated ([M+H]$^+$): 372.3).

Molecule 9: Product Obtained by Coupling Between Molecule 8 and L-Methyl Glutamate.

Using a process similar to the one used for the preparation of molecule 8 and applied to molecule 8 (35.0 g, 94.21 mmol) and to L-methyl glutamate (15.33 g, 95.15 mmol), a white solid of molecule 9 is obtained after recrystallization in acetonitrile.

Yield: 24.0 g (49%)

RMN $^1$H (DMSO-d6, ppm): 0.85 (3H); 1.06-1.51 (22H); 1.70-1.94 (3H); 1.96-2.15 (3H); 2.29-2.40 (4H); 3.58 (3H); 3.58 (3H); 4.16-4.22 (1H); 4.25-4.32 (1H); 7.93 (1H); 8.16 (1H); 12.66 (1H).

LC/MS (ESI+): 515.3 (calculated ([M+H]$^+$): 515.3).

Molecule 10: Product Obtained by Coupling Between Molecule 9 and N-Boc Ethylenediamine.

To a suspension of molecule 9 (24.0 g, 46.63 mmol) in DCM (285 mL) at 0° C. are successively added HOBt (714 mg, 46.66 mmol), BocEDA (8.97 g, 55.96 mmol) in solution in DCM (25 mL) then EDC (9.83 g, 51.30 mmol). The reaction medium is stirred for 1 hour at 0° C., then 18 hours at room temperature. The organic phase is washed with an aqueous solution saturated in NaHCO$_3$ (2×300 mL), an aqueous solution of 1 N HCl (2×300 mL), and an aqueous solution saturated in NaCl (500 mL). Methanol (40 ml) is added, the organic phase is dried over Na2SO4, filtered and concentrated under reduced pressure. A white solid of molecule 10 is obtained after recrystallization in acetonitrile.

Yield: 27.15 g (89%)

RMN $^1$H (CDCl$_3$, ppm): 0.87 (3H); 1.07-1.68 (22H); 1.42 (9H); 1.97-2.18 (4H); 2.22-2.31 (2H); 2.35-2.55 (4H); 3.19-3.29 (2H); 3.30-3.38 (2H); 3.66 (3H); 3.68 (3H); 4.34-4.41 (1H); 4.42-4.48 (1H); 5.54 (1H); 6.99-7.18 (2H); 7.56 (1H).

LC/MS (ESI+): 657.4 (calculated ([M+H]$^+$): 657.4).

Molecule A2

To a solution of molecule 10 (27.15 g, 41.33 mmol) in a mixture of DCM/methanol (410 mL) at 0° C. is added a solution of HCl 4 N in dioxane (51.7 mL), then the medium is stirred for 2 hours at 0° C., then for 16 hours at room temperature. After concentration under reduced pressure and coevaporation in methanol (2×150 mL), a white solid of molecule A2 in the form of a chloride salt is obtained, after recrystallization in acetonitrile.

Yield: 23.2 g (95%)

RMN $^1$H (DMSO-d6, ppm): 0.85 (3H); 1.05-1.52 (22H); 1.71-1.85 (2H); 1.87-2.03 (2H); 2.07-2.18 (2H); 2.24-2.37 (4H); 2.84 (2H); 3.24-3.38 (2H); 3.58 (3H); 3.58 (3H); 4.17-4.24 (2H); 7.95-8.08 (1H); 8.14 (1H).

LC/MS (ESI+): 557.3 (calculated ([M+H]$^+$): 557.4).

Example A3: Molecule A3

Molecule 11: Product Obtained by Coupling Between Myristoyl Chloride and L-Proline.

To a solution of L-proline (300.40 g, 2.61 mol) in 2 N aqueous sodium (1.63 L) at 0° C. is slowly added over 1 hour myristoyl chloride (322 g, 1.30 mol) dissolved in dichloromethane (DCM, 1.63 L). At the end of this addition, the reaction medium is raised to 20° C. over 3 h, then stirred for 2 additional hours. The mixture is cooled to 0° C. then an aqueous solution of 37% HCl %(215 mL) is added over 15 minutes. The reaction medium is stirred for 1 hour from 0° C. to 20° C. The organic phase is separated, washed with an aqueous solution of 10% HCl %(3×430 mL), an aqueous solution saturated in NaCl (430 mL), dried over Na2SO4, filtered through cotton, then concentrated under reduced pressure. The residue is solubilised in heptane (1.31 L) at 50° C., then the solution is progressively returned to room temperature. After priming the crystallization with a glass rod, the medium is again heated to 40° C. for 30 minutes then returned to room temperature over 4 hours. A white solid is obtained after sintered filtration, washing with heptane (2×350 mL) and drying under reduced pressure.

Yield: 410 g (97%)

RMN $^1$H (CDCl$_3$, ppm): 0.88 (3H); 1.28 (20H); 1.70 (2H); 1.90-2.10 (3H); 2.36 (2H); 2.51 (1H); 3.47 (1H); 3.56 (1H); 4.61 (1H).

LC/MS (ESI): 326.4; 651.7 (calculated ([M+H]$^+$): 326.3; ([2 M+H]$^+$): 651.6).

Molecule 12: Product Obtained by Coupling Between Molecule 11 and Methyl L Glutamate.

Using a process similar to the one used for the preparation of molecule 8 and applied to molecule 11 (30.0 g, 92.17 mmol) and to methyl L-glutamate (15.60 g, 96.78 mmol), a white solid of molecule 12 is obtained after solubilisation in refluxing acetone, cooling to room temperature and sintered filtration. The filtrate is evaporated and the residue is precipitated in acetone as above, this operation being repeated 3 times.

Yield: 15.5 g (36%)

RMN $^1$H (DMSO-d6, ppm): 0.85 (3H); 1.07-1.37 (20H); 1.40-1.50 (2H); 1.71-2.27 (8H); 2.30-2.40 (2H); 3.28-3.54 (2H); 3.58 (1.3H); 3.59 (1.7H); 4.14-4.28 (1H); 4.28-4.37 (1H); 8.06 (0.55H); 8.33 (0.45H); 12.64 (1H).

LC/MS (ESI+): 469.2 (calculated ([M+H]$^+$): 469.3).

Molecule 13: Product Obtained by Coupling Between Molecule 12 and N-Boc Ethylenediamine.

Using a process similar to the one used for the preparation of molecule 10 and applied to molecule 12 (15.5 g, 33.05 mmol) and to BocEDA (5.83 g, 36.36 mmol), a white solid of molecule 13 is obtained after recrystallization in acetonitrile.

Yield: 19.8 g (83%)

RMN $^1$H (DMSO-d6, ppm): 0.85 (3H); 1.07-1.55 (22H); 1.37 (9H); 1.69-2.19 (7H); 2.22-2.36 (3H); 2.91-3.17 (4H); 3.28-3.60 (5H); 4.11-4.18 (0.7H); 4.20-4.28 (1H); 4.38-4.42 (0.3H); 6.74 (1H); 7.64 (0.7H); 7.87 (0.7H); 7.98 (0.3H); 8.22 (0.3H).

LC/MS (ESI+): 611.4 (calculated ([M+H]$^+$): 611.4).

Molecule A3

Using a process similar to the one used for the preparation of molecule A2 and applied to molecule 13 (16.8 g, 27.50 mmol) a white solid of molecule A3 in the form of a hydrochloride salt is obtained after recrystallization in acetonitrile.

Yield: 13.5 g (90%)

RMN $^1$H (DMSO-d6, ppm): 0.85 (3H); 1.08-1.52 (22H); 1.70-2.37 (10H); 2.80-2.90 (2H); 3.22-3.62 (4H); 3.57 (3H); 4.15-4.28 (1.75H); 4.41-4.44 (0.25H); 7.81-8.13 (4.5H); 8.24-8.29 (0.25H); 8.33-8.39 (0.25H).

LC/MS (ESI+): 511.3 (calculated ([M+H]$^+$): 511.4).

Example A4: Molecule A4

Molecule 14: Product Obtained by Coupling Between Lauroyl Chloride and L-Proline Using a process similar to the one used for the preparation of molecule 11 and applied to lauroyl chloride (27.42 g, 685.67 mmol) and to L-proline (60.0 g, 247.27 mmol), a white solid of molecule 14 is obtained.

Yield: 78.35 g (96%)

RMN $^1$H (CDCl$_3$, ppm): 0.87 (3H); 1.26 (16H); 1.70 (2H); 1.90-2.10 (3H); 2.35 (2H); 2.49 (1H); 3.48 (1H); 3.56 (1H); 4.60 (1H).

LC/MS (ESI+): 298.1 (calculated ([M+H]$^+$): 298.2).

Molecule 15: Product Obtained by Coupling Between Molecule 14 and Methyl L-Glutamate.

Using a process similar to the one used for the preparation of molecule 8 and applied to molecule 14 (34.64 g, 116.46 mmol) and to methyl L-glutamate (19.14 g, 118.79 mmol), a white solid of molecule 15 is obtained after recrystallization in acetonitrile.

Yield: 37.28 g (73%)

RMN $^1$H (CDCl$_3$, ppm): 0.85 (3H); 1.08-1.42 (16H); 1.54-1.06 (2H); 1.80-2.47 (10H); 3.42-3.80 (2H); 3.65 (2.55H); 3.67 (0.45H); 4.37-4.40 (0.15H); 4.51-4.58 (0.85H); 4.58-4.67 (1H); 7.26 (0.15H); 7.65 (0.85H); 8.06 (1H).

LC/MS (ESI+): 441.1 (calculated ([M+H]$^+$): 441.3).

Molecule 16: Product Obtained by Coupling Between Molecule 15 and N-Boc Ethylenediamine.

Using a process similar to the one used for the preparation of molecule 10 and applied to molecule 15 (37.30 g, 84.66 mmol) and to BocEDA (14.92 g, 93.13 mmol), a white solid of molecule 16 is obtained after recrystallization in acetonitrile.

Yield: 43.10 g (87%)

RMN $^1$H (DMSO-d6, ppm): 0.85 (3H); 1.08-1.53 (18H); 1.37 (9H); 1.70-2.36 (10H); 2.91-3.60 (9H); 4.11-4.18 (0.7H); 4.21-4.28 (1H); 4.38-4.42 (0.3H); 6.38 (0.1H); 6.74 (0.9H); 7.65 (0.7H); 7.87 (0.7H); 7.99 (0.3H); 8.22 (0.3H).

LC/MS (ESI+): 583.4 (calculated ([M+H]$^+$): 583.4).

Molecule A4

Using a process similar to the one used for the preparation of molecule A2 and applied to molecule 16 (43.10 g, 73.96 mmol) a white solid of molecule A4 in the form of a hydrochloride salt is obtained after recrystallization in acetonitrile.

Yield: 31.90 g (83%)

RMN $^1$H (DMSO-d6, ppm): 0.85 (3H); 1.05-1.37 (16H); 1.39-1.52 (2H); 1.70-2.37 (10H); 2.29-2.91 (2H); 3.20-3.62 (7H); 4.16-4.29 (1.7H); 4.42-4.46 (0.3H); 7.86-8.18 (4.6H); 8.32 (0.3H); 8.40 (0.3H).

LC/MS (ESI+): 483.2 (calculated ([M+H]$^+$): 483.3).

Example A5: Molecule A5

Molecule 17: Product Obtained by the Reaction Between 1-Amino-4,7,10-Trioxa-13-Tridecane Amine and Tert-Butyl Phenyl Carbonate.

To a solution of 1-amino-4,7,10-trioxa-13-tridecane amine (112.29 g, 509.71 mmol) in ethanol (510 mL) at 80° C. is added, drop by drop, tert-butyl phenyl carbonate (49.50 g, 254.86 mmol). The reaction medium is stirred at 80° C.

for 3 hours 30 minutes, then concentrated under reduced pressure. The residue is solubilized in water (250 mL), the pH is adjusted to 2.3 with a 37% HCl solution and the mixture is extracted with methyl tert-butyl ether (MTBE, 2×150 mL). The aqueous phase is basified to pH 12.6 by adding a 2 N NaOH solution and extracted with DCM (3×250 mL). The organic phase is washed with an aqueous solution of NaOH 1 N (1×100 mL), an aqueous solution saturated in NaCl (100 mL), dried over Na2SO4, filtered and concentrated under reduced pressure. A yellow oil of molecule 17 is obtained.

Yield: 54.4 g (67%)

RMN $^1$H (CDCl$_3$, ppm): 1.40-1.58 (11H); 1.73-1.81 (4H); 2.80-2.84 (2H); 3.20-3.70 (14H); 5.11 (1H).

LC/MS (ESI+): 321.2 (calculated ([M+H]$^+$): 321.2).

Molecule 18: Product Obtained by Coupling Between Molecule 12 and Molecule 17.

Using a process similar to the one used for the preparation of molecule 10 and applied to molecule 12 (20.46 g, 43.66 mmol) and molecule 17 (16.79 g, 52.39 mmol), a white wax of molecule 18 is obtained after purification by flash chromatography (eluent: DCM, methanol), solubilization of the residue in DCM (300 mL), washes of the organic phase with an aqueous solution of NaHCO$_3$ (2×150 mL), a 10% HCl aqueous solution (2×150 mL), an aqueous solution saturated in NaCl (2×150 mL), drying over Na$_2$SO$_4$ and concentration under reduced pressure.

Yield: 30.15 g (90%)

RMN $^1$H (DMSO-d6, ppm): 0.85 (3H); 1.09-1.52 (31H); 1.55-1.67 (4H); 1.69-2.36 (10H); 2.91-2.98 (2H); 3.02-3.17 (2H); 3.28-3.61 (17H); 4.12-4.17 (0.7H); 4.20-4.28 (1H); 4.39-4.42 (0.3H); 6.37 (0.1H); 6.71 (0.9H); 7.59 (0.7H); 7.85 (0.7H); 7.94 (0.3H); 8.21 (0.3H).

LC/MS (ESI+): 771.4 (calculated ([M+H]$^+$): 771.5).

Molecule A5

Using a process similar to the one used for the preparation of molecule A2 and applied to molecule 18 (30.0 g, 38.91 mmol) a white solid of molecule A5 in the form of a hydrochloride salt is obtained after solubilization of the residue in water (500 mL) and lyophilization.

Yield: 25.2 g (91%)

RMN $^1$H (DMSO-d6, ppm): 0.85 (3H); 1.06-1.37 (20H); 1.39-1.52 (2H); 1.58-1.66 (2H); 1.70-2.37 (12H); 2.78-2.85 (2H); 3.01-3.15 (2H); 3.31-3.62 (17H); 4.11-4.17 (0.7H); 4.19-4.27 (1H); 4.41-4.44 (0.3H); 7.63-7.71 (0.7H); 7.90-8.24 (4H); 8.28-8.35 (0.3H).

LC/MS (ESI+): 671.4 (calculated ([M+H]$^+$): 671.5).

Example A7: Molecule A7

Molecule 21: Product Obtained by Coupling Between Molecule 11 and L-Lysine.

Using a process similar to the one used for the preparation of molecule 8 and applied to molecule 11 (133.00 g, 408.61 mmol) and to L-lysine (31.36 g, 214.52 mmol), a white solid of molecule 21 is obtained after crystallization twice in acetone.

Yield 106.50 g (68%)

RMN $^1$H (DMSO-d$_6$, ppm): 0.85 (6H); 1.26 (40H); 1.35-1.50 (6H); 1.50-2.10 (10H); 2.10-2.25 (4H); 3.01 (2H); 3.31-3.55 (4H); 4.10-4.40 (3H); 7.68 (0.6H); 7.97 (1H); 8.27 (0.4H); 12.50 (1H).

LC/MS (ESI): 761.8; (calculated ([M+H]$^+$): 762.1).

Molecule 22: Product Obtained by Coupling Between Molecule 21 and N-Boc-Methyl L-Lysinate.

Using a process similar to the one used for the preparation of molecule 10 and applied to molecule 21 (43.00 g, 56.50 mmol) in solution in THF and to N-Boc-methyl L-lysinate hydrochloride (20.12 g, 67.79 mmol), a transparent solid of molecule 22 is obtained and used without any additional purification.

Yield: 55.80 g (98%)

RMN $^1$H (DMSO-d6, ppm): 0.86 (6H); 1.08-2.03 (64H); 1.37 (9H); 2.07-2.30 (4H); 2.84-3.09 (4H); 3.29-3.57 (4H); 3.58-3.65 (3H); 4.14-4.43 (4H); 6.40 (0.1H); 6.74 (0.9H); 7.69 (0.6H); 7.82 (0.6H); 7.95-8.06 (1H); 8.11-8.20 (0.4H); 8.26 (0.4H).

LC/MS (ESI): 1003.8 (calculated ([M+H]$^+$): 1003.8).

Molecule 23: Product Obtained by Saponification of Molecule 23.

A solution of molecule 22 (55.80 g, 55.61 mmol) in a 1:1 THF/water mixture (370 mL) at 0° C. is treated with the slow addition of a solution of LiOH (2.00 g, 83.41 mmol) in water (185 mL). After 16 hours of stirring at 0° C., the medium is concentrated under reduced pressure and the residue is redissolved in water (500 mL). DCM (500 mL) is added, the heterogeneous mixture is cooled to 10° C. and acidified by adding a 10% aqueous solution of HCl up to pH 1. The aqueous phase is extracted with DCM (2×300 mL), and the combined organic phases are washed with an aqueous solution saturated in NaCl (2×300 mL), dried over Na2SO4, filtered and concentrated under reduced pressure. A white solid of molecule 23 is obtained after crystallization in acetone.

Yield: 46.10 g (84%)

RMN $^1$H (pyridine-d6, ppm): 0.85 (6H); 1.05-2.03 (67H); 2.07-2.61 (10H); 3.12-3.93 (8H); 4.54-4.93 (2H); 4.98-5.16 (2H); 7.35-7.45 (1H); 8.34-8.63 (1H); 8.94-9.41 (2H).

LC/MS (ESI): 989.8 (calculated ([M+H]$^+$): 989.8).

Molecule A7

To a solution of molecule 23 (12.00 g, 12.13 mmol) in dichloromethane (40 mL) at 0° C. is added a solution of HCl 4 N in dioxane (15.20 mL), then the medium is stirred for 15 hours at 0° C. and 5 hours at room temperature. The reaction mixture is concentrated under reduced pressure, the residue is solubilized in a mixture of DCM (120 mL) and NaOH 2 N (60 mL). After separation of the phases, the organic phase is washed with a solution of NaOH 2 N (60 mL), dried with Na$_2$SO$_4$ and concentrated under reduced pressure.

Yield: 10.90 g (98%)

RMN $^1$H (DMSO-d6, ppm): 0.86 (6H); 1.05-2.27 (70H); 2.45-2.52 (2H); 2.90-3.58 (6H); 3.67-3.76 (1H); 4.02-4.10 (0.6H); 4.11-4.17 (0.4H); 4.20-4.26 (0.6H); 4.30-4.39 (1H); 4.42-4.46 (0.4H); 7.29-7.42 (1H); 7.71-7.80 (0.6H); 7.97-8.05 (0.6H); 8.10-8.24 (0.4H); 8.33-8.45 (0.4H).

LC/MS (ESI): 887.7 (calculated ([M−H]$^−$): 887.7).

Example A5a: Molecule A5a

Molecule 3a: Product Obtained by the Reaction Between Fmoc-Lys(Fmoc)-OH and the 2-Cl-Trityl Chloride Resin.

To a suspension of Fmoc-Lys(Fmoc)-OH (7.32 g, 12.40 mmol) in DCM (60 mL) at room temperature is added DIPEA (4.32 mL, 24.80 mmol). After complete solubilization (10 min), the solution obtained is poured onto the 2-Cl-trityl chloride resin (100-200 mesh, 1% DVB, 1.24 mmol/g) (4.00 g, 4.96 mmol), previously washed with DCM, in a reactor used for peptide synthesis on a solid medium. After stirring for 2 hours at room temperature, HPLC grade methanol (0.8 mL/g resin, 3.2 mL) is added and the medium is stirred at room temperature for 15 minutes. The resin is filtered, washed successively with DCM (3×60 mL), DMF (2×60 mL), DCM (2×60 mL), isopropanol (1×60 mL) and DCM (3×60 mL).

Molecule 4a: Product Obtained by the Reaction Between Molecule 3a and an 80:20 DMF/Piperidine Mixture.

Molecule 3a, previously washed with DMF, is treated with an 80:20 DMF/piperidine mixture (60 mL). After stirring for 30 minutes at room temperature, the resin is filtered, washed successively with DMF (3×60 mL), isopropanol (1×60 mL) and DCM (3×60 mL).

Molecule 5a: Product Obtained by Reaction Between Molecule 4a and 8-(9-Fluorenylmethyloxycarbonyl-Amino)-3,6-Dioxaoctanoic Acid (Fmoc-O2Oc-OH).

To a suspension of Fmoc-O2Oc-OH (9.56 g, 24.80 mmol) and 1-[bis(dimethylamino)methylene]-1H-1,2,3-triazolo[4,5-b]pyridinium 3-oxide hexafluorophosphate (HATU, 9.43 g, 24.80 mmol) in a 1:1 DMF/DCM mixture (60 mL) is added DIPEA (8.64 mL, 49.60 mmol). After complete solubilisation, the solution obtained is poured onto molecule 4a. After stirring for 2 hours at room temperature, the resin is filtered, washed successively with DMF (3×60 mL), isopropanol (1×60 mL) and dichloromethane (3×60 mL).

Molecule 6a: Product Obtained by Reaction Between Molecule 5a and an 80:20 DMF/Piperidine Mixture.

Using a process similar to the one used for molecule 4a, applied to molecule 5a, molecule 6a is obtained.

Molecule 7a: Product Obtained by Reaction Between Molecule 6a and Lauric Acid.

Using a process similar to the one used for molecule 5a, applied to molecule 6a and lauric acid (4.97 g, 24.80 mmol) in DMF (60 mL), molecule 7a is obtained.

Molecule 8a: Product Obtained by Reaction Between Molecule 7a and an 80:20 Dichloromethane/1,1,1,3,3,3-Hexafluoro-2-Propanol (HFIP) Mixture.

Molecule 7a is treated with an 80:20 dichloromethane/1,1,1,3,3,3-hexafluoro-2-propanol (HFIP) mixture (60 mL). After stirring for 20 minutes at room temperature, the resin is filtered and washed with dichloromethane (2×60 mL). The solvents are evaporated under low pressure. Two co-evaporations are then carried out on the residue with dichloromethane (60 mL) then diisopropyl ether (60 mL). A white solid of molecule 8a is obtained after recrystallization in acetonitrile.

Yield: 2.63 g (66% in 6 steps)

RMN $^1$H (CDCl$_3$, ppm): 0.87 (6H); 1.09-1.66 (40H); 1.77-1.98 (2H); 2.13-2.29 (4H); 3.24-3.75 (18H); 3.95-4.07 (4H); 4.65-4.70 (1H); 6.23-6.37 (1H); 6.39-6.62 (1H); 6.74-6.91 (1H); 7.38-7.54 (1H).

LC/MS (ESI): 801.6 (calculated ([M+H]$^+$): 801.6).

Molecule 9a: Product Obtained by Reaction Between Molecule 8a and N-Boc Ethylenediamine.

To a solution of molecule 8a (2.63 g, 3.29 mmol) in chloroform (20 mL) at room temperature are successively added HOBt (654 mg, 4.27 mmol) and BocEDA (580 mg, 3.62 mmol). The mixture is cooled to 0° C., then EDC (819 mg, 4.27 mmol) is added. The reaction medium is stirred for 15 min at 0° C., then 18 hours at room temperature. The organic phase is washed with an aqueous solution saturated in NH$_4$Cl (2×10 mL), an aqueous solution saturated in NaHCO$_3$ (2×10 mL), and an aqueous solution saturated in NaCl (2×10 mL). The organic phase is dried over Na$_2$SO$_4$, filtered and concentrated under reduced pressure. A white solid of molecule 9a is obtained after purification by chromatography on silica gel (eluent: dichloromethane, methanol).

Yield: 2.37 g (76%)

RMN $^1$H (CDCl$_3$, ppm): 0.87 (6H); 1.08-1.47 (34H); 1.43 (9H); 1.48-1.70 (7H); 1.78-1.87 (1H); 2.14-2.25 (4H); 3.16-3.71 (22H); 3.92-4.04 (4H); 4.47-4.52 (1H); 5.33 (1H); 6.10 (1H); 6.65-7.01 (1H); 7.11-7.30 (2H); 7.47-7.63 (1H).

Molecule A5a

To a solution of molecule 9a (2.37 g, 2.51 mmol) in dichloromethane (50 mL) at room temperature is added a solution of HCl 4 in dioxane (6.3 mL), then the medium is stirred for 2 hours at room temperature. After concentration under reduced pressure, the residue is solubilized in dichloromethane (50 mL) then washed with an aqueous solution of NaOH 1 N (2×12.5 mL) and an aqueous solution saturated in NaCl (25 mL). The organic phase is dried over Na$_2$SO$_4$, filtered and concentrated under reduced pressure. A white solid of molecule A5a is obtained after recrystallization in acetonitrile.

Yield: 1.57 g (74%)

RMN $^1$H (CDCl$_3$, ppm): 0.87 (6H); 1.08-1.43 (34H); 1.48-1.71 (7H); 1.74-1.93 (3H); 2.14-2.25 (4H); 2.79-2.86 (2H); 3.17-3.71 (20H); 3.93-4.05 (4H); 4.47-4.54 (1H); 6.08-6.29 (1H); 6.84-7.01 (1H); 7.15-7.32 (2H); 7.50-7.64 (1H).

LC/MS (ESI): 843.6 (calculated ([M+H]$^+$): 843.7).

Example A6a: Molecule A6a

Molecule 10a: Product Obtained by Hydrogenation of Retinoic Acid.

A solution of retinoic acid (19.0 g, 63.24 mmol) in methanol (450 mL) in the presence of 10% palladium on carbon (1.9 g) is placed under a hydrogen atmosphere (1 atm) at room temperature overnight. The reaction medium is sinter filtered then the filtrate is concentrated under reduced pressure. A colorless oil of molecule 10a is obtained.

Yield: 19.50 g (99%)

RMN $^1$H (CDCl$_3$, ppm): 0.45-2.01 (35H); 2.10-2.17 (1H); 2.33-2.38 (1H); 11.14 (1H).

LC/MS (ESI): 309.3 (calculated ([M−H]$^-$): 309.3).

Molecule 11a: Product Obtained by Coupling Between Boc-1-Amino-4,7,10-Trioxa-13-Tridecane Amine (Boc-TOTA) and Molecule 10a.

Using a process similar to the one used for the preparation of molecule 9a applied to molecule 10a (19.3 g, 62.15 mmol) and to BocTOTA (23.9 g, 74.58 mmol), an orange oil of molecule 11a is obtained.

Yield: 37.05 g (97%)

RMN $^1$H (CDCl$_3$, ppm): 0.43-1.71 (49H); 2.13-2.17 (1H); 3.17-3.24 (2H); 3.32-3.39 (2H); 3.51-3.66 (12H); 4.77 (0.1H); 4.94 (0.9H); 6.13 (0.9H); 6.29 (0.1H).

LC/MS (ESI): 613.5 (calculated ([M+H]$^+$): 613.5).

Molecule A6a

Using a process similar to the one used for the preparation of molecule A5$_a$, applied to molecule 11a (34.9 g, 56.94 mmol) an orange oil of molecule A6a is obtained.

Yield: 28.5 g (97%)

RMN $^1$H (CDCl$_3$, ppm): 0.41-1.96 (42H); 2.13 (1H); 2.78 (2H); 3.31-3.36 (2H); 3.53 (4H); 3.55-3.58 (4H); 3.60-3.63 (4H); 6.43 (1H).

LC/MS (ESI): 513.5 (calculated ([M+H]$^+$): 513.5).

Example A8: Molecule A8

Molecule 15a: Product Obtained by Reaction Between Decanoic Acid and L-Leucine.

Using a process similar to the one used for the preparation of molecule 8 and applied to decanoic acid (8.77 g, 50.94 mmol) and to L-leucine (7.00 g, 53.36 mmol), a white solid of molecule 15a is obtained.

Yield: 9.17 g (66%)

RMN ¹H (DMSO-d6, ppm): 0.82-0.89 (9H); 1.18-1.65 (17H); 2.04-2.14 (2H); 4.19-4.23 (1H); 7.98 (1H); 12.40 (1H).

LC/MS (ESI): 286.2 (calculated ([M+H]$^+$): 286.2).

Molecule 16a: Product Obtained by Reaction Between Molecule 15a and L-Lysine Methyl Ester.

To a solution of molecule 15a (9.16 g, 32.11 mmol) in THF (160 mL) are successively added triethylamine (8.12 g, 80.27 mmol) and 2-(1H-benzotriazole-1-yl)-1,1,3,3-tetramethyluronium tetrafluoroborate (TBTU) and the medium is stirred for 30 minutes at room temperature. L-Lysine methyl ester dihydrochloride (3.93 g, 16.86 mmol) is added to the reaction medium and stirred for 3 hours then concentrated under reduced pressure. The residue is diluted with AcOEt (200 mL), the organic phase is filtered and washed with an aqueous solution of 1 N HCl then with water, dried over Na$_2$SO$_4$, filtered and concentrated under reduced pressure. A white solid of molecule 16a is obtained after trituration of the residue in acetonitrile.

Yield: 7.33 g (66%)

RMN ¹H (DMSO-d6, ppm): 0.80-0.91 (18H); 1.06-1.72 (38H); 2.03-2.16 (4H); 2.91-3.07 (2H); 3.60 (1.15H); 3.61 (1.85H); 4.13-4.28 (2H); 4.33-4.44 (1H); 7.79-7.92 (3H); 8.13-8.26 (1H).

LC/MS (ESI) 695.7 (calculated ([M+H]$^+$): 695.6).

Molecule 17a: Product Obtained by Saponification of Molecule 16a.

To a solution of molecule 16a (7.33 g, 10.55 mmol) in a mixture of THF/methanol/water (105 mL) is added LiOH (505.13 mg, 21.09 mmol) at 0° C. then the medium is stirred for 20 hours at room temperature and concentrated under reduced pressure. The aqueous phase is acidified with a solution of 1 N HCl up to a pH of 1 and the solid formed is filtered, washed with water and dried under reduced pressure to give a white solid of molecule 17a.

Yield: 7.09 g (99%)

RMN ¹H (DMSO-d6, ppm): 0.80-0.89 (18H); 1.18-1.73 (40H); 2.03-2.16 (4H); 2.91-3.05 (2H); 4.03-4.13 (1H); 4.21-4.27 (1H); 4.31-4.40 (1H); 7.79-8.02 (4H).

LC/MS (ESI): 681.7 (calculated ([M+H]$^+$): 681.6).

Molecule 18a: Product Obtained by Reaction Between Molecule 17a and N-Boc Ethylenediamine.

Using a process similar to the one used for the preparation of molecule 16a applied to molecule 17a (7.09 g, 10.41 mmol) and to N-Boc ethylenediamine (1.83 g, 11.45 mmol), a white solid of molecule 18a is obtained after trituration in acetonitrile.

Yield: 6.64 g (77%)

RMN ¹H (DMSO-d6, ppm): 0.80-0.91 (18H); 1.15-1.73 (49H); 2.03-2.18 (4H); 2.92-3.13 (6H); 4.05-4.30 (3H); 6.71-6.83 (1H); 7.69-8.23 (5H).

LC/MS (ESI): 824.0 (calculated ([M+H]$^+$): 823.7).

Molecule A8

Using a process similar to the one used for the preparation of molecule A5a and applied to molecule 18a (3.00 g, 3.64 mmol), without basic washing, a beige solid of molecule A8 in the form of a hydrochloride salt is obtained after co-evaporation 4 times of the residue in methanol.

Yield: 2.66 g (96%)

RMN ¹H (DMSO-d6, ppm): 0.80-0.91 (18H); 1.15-1.76 (40H); 2.03-2.19 (4H); 1.78-2.89 (2H); 2.91-3.07 (2H); 3.22-3.37 (2H); 4.08-4.14 (1H); 4.17-4.28 (2H); 7.81-8.36 (8H).

LC/MS (ESI): 723.7 (calculated ([M+H]$^+$): 723.6).

Example A9: Molecule A9

Molecule 19a: 13-Methyltetradecanoic Acid.

Magnesium (5.50 g, 226.3 mmol) in shavings is introduced into a dry three-neck flask under argon. The magnesium is covered with anhydrous THF (25 mL) and a few drops of 1-bromo-2-methylpropane are added at room temperature to initiate the reaction. After observing an exotherm and a slight turbidity of the medium, the rest of the 1-bromo-2-methylpropane (28.42 g, 207 mmol) diluted in THF (60 mL) is added, drop-by-drop, during 1 hour while the medium temperature remains stable between 65 and 70° C. The reaction medium is then heated by refluxing for 2 hours.

In a three-neck flask under argon, to a solution of CuCl (280 mg, 2.83 mmol) dissolved in N-methyl pyrrolidone (NMP), previously distilled at 0° C., is added, drop-by-drop, a solution of 11-Bromo undecanoic acid (25 g, 94.27 mmol), dissolved in THF (60 mL). Then, the solution of organomagnesium slightly warm, diluted in THF (50 mL) is added, drop by drop, to this solution so as to maintain the temperature of the solution below 25° C. The mixture is then stirred at room temperature for 16 hours. The medium is cooled to 0° C. and the reaction is stopped by slow addition of an aqueous solution of 1 N HCl up to a pH of 1 (300 mL) and the medium is extracted by hexane (100 mL) and ethyl acetate (2×75 mL). After the organic phase is washed with an aqueous solution of 1 N HCl (100 mL), water (100 mL), and dried with Na$_2$SO$_4$, the solution is filtered and concentrated in vacuum, resulting in a brown solid. After purification by flash chromatography (cyclohexane, ethyl acetate), a white solid is obtained.

Yield: 18.1 g (79%)

RMN ¹H (CDCl$_3$, ppm): 0.87 (6H); 1.11-1.18 (2H); 1.20-1.38 (16H); 1.51 (1H); 1.63 (2H); 2.35 (2H).

Molecule 20: Product Obtained by Reaction Between Molecule 19a and L-Leucine.

To a solution of molecule 19a (18.05 g, 74.46 mmol) in THF (745 mL) at room temperature are successively added DCC (14.63 g, 70.92 mmol) and NHS (8.16 g, 70.92 mmol). After stirring for 40 hours at room temperature, the medium is cooled to 0° C. for 20 minutes, sinter filtered. L-leucine (9.77 g, 74.46 mmol), DIPEA (86 mL) and water (150 mL) are added to the filtrate. After stirring for 20 hours at room temperature, the medium is diluted with an aqueous solution saturated in NaHCO$_3$ (200 mL). The aqueous phase is washed with ethyl acetate (2×200 mL) and acidified with an aqueous solution of 2 N Hcl up to a pH of 1. The precipitate is filtered, thoroughly rinsed with water and vacuum dried at 50° C. The solid is triturated 3 times in pentane, sonicated, then filtered, resulting in a white solid.

Yield: 18.8 g (75%)

RMN ¹H (CDCl$_3$, ppm): 0.86 (6H); 0.96 (6H); 1.12-1.18 (2H); 1.20-1.78 (22H); 2.24 (2H); 4.58-4.63 (1H); 5.89 (1H).

LC/MS (ESI): 356.2; (calculated ([M+H]$^+$): 356.6).

Molecule 21a: Product Obtained by Reaction Between Molecule 20 and Boc-Tri(Ethylene Glycol)Diamine.

To a solution of molecule 20 (16.7 g, 46.97 mmol) in THF (235 mL) at room temperature are added DIPEA (20.3) and TBTU. After stirring for 20 minutes, Boc-tri(ethylene glycol)diamine (14 g, 56.36 mmol) is added. After stirring at room temperature for 5 hours, the mixture is concentrated under vacuum. The residue is redissolved in ethyl acetate (500 mL) and washed with an aqueous solution saturated in NaHCO$_3$ (3×200 mL), an aqueous solution of 1 N HCl (3×200 mL), and an aqueous solution saturated in NaCl (3×200 mL). After drying over Na$_2$SO$_4$, filtration and concentration under vacuum, the residue is purified by flash chromatography (cyclohexane, ethyl acetate, methanol), resulting in a colorless oil.

Yield: 23.5 g (85%)

RMN $^1$H (CDCl$_3$, ppm): 0.86 (6H); 0.93 (6H); 1.10-1.17 (2H); 1.19-1.08 (31H); 2.18 (2H); 3.23-3.65 (12H); 4.41-4.56 (1H); 5.12-5.47 (1H); 5.99-6.11 (0.75H); 6.48-6.65 (1H); 7.30-7.40 (0.25H).

Molecule A9

Using a process similar to the one used in the preparation of molecule A5a applied to molecule 21a (23.46 g, 40.04 mmol) without basic washing, the residue obtained after concentration under vacuum is triturated in an acetonitrile/acetone mixture. The supernatant is removed and the paste-like residue is vacuum dried. The residue is then triturated in acetone (150 mL) and the white solid of molecule A9 in the form of a hydrochloride salt is filtered, rinsed in acetone, then vacuum dried.

Yield: 13.0 g (64%)

RMN $^1$H (DMSO-d6, ppm): 0.79-0.90 (12H); 1.09-1.61 (24H); 2.03-2.17 (2H); 2.92-2.98 (2H); 3.15-3.23 (2H); 3.40 (2H); 3.50-3.58 (4H); 3.61 (2H); 4.30-4.23 (1H); 7.88-8.14 (5H).

LC/MS (ESI): 486.4; (calculated ([M-Cl]$^+$): 486.8).

Example A10: Molecule A10

Molecule 22a: Product Obtained by Reaction Between Octanoyl Chloride and L-Proline.

Using a process similar to the one used for the preparation of molecule 11 and applied to octanoyl chloride (150.0 g, 0.922 mol) and to L-proline (212.3 g, 1.844 mol), a colorless oil of molecule 22a is obtained after washings of the organic phase with a 10% solution of HCl (3×300 mL), an aqueous solution of NaCl (300 mL), dried over Na$_2$SO$_4$, filtration with cotton, concentration under reduced pressure, then the residue is purified by flash chromatography (eluent: DCM, MeOH)

Yield: 134 g (60%)

RMN $^1$H (CDCl$_3$, ppm): 0.87 (3H); 1.10-1.52 (8H); 1.57-1.74 (2H); 1.79-2.52 (6H); 3.37-3.67 (2H); 4.37-4.42 (0.07H); 4.53-5.63 (0.93H); 9.83 (1H).

LC/MS (ESI): 242.1 (calculated ([M+H]$^+$): 242.2).

Molecule 23a: Product Obtained by Coupling Between Molecule 22a and L-Lysine.

To a solution of molecule 22a (132 g, 0.547 mol) in THF (924 mL) cooled to a temperature below 5° C., are successively added NHS (66.1 g, 0.574 mol) and DCC (118.5 g, 0.574 mol). After stirring for 21 hours, the precipitate is eliminated by precipitation and the filtrate is added over 30 minutes to a solution of L-lysine (41.98 g, 0.287 mol) in a mixture of deionized water (82 mL) and DIPEA (476 mL, 2.735 mol) at 15° C. After stirring at room temperature for 23 hours, the reaction medium is concentrated under reduced pressure, resulting in an oily mixture which is diluted in water (1.3 L). The aqueous phase is washed twice with AcOEt (2×0.5 L), cooled to a temperature below 10° C., acidified by adding a solution of 6 N HCl (120 mL) to reach a pH of 1, then extracted three times with DCM (3×0.6 L). The organic phases are reunited, washed with a solution saturated in NaCl (0.6 L), dried over Na2SO4 then concentrated under reduced pressure. The foam obtained is redissolved in refluxing acetone (240 mL) for 2 hours. After one night at 10° C., pentane (240 mL) is added drop by drop. After stirring for 1 hour, the precipitate is recovered by vacuum filtration, washed with a 1:1 mixture of pentane and acetone (150 mL), then vacuum dried.

Yield: 83.9 g (52%)

RMN $^1$H (CDCl$_3$, ppm): 0.87 (6H); 1.06-1.78 (25H); 1.80-2.41 (13H); 2.80-3.72 (6H); 4.30-4.39 (0.15H); 4.46-4.70 (2.85H); 7.84 (1H); 7.93 (1H).

LC/MS (ESI): 593.5 (calculated ([M+H]$^+$): 593.4).

Molecule 24: Product Obtained by Coupling Between Molecule 23a and L-Lysine Methyl Ester.

To molecule 23a (76.26 g, 0.129 mol) are successively added HOPO (3.57 g, 32.1 mmol), LysOMe dihydrochloride (15.0 g, 64.3 mmol) and EDC (34.53 g, 0.18 mol) then DMF (600 mL) previously cooled to 5° C. is added. After dissolving, triethylamine (43.9 mL, 0.315 mol) is added, drop by drop, while keeping the temperature below 5° C. for 2 more hours after the end of the addition. After one night at room temperature, the reaction medium is poured into a mixture of water/ice (2 kg) and DCM (0.5 L). After stirring for 15 minutes, the phases are separated. The aqueous phase is extracted twice with DCM (2×0.4 L). The organic phases are reunited, washed with a solution of 1 N HCl (0.5 L), then with a solution saturated in NaCl (0.5 L), dried over Na$_2$SO$_4$, concentrated under reduced pressure, then the residue is purified by flash chromatography (eluent: DCM, MeOH).

Yield: 56.7 g (67%)

RMN $^1$H (CDCl$_3$, ppm): 0.87 (12H); 1.10-2.40 (82H); 2.86-3.72 (17H); 4.16-4.60 (7H); 6.83-8.01 (6H).

Molecule A10

A solution of molecule 24 (4.0 g, 3.05 mmol) in ethylenediamine (30 mL) is heated to 50° C. during one night. The reaction medium is then diluted with methyl-tetrahydrofuran, then the organic phase is washed 4 times with a solution saturated in NaCl (4×30 mL), then twice with water (2×50 mL) before being dried over Na2SO4 then concentrated under reduced pressure. The residue is solubilized in refluxing acetonitrile for 30 minutes, then the solution is cooled to room temperature while stirring for one night. The white precipitate is then recovered by vacuum filtration, washed with cold acetonitrile (2×20 mL), then vacuum dried.

Yield: 3.0 g (74%)

RMN $^1$H (CDCl$_3$, ppm): 0.87 (12H); 1.09-2.37 (84H); 2.74-4.56 (25H); 6.85-8.00 (7H).

LC/MS (ESI): 1338.0 (calculated ([M+H]$^+$): 1338.0).

Example A11: Molecule A11

Molecule A11 is obtained by the conventional method of in solid phase peptide synthesis (SPPS) in 2-chlorotrityle chloride (CTC) resin (40.0 g, 1.16 mmol/g). Grafting of the first amino acid Fmoc-Lys (Fmoc)-OH (1.5 equivalents) is carried out in DCM (10V), in the presence of DIPEA (3.0 equivalents). Sites which did not react are capped with methanol (0.8 mL/g resin) at the end of the reaction.

The couplings of protected amino acids Fmoc-Glu (OtBu)-OH (2.5 equivalents), Fmoc-Pro-OH (2.5 equivalents) and myristic acid (2.5 equivalents) are carried out in DMF (10V), in the presence of HATU (2.5 equivalents) and DIPEA (3.7 equivalents).

The Fmoc protective groups are removed using an 80:20 DMF/piperidine solution (10 V).

The product is cleaved from the resin using an 80:20 DCM/HFIP solution (10 V). After concentration under reduced pressure, the residue is purified by chromatography on silica gel (dichloromethane, methanol).

Yield 56.5 g (65%)

RMN $^1$H (CD$_3$OD, ppm): 0.90 (6H); 1.22-2.53 (140H); 3.12-3.25 (2H); 3.43-3.80 (4H); 4.17-4.54 (9H).

LC/MS (ESI+): 1894.5 (calculated ([M+Na]$^+$): 1894.2).

Example A12: Molecule A12

Molecule 25: Product Obtained by Hydrogenation of Farnesol.

To a solution of farnesol (60.00 g, 269.82 mmol) in THF (1200 mL) under argon is added platinum oxide (PtO$_2$, 613 mg, 2.70 mmol) and the medium is placed under 1 atm of dihydrogen, then stirred for 6 hours at room temperature. After filtration with celite and rinsing in THF, a black oil of molecule 25 is obtained after concentration under reduced pressure. This compound is used without additional purification.

Yield 61.60 g (100%)

RMN $^1$H (CDCl$_3$, ppm): 0.85 (3H); 0.87 (6H); 0.90 (3H); 1.01-1.43 (15H); 1.47-1.66 (3H); 3.62-3.76 (2H).

Molecule 26: Product Obtained by Oxidation of Molecule 25

To a solution of molecule 25 (61.60 g, 269.68 mmol) dichloroethane/water mixture (1350 mL/1080 mL) are successively added tetramethylammonium bromide, (46.95 g, 145.63 mmol), acetic acid (416 mL, 7.28 mol) then KMnO$_4$ (127.85 g, 809.04 mmol) by small fractions while maintaining the temperature between 11 and 13° C. The reaction medium is then stirred for 4 hours and 30 minutes by refluxing, cooled to 0° C. then acidified up to pH 1 with a solution of 37% HCl (50 mL). Na$_2$SO$_3$ (186.94 g) is added progressively while maintaining the temperature between 0 and 10° C. and the medium is stirred until it is completely colorless. The medium is acidified up to a pH of 1 with a solution of 37% HCl then water (500 mL) and DCM (500 mL) are added. The phases are separated and the aqueous phase is extracted with DCM (2×500 mL). The combined organic phases are washed with an aqueous solution of 10% HCl (400 mL), water (2×400 mL), an aqueous solution saturated in NaCl (400 mL), dried over Na$_2$SO$_4$, filtered and concentrated under reduced pressure. The yellow oil of molecule 26 is obtained after purification by flash chromatography (eluent: cyclohexane, AcOEt).

Yield 54.79 g (84%)

RMN $^1$H (CDCl$_3$, ppm): 0.85 (3H); 0.87 (6H); 0.97 (3H); 1.03-1.43 (13H); 1.52 (1H); 1.91-2.01 (1H); 2.11-2.18 (1H); 2.32-2.39 (1H).

LC/MS (ESI−): 241.3 (calculated ([M−H]$^-$): 241.2).

Molecule 27: Product Obtained by Coupling Between Molecule 26 and L-Prolinate.

To a solution of molecule 26 (54.70 g, 225.66 mmol) in DCM (1500 mL) at 0° C. are successively added HOBt (3.46 g, 22.57 mmol), DIPEA (117.92 mL, 676.97 mmol), methyl L-prolinate hydrochloride (56.06 g, 338.49 mmol) followed by EDC (64.89 g, 338.49 mmol). The reaction mixture is stirred at 0° C. for 1 hour, then at room temperature for 18 hours. The medium is then diluted with DCM (1000 mL), then washed with an aqueous solution saturated in NaHCO$_3$ (2×1 L), an aqueous solution of 1 N HCl (2×1000 mL) and an aqueous solution saturated in NaCl (2×1000 mL). The organic phase is dried over Na$_2$SO$_4$, filtered and concentrated under reduced pressure which results in a yellow oil of molecule 27 which is used without additional purification.

Yield 77.15 g (97%)

RMN $^1$H (DMSO-d$_6$, ppm): 0.79-0.89 (12H); 0.98 1.43 (13H); 1.51 (1H); 1.70-2.32 (7H); 3.33-3.42 (0.4H); 3.46-3.57 (1.6H); 3.59 (2.4H); 3.67 (0.6H); 4.23-4.32 (0.8H); 4.53-4.62 (0.2H).

LC/MS (ESI+): 354.2 (calculated ([M+H]$^+$): 354.3).

Molecule 28: Product Obtained by Saponification of Molecule 27.

To a solution of molecule 27 (77.15 g, 218.22 mmol) in a 1:1 THF/MeOH mixture (1454 mL) is added, drop by drop, a solution of LiOH (7.84 g, 327.33 mmol) at 0° C. in water (727 mL). The reaction mixture is stirred at 0° C. for 18 hours then at room temperature for 5 hours. Organic solvents are evaporated under reduced pressure. Water (500 mL), a 10% HCl aqueous solution (200 mL) and DCM (800 mL) are added, and the phases are separated. The aqueous phase is extracted with DCM (2×1 L). The reunited organic phases are washed with water (500 mL), a saturated aqueous solution in NaCl (500 mL), dried over Na$_2$SO$_4$, filtered and concentrated under reduced pressure which results in a yellow oil of molecule 28 which is used without additional purification.

Yield 71.72 g (97%)

RMN $^1$H (DMSO-d$_6$, ppm): 0.73-0.95 (12H); 0.95-1.42 (13H); 1.51 (1H); 1.65-2.32 (7H); 3.24-3.64 (2H); 4.13-4.28 (0.8H); 4.37-4.50 (0.2H); 12.44 (1H).

LC/MS (ESI+): 340.2 (calculated ([M+H]$^+$): 340.3).

Molecule A12

Molecule A12 is obtained by the conventional solid phase peptide synthesis (SPPS) method in 2-chlorotrityle chloride (CTC) resin (34.5 g, 1.16 mmol/g).

Grafting of ethylene diamine (10.0 equivalents) is carried out in DCM (10V), in the presence of DIPEA (10.0 equivalents). Sites which did not react are capped with methanol (0.8 mL/g resin) at the end of the reaction.

The couplings of protected amino acids Fmoc-Lys (Fmoc)-OH (1.5 equivalents), Fmoc-Glu (OMe)-OH (3.0 equivalents) and molecule 28 (3.0 equivalents) are carried out in a 1:1 DCM/DMF mixture (10V), in the presence of HATU (1.0 equivalent in relation to the acid) and DIPEA (2.0 equivalents in relation to the acid).

The Fmoc protective groups are removed using a solution of 80:20 DMF/piperidine (10 V) (after coupling with lysine) or a solution of 50% morpholine in DMF (after coupling of glutamic acids).

The product is cleaved from resin using a 50:50 DCM/TFA solution (10 V). After evaporation, the residue is solubilized in MeTHF (450 mL) and the organic phase is washed with an aqueous solution of NaHCO$_3$ (3×450 mL) and an aqueous solution saturated in NaCl (200 mL). After drying over Na2SO4, the organic phase is filtered, concentrated under reduced pressure and the residue is purified by chromatography on silica gel (dichloromethane methanol, NH$_4$OH).

Yield: 13.95 g (31% overall over 7 steps).

RMN $^1$H (DMSO-d$_6$, ppm): 0.73-0.91 (24H); 0.96-2.41 (56H); 2.72 (2H); 2.89-3.10 (2H); 3.15-3.26 (2H); 3.26-3.51 (4H); 3.57 (3H); 3.58 (3H); 3.99-4.50 (5H); 6.07 (2H); 7.59-8.39 (5H).

LC/MS (ESI+): 1118.2 (calculated ([M+H]$^+$): 1117.8).

Example A13: Molecule A13

Molecule 29: Product Obtained by the Polymerization of γ-Benzyl-L-Glutamate N-Carboxyanhydride Initiated by N-Boc-Ethylenediamine.

In a reactor, γ-benzyl-L-glutamate N-carboxyanhydride (39.44 g, 149.82 mmol) is solubilized in DMF (81 mL) at 25° C. The mixture is then stirred until completely dissolved, cooled to −10° C., then a solution of BocEDA (6.00 g, 37.45 mmol) in DMF (7 mL) is quickly introduced. The reaction medium is stirred at 0° C. for 3 hours then a solution of HCl in 1,4-dioxane (3.33 M, 11.8 mL, 39.29 mmol) is added.

The reaction medium is stirred at room temperature then run over an MeOH/IPE solution (125 mL/495 mL), cooled by an ice bath. After stirring for 65 hours at room temperature, the precipitate is sinter filtered, washed with IPE (2×90 mL) and dried at 30° C. under reduced pressure.

Yield: 21.71 g (54%)

DP (estimated using RMN $^1$H): 4.9

The calculated average molar mass of molecule 29 as a hydrochloride salt is 1270.9 g/mol.

RMN $^1$H (DMSO-d6, ppm): 1.35 (9H); 1.72-2.09 (9.8H); 2.23-2.60 (9.8H); 2.86-3.19 (4H); 3.85 (1H); 4.14-4.52 (3.9H); 4.86-5.23 (9.8H); 6.33-6.85 (1H); 7.09-7.55 (24.5H); 7.88-8.42 (6.9H); 8.67 (1H).

Molecule 30: Product Obtained by Coupling Between Myristoyl Chloride and Molecule 29.

After solubilization of molecule 29 as a hydrochloride salt (12.46 g, 9.80 mmol) in DCM (115 mL), the solution is cooled to 0° C. Then, triethylamine (2.35 g, 23.24 mmol) and a solution of myristoyl chloride (3.16 g, 12.79 mmol) in DCM (16 mL) are successively added. The reaction medium is stirred at 0° C. for 4 hours, then at temperature for 2 hours, before being run over IPE (920 mL). After stirring for 14 hours at room temperature, the precipitate is filtered, washed with EtOH (2×145 mL then 100 mL) and dried at 30° C. under reduced pressure.

Yield: 9.77 g (69%)

DP (estimated using RMN $^1$H): 5.1

The calculated average molar mass of molecule 30 is 1488.7 g/mol.

RMN $^1$H (CDCl$_3$, ppm): 0.87 (3H); 1.07-1.51 (29H); 1.51-1.64 (2H); 1.80-2.75 (22.4H); 2.98-3.73 (4H); 3.84-4.50 (5.1H); 4.86-5.32 (10.2H); 5.71-6.47 (1H); 6.72-8.38 (31.6H).

Molecule A13

To a solution of the molecule 30 (4.70 g, 3.16 mmol) in DCM (31 mL) at 0° C. is added TFA (31 mL). The reaction mixture is stirred at 0° C. for 2 hours, then concentrated under reduced pressure and at room temperature. The residue is redissolved in DCM (100 mL) then dry concentrated under reduced pressure and at room temperature. The residue is solubilized in DCM (100 mL) and washed with an aqueous solution of carbonate buffer at pH=10.4 (326 mL then 2×200 mL), then with an aqueous solution of HCl (0.1 N, 2×200 mL). The organic solution is dried over Na$_2$SO$_4$, filtered and then dry concentrated at 40° C. under reduced pressure.

Yield: 3.96 g (88%)

DP (estimated using RMN $^1$H): 5.2

The calculated average molar mass of molecule A13 in the form of a hydrochloride salt is 1446.9 g/mol.

RMN $^1$H (TFA-d, ppm): 0.91 (3H); 1.17-1.47 (20H); 1.60-1.74 (2H); 1.99-2.78 (22.8H); 3.41-4.05 (4H); 4.62-4.83 (5.2H); 5.05-5.35 (10.4H); 6.99-8.02 (26H).

Example A14: Molecule A14

Molecule 31: Product Obtained by Reaction Between Molecule 14 and Boc-Ethylenediamine.

Using a process similar to the one used for the preparation of molecule 10 and applied to molecule 14 (12.00 g, 40.35 mmol) and to BocEDA (7.76 g, 48.42 mmol), a colorless oil of molecule 31 is obtained and used without additional purification.

Yield: 17.40 g (94%)

RMN $^1$H (CDCl$_3$, ppm): 0.86 (3H); 1.11-1.68 (18H); 1.41 (9H); 1.80-2.38 (6H); 3.06-3.35 (4H); 3.37-3.49 (1H); 3.51-3.73 (1H); 4.26-4.31 (0.1H); 4.45-4.52 (0.9H); 4.91-5.19 (1H); 6.97 (1H); 7.23 (0.9H).

LC/MS (ESI+): 440.4 (calculated ([M+H]$^+$): 440.3).

Molecule A14

After using a process similar to the one used for the preparation of molecule A2 and applied to molecule 31 (8.85 g, 20.13 mmol) in solution in DCM, a white solid of molecule A14 is obtained after basic washing, concentration under reduced pressure then recrystallization in acetonitrile.

Yield: 6.53 g (96%)

RMN $^1$H (DMSO, ppm): 0.85 (3H); 1.07-1.56 (20H); 1.68-2.03 (4H); 2.09-2.29 (2H); 2.50-2.58 (2H); 2.96-3.11 (2H); 3.21-3.59 (2H); 4.17-4.21 (0.65H); 4.25-4.29 (0.35H); 7.68 (0.65H); 8.00 (0.35H) LC/MS (ESI): 340.3 (calculated ([M+H]$^+$): 340.3). 0.3).

Molecule A15

Molecule A15 is obtained by the conventional solid phase peptide synthesis method (SPPS) in 2-chlorotrityle chloride (CTC) resin (16.0 g, 1.16 mmol/g).

Grafting of ethylene diamine (20.0 equivalents) is carried out in DCM (10V). Sites which did not react are capped with methanol (0.8 mL/g resin) at the end of the reaction.

The couplings of protected Fmoc-Lys(Fmoc)-OH amino acids (3.0 equivalents), Fmoc-Glu(OBn)-OH (4.0 equivalents) and molecule 11 (3.0 equivalents) are carried out in DMF (10V) (couplings of Lys and molecule 11), or in a mixture of 1:1 DCM/DMF (10V) (Glu coupling) in the presence of HATU (1.0 equivalent in relation to the acid) and DIPEA (1.5 equivalents in relation to the acid).

The Fmoc protective groups are removed using an 80:20 solution of DMF/piperidine (10 V) (after coupling with lysine) or a 1% solution of DBU in DMF (after coupling with glutamic acids)

The product is cleaved from resin using a 50:50 DCM/TFA solution (10 V). After evaporation, the residue is solubilized in ethyl acetate (400 mL) and the organic phase is washed with an aqueous solution of carbonate buffer at pH 10 (1 M) (2×400 mL) and an aqueous solution saturated in NaCl (400 mL). After drying over Na$_2$SO$_4$, the organic phase is filtered, concentrated under reduced pressure and the residue is purified by chromatography on silica gel (dichloromethane methanol, NH$_4$OH), followed by recrystallization in acetonitrile.

Yield: 16.20 g (70% overall over 7 steps).

RMN $^1$H (DMSO-d$_6$, ppm): 0.85 (6H); 1.11-2.57 (72H); 2.50-5.57 (2H); 2.90-3.08 (4H); 3.36-3.61 (4H); 4.06-4.43 (5H); 5.08 (4H); 7.27-7.40 (10H); 7.51-8.31 (5H).

LC/MS (ESI+): 1242.0 (calculated ([M+H]$^+$): 1241.9).

Example A16: Molecule A16

Molecule 32: Product Obtained by SPPS

Molecule 32 is obtained by the conventional solid phase peptide synthesis (SPPS) in 2-chlorotrityle chloride (CTC) resin (50.0 g, 1.14 mmol/g).

Grafting of the first Fmoc-Glu(OtBu)-OH amino acid (1.3 equivalents) is carried out in DCM (10V), in the presence of DIPEA (2.6 equivalents). Sites which did not react are capped with methanol (0.8 mL/g resin) at the end of the reaction.

The couplings of protected Fmoc-Glu(OtBu)-OH amino acids (1.3 equivalents), and molecule 11 (3.0 equivalents) are carried out in DMF (10V), in the presence of HATU (1.0 equivalent in relation to the acid) and DIPEA (1.5 equivalents in relation to the acid).

The Fmoc protective groups are removed using an 80:20 DMF/piperidine solution (10 V).

The product is cleaved from resin using an 80:20 DCM/HFIP solution (10 V).

After concentration under reduced pressure, the residue is purified by trituration in diisopropylether.

Yield: 35.78 g (90%)

RMN $^1$H (CDCl$_3$, ppm): 0.88 (3H); 1.19-1.35 (20H); 1.43 (9H); 1.44 (9H); 1.55-1.67 (2H); 1.90-2.46 (14H); 3.46-3.54 (1H); 3.63-3.71 (1H); 4.33-4.40 (1H); 4.43-4.52 (2H); 7.35 (0.05H); 7.40 (0.05H); 7.63 (0.95H); 7.94 (0.95H).

LC/MS (ESI+): 696.4 (calculated ([M+H]$^+$): 696.5).

Molecule 33: Product Obtained by Reaction Between Molecule 32 and N-Cbz Ethylenediamine.

Using a process similar to the one used for the preparation of molecule 7 and applied to molecule 32 (30.0 g, 43.11 mmol) and to N-CBz ethylenediamine hydrochloride (CBzEDA·HCl, 11.93 g, 51.73 mmol) and in the presence of DIPEA (15.0 mL, 86.22 mmol), a beige solid of molecule 33 is obtained. It is used without additional purification.

Yield: 37.6 g (100%)

RMN $^1$H (CDCl$_3$, ppm): 0.88 (3H); 1.19-1.34 (20H); 1.42 (9H); 1.44 (9H); 1.52-2.54 (16H); 3.16-3.70 (6H); 4.08-4.15 (1H); 4.19-4.25 (1H); 4.43-4.53 (1H); 5.00 (1H); 5.08 (1H); 6.56 (1H); 7.00 (1H); 7.24-7.37 (5H); 7.59 (1H); 8.41 (1H).

LC/MS (ESI+): 872.5 (calculated ([M+H]$^+$): 872.6).

Molecule A16

To a solution of molecule 33 (37.6 g, 43.11 mmol) in methanol (376 mL) is added Pd/Al$_2$O$_3$ (3.76 g) under an argon atmosphere. The mixture is placed under hydrogenic atmosphere (7 bar) and stirred at room temperature for 72 hours. After filtration of the catalyst on sintered P4, then on an Omnipore 0.2 μm PTFE hydrophilic membrane, the filtrate is evaporated under reduced pressure resulting in molecule A16 in the form of a sticky oil.

Yield: 31.06 g (98%)

RMN $^1$H (CDCl$_3$, ppm): 0.88 (3H); 1.19-1.35 (20H); 1.43 (9H); 1.46 (9H); 1.56-1.67 (2H); 1.92-2.12 (6H); 2.24-2.54 (8H); 2.71 (2H); 2.90 (2H); 3.22-3.32 (1H); 3.42-3.51 (1H); 3.55-3.64 (1H); 3.73-3.81 (1H); 4.13-4.21 (1H); 4.26-4.33 (1H); 4.39-4.48 (1H); 7.10 (1H); 7.71 (1H); 8.45 (1H).

LC/MS (ESI+): 738.5 (calculated ([M+H]$^+$): 738.5).

Molecule A17

Molecule A17 is obtained by the conventional solid phase peptide synthesis (SPPS) in 2-chlorotrityle chloride (CTC) resin (64.66 g, 1.16 mmol/g).

Grafting of ethylene diamine (10.0 equivalents) is carried out in DCM (10V), in the presence of DIPEA (10.0 equivalents). Sites which did not react are capped with methanol (0.8 mL/g resin) at the end of the reaction.

The couplings of the protected Fmoc-Glu (OMe)-OH amino acid (1.5 equivalents) and of molecule 28 (1.5 equivalents) are carried out in a 1:1 DCM/DMF mixture (10V) for the coupling of glutamic acid or in DMF (10V) for the coupling of molecule 28, in the presence of HATU (1.0 equivalent in relation to the acid) and DIPEA (2.0 equivalents in relation to the acid).

The Fmoc protective groups are removed using a 50:50 DMF/morpholine solution (10 V).

The product is cleaved from resin using a 50:50 DCM/TFA solution (10 V). After evaporation, the residue is solubilized in MeTHF (500 mL) and the organic phase is washed with an aqueous solution of 5% Na$_2$CO$_3$ (3×250 mL), then the aqueous phases are extracted using MeTHF (1×150 mL). The reunited organic phases are dried over Na$_2$SO$_4$ and filtered. A solution of HCl in MeOH (1.25 M) is added, then the medium is concentrated under reduced pressure. The residue is purified on silica gel (dichloromethane, methanol) resulting in a hydrochloride salt of molecule A17 in the form of a light brown solid.

Yield: 12.48 g (30% overall over 5 steps).

RMN $^1$H (DMSO-d$_6$, ppm): 0.76-0.90 (12H); 0.97-1.41 (13H); 1.45-1.55 (1H); 1.68-2.40 (11H); 2.77-2.92 (2H); 3.20-3.64 (4H); 3.57 (3H); 4.15-4.49 (2H); 7.90-8.48 (5H).

LC/MS (ESI+): 525.5 (calculated ([M+H]$^+$): 525.4).

Example A18: Molecule A18

Molecule 34: Product Obtained by Hydrogenation of Phytol.

To a solution of phytol (260.00 g, 878.78 mmol) in ethanol (1.25 L) under argon 50% Raney nickel is added in water (30.75 g, 175.36 mmol). The medium is placed under 1 bar of hydrogen, then stirred for 8 days at room temperature. After filtration on a pad of celite/silica/celite while rinsing in ethanol, a colorless oil of molecule 34 is obtained after concentration under reduced pressure.

Yield: 261.40 g (quant.)

RMN $^1$H (CDCl$_3$, ppm): 0.84 (6H); 0.86 (6H); 0.89 (3H); 1.00-1.46 (22H); 1.46-1.68 (3H); 3.61-3.73 (2H).

Molecule 35: Product Obtained by Oxidation of Molecule 34.

Using a process similar to the one used for the preparation of molecule 26, applied to molecule 34 (29.00 g, 97.13 mmol) a yellow oil of molecule 35 is obtained.

Yield: 28.70 g (94%)

RMN $^1$H (CDCl$_3$, ppm): 0.84 (6H); 0.86 (6H); 0.97 (3H); 1.00-1.41 (20H); 1.52 (1H); 1.96 (1H); 2.14 (1H); 2.35 (1H); 11.31 (1H).

LC/MS (ESI): 311.1 (calculated ([M−H]$^-$): 311.3).

Molecule 36: Product Obtained by Coupling Between Molecule 35 and L-Prolinate.

Using a process similar to the one used for the preparation of molecule 27, applied to molecule 35 (18.00 g, 57.59 mmol)) and to methyl L-propionate hydrochloride (14.31 g, 86.39 mmol), a yellow oil of molecule 36 is obtained.

Yield: 23.20 g (95%)

RMN $^1$H (DMSO-d$_6$, ppm): 0.78-0.89 (15H); 0.97-1.43 (20H); 1.43-1.56 (1H); 1.70-1.96 (4H); 1.96-2.32 (3H); 3.33-3.56 (2H); 3.59 (0.6H); 3.67 (2.4H); 4.27 (0.8H); 4.57 (0.2H).

LC/MS (ESI): 424.4 (calculated ([M+H]$^+$): 424.4).

Molecule 37: Product Obtained by Saponification of Molecule 36.

Using a process similar to the one used for the preparation of molecule 28, applied to molecule 36 (21.05 g, 49.68 mmol) a yellow oil of molecule 37 is obtained.

Yield: 20.40 g (99%)

RMN $^1$H (DMSO-d$_6$, ppm): 0.77-0.91 (15H); 0.97-1.43 (20H); 1.43-1.56 (1H); 1.67-1.96 (4H); 1.96-2.29 (3H); 3.26-3.56 (2H); 4.20 (0.8H); 4.41 (0.2H).

LC/MS (ESI): 410.3 (calculated ([M+H]$^+$): 410.4).

Molecule A18

Molecule A18 is obtained by the conventional solid phase peptide synthesis (SPPS) in 2-chlorotrityle chloride (CTC) resin (26.72 g, 1.16 mmol/g).

Using a process similar to the one used for the preparation of molecule A17, applied to 4,7,10-trioxa-1,13-tridecane diamine (TOTA, 68.30 g, 310.0 mmol), to Fmoc-Glu(OMe)-

OH (23.77 mmol, 62.00 mmol) and to molecule 37 (19.04 g, 46.50 mmol), a yellow oil of molecule A18 in the form of a hydrochloride is obtained.

Yield: 5.53 g (23% overall over 5 steps).

RMN $^1$H (DMSO-d$_6$, ppm): 0.76-0.89 (15H); 0.97-2.38 (36H); 2.77-2.87 (2H); 3.00-3.17 (3H); 3.32-3.54 (13H); 3.57 (3H); 4.09-4.18 (0.75H); 4.20-4.29 (1H); 4.39-4.47 (0.25H); 7.63-8.36 (5H).

LC/MS (ESI+): 755.7 (calculated ([M+H]$^+$): 755.6).

Example A19: Molecule A19

Molecule A19 is synthesized in the same way as molecule A16, using molecule 14 instead of molecule 11 during the SPPS step.

Overall yield (3 steps): 32.6 g (81%)

RMN $^1$H (CDCl$_3$, ppm): 0.88 (3H); 1.20 1.35 (16H); 1.43 (9H); 1.46 (9H); 1.56-1.68 (9H); 1.93-2.11 (6H); 2.24-2.55 (10H); 2.85 (2H); 3.19-3.29 (1H); 3.38-3.48 (1H); 3.55-3.64 (1H); 3.74-3.82 (1H); 4.14-4.21 (1H); 4.25-4.32 (1H); 4.41-4.50 (1H); 7.03 (1H); 7.69 (1H); 8.42 (1H).

LC/MS (ESI): 710.4 (calculated ([M+H]$^+$): 710.5).

Example A20: Molecule A20

Molecule A20 is obtained by the conventional solid phase peptide synthesis (SPPS) in 2-chlorotrityle chloride (CTC) resin (40.00 g, 1.16 mmol/g).

Grafting of ethylene diamine (20.0 equivalents) is carried out in DCM (10V). Sites which did not react are capped with methanol (0.8 mL/g resin) at the end of the reaction.

The couplings of protected Fmoc-Lys (Fmoc)-OH amino acids (1.5 equivalents), Fmoc-Glu(OtBu)-OH (2.5 equivalents) and molecule 11 (2.5 equivalents) are carried out in DMF (10 V), in the presence of HATU (1.0 equivalent in relation to the acid) and DIPEA (1.5 equivalents in relation to the acid).

The Fmoc protective groups are removed using an 80:20 DMF/piperidine solution (10 V).

The product is cleaved from resin using a 50:50 DCM/TFA solution (10 V). After evaporation, the residue is solubilized in water (600 mL), the pH of the solution is adjusted to 7 by adding a solution of NaOH 5 N, then the product is lyophilized. The lyophilizate is purified by column chromatography on silica gel (dichloromethane, methanol, NH$_4$OH), resulting in molecule A20 in the form of a white solid.

Yield: 24.6 g (50% overall in 7 steps).

RMN $^1$H (MeOD-d4, ppm): 0.90 (6H); 1.18-2.45 (68H); 2.45-2.60 (2H); 3.05-3.11 (2H); 3.11-3.19 (1H); 3.23-3.33 (1H); 3.43-3.66 (4H); 3.82-3.94 (2H); 4.10-4.51 (5H).

LC/MS (ESI+): 1061.9 (calculated ([M+H]$^+$): 1061.8).

Part B—Synthesis of the Hydrophobic Co-Polyamino Acids
i) Co-Polyamino Acids According to Formulas XXXa, XXXb and XXXb', XXXb"

| No. | CO-POLYAMINO ACIDS BEARING CARBOXYLATE CHARGES AND HYDROPHOBIC RADICALS |
|---|---|
| B1 | 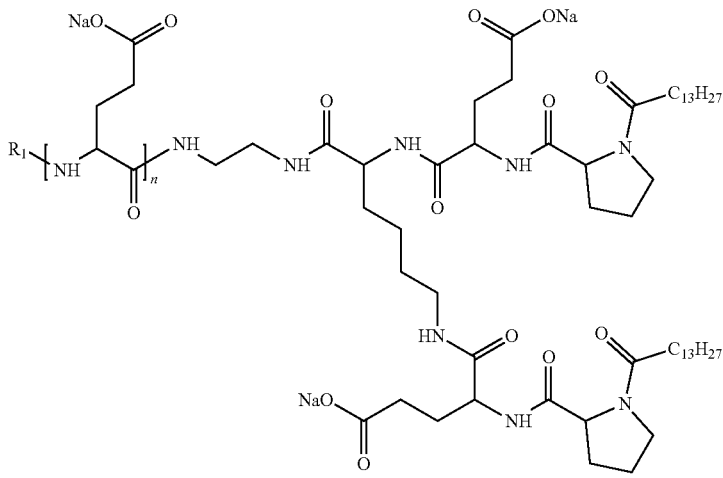 |
| | i = 0.038, DP = 26 |
| | R$_1$ = H or pyroglutamate |
| B2 | 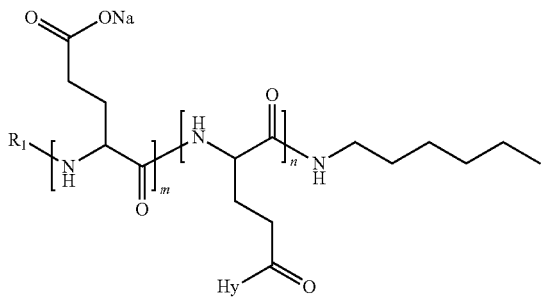 |
| | i = 0.15, DP (m + n) = 40 |

-continued
| No. | CO-POLYAMINO ACIDS BEARING CARBOXYLATE CHARGES AND HYDROPHOBIC RADICALS |
|---|---|
| | Hy = 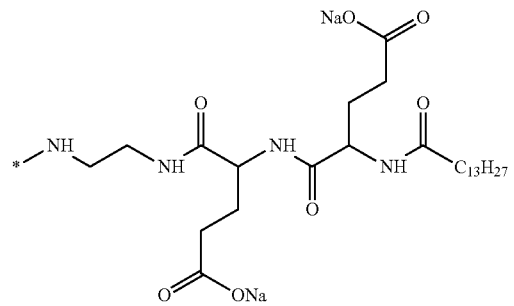
$R_1$ = H or pyroglutamate |
| B3 | 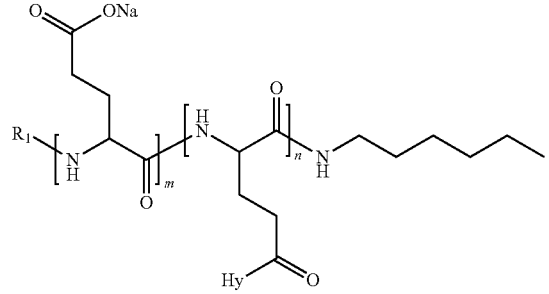
i = 0.15, DP (m + n) = 40
Hy = 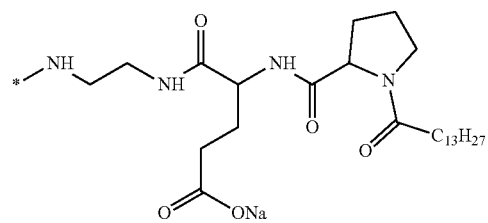
$R_1$ = H or pyroglutamate |
| B4 | 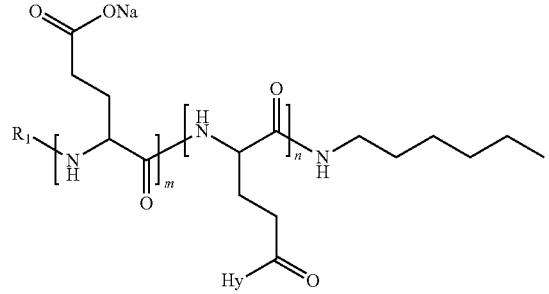
i = 0.15, DP (m + n) = 40 |

-continued
| No. | CO-POLYAMINO ACIDS BEARING CARBOXYLATE CHARGES AND HYDROPHOBIC RADICALS |
|---|---|
Hy =
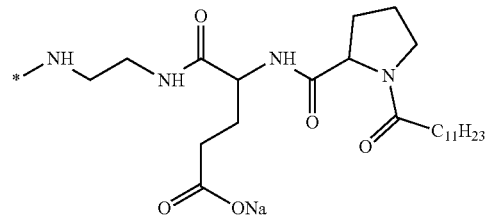
R₁ = H or pyroglutamate
B5
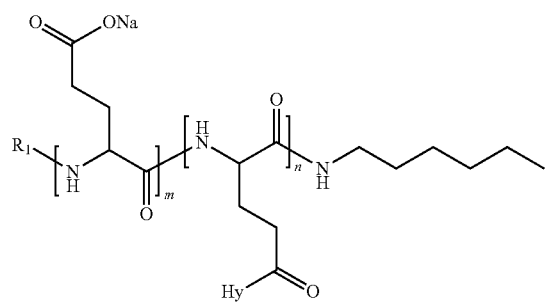
i = 0.15, DP (m + n) = 40
Hy =
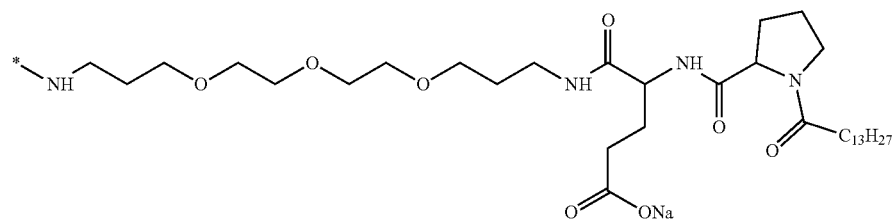
R₁ = H or pyroglutamate
B7
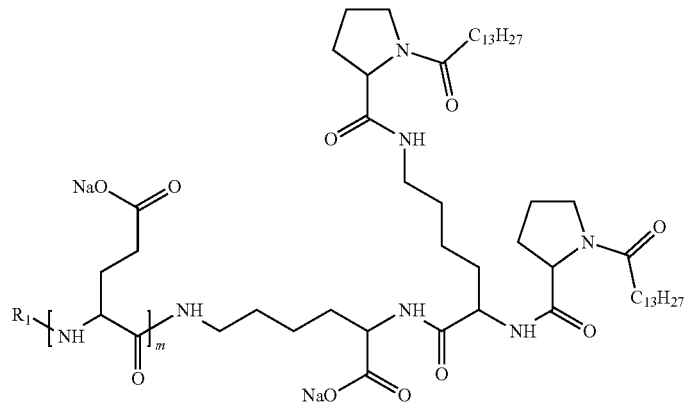
i = 0.038, DP = 26
R₁ = H or pyroglutamate -continued
| No. | CO-POLYAMINO ACIDS BEARING CARBOXYLATE CHARGES AND HYDROPHOBIC RADICALS |
|---|---|
| B13 | 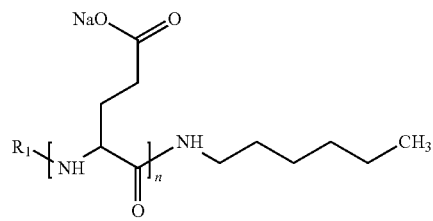
i = 0.042, DP = 24
R₁ = 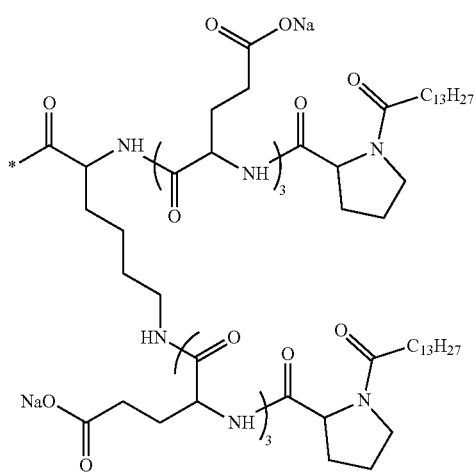 |
| B14 | 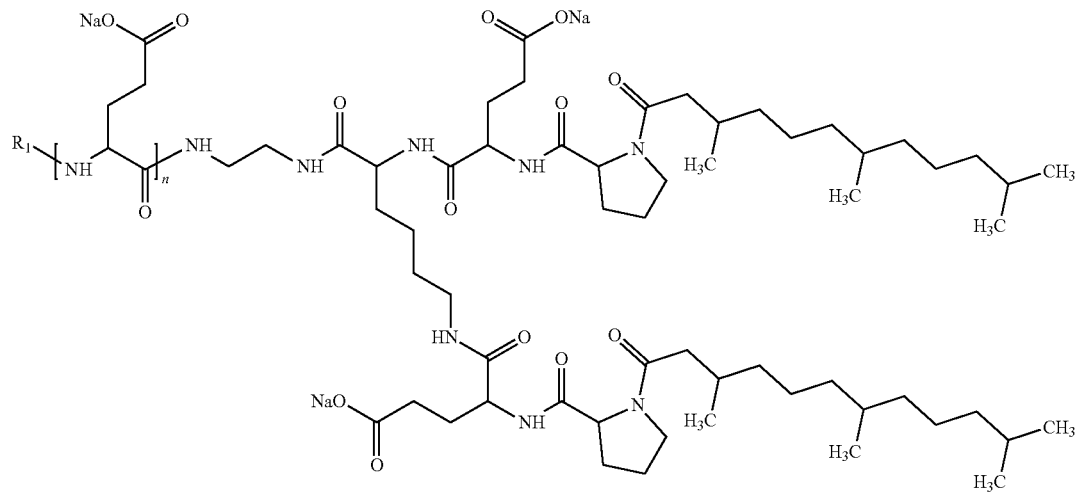
i = 0.042, DP = 24
R₁ = H or pyroglutamate |

-continued
| No. | CO-POLYAMINO ACIDS BEARING CARBOXYLATE CHARGES AND HYDROPHOBIC RADICALS |
|---|---|
| B15 | 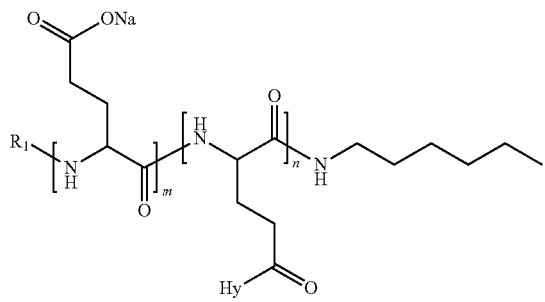
i = 0.15, DP (m + n) = 40
Hy =
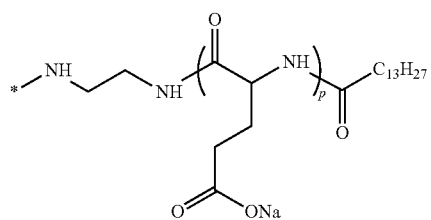
DP (p) = 5.2
$R_1$ = H or pyroglutamate |
| B17 | 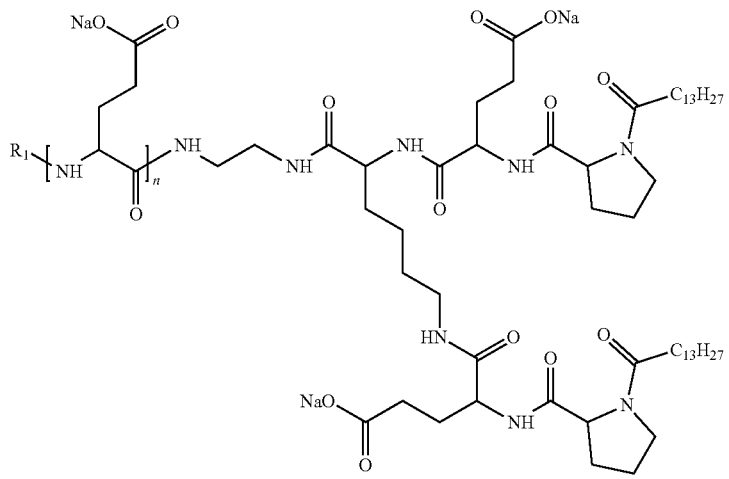
i = 0.1, DP = 10
$R_1$ = H or pyroglutamate |
| B18 | 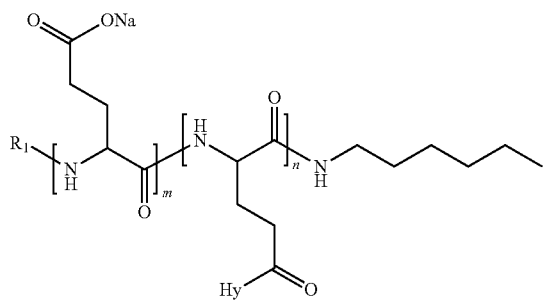
i = 0.15, DP (m + n) = 40 |

| No. | CO-POLYAMINO ACIDS BEARING CARBOXYLATE CHARGES AND HYDROPHOBIC RADICALS |
|---|---|
| | Hy = 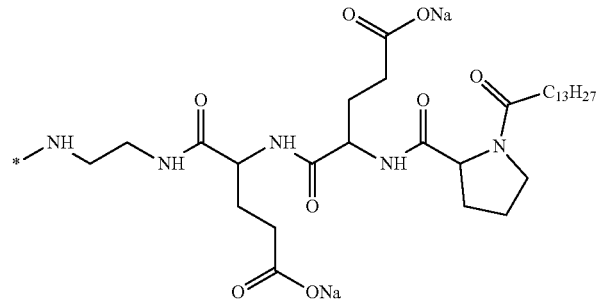<br>$R_1$ = H or pyroglutamate |
| B19 | 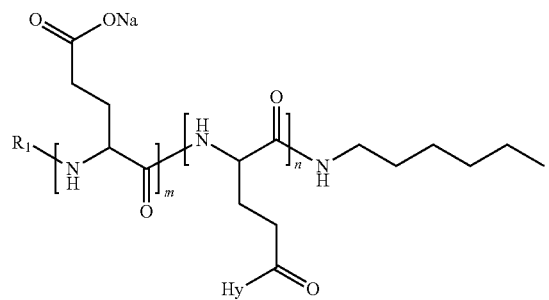<br>i = 0.15, DP (m + n) = 40<br><br>Hy = 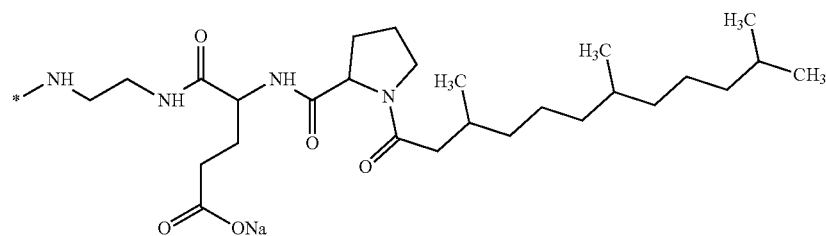<br>$R_1$ = H or pyroglutamate |
| B20 | 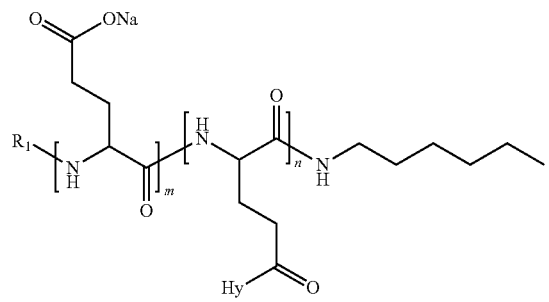<br>i = 0.15, DP (m + n) = 40 |

| No. | CO-POLYAMINO ACIDS BEARING CARBOXYLATE CHARGES AND HYDROPHOBIC RADICALS |
|---|---|
| | Hy = 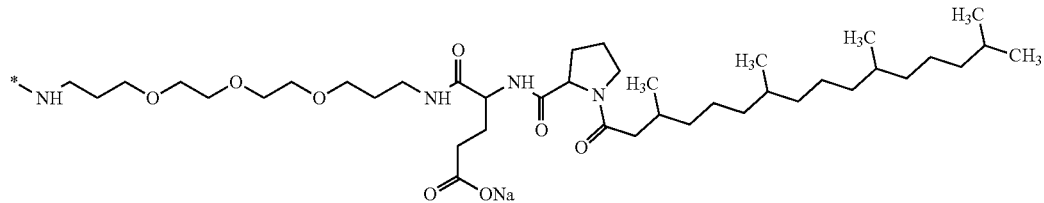<br>R₁ = H or pyroglutamate |
| B21 | 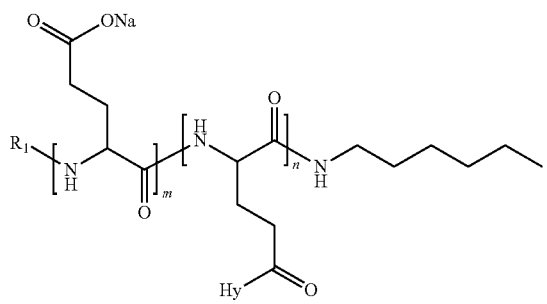<br>i = 0.15, DP (m + n) = 40<br><br>Hy = 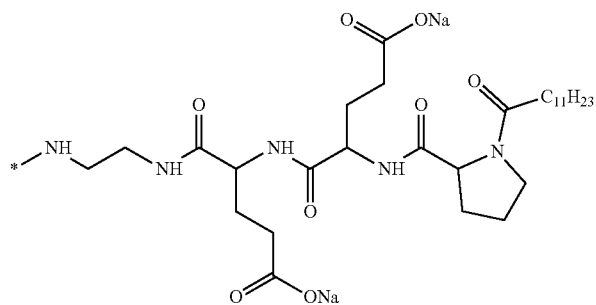<br>R₁ = H or pyroglutamate |
| B22 | 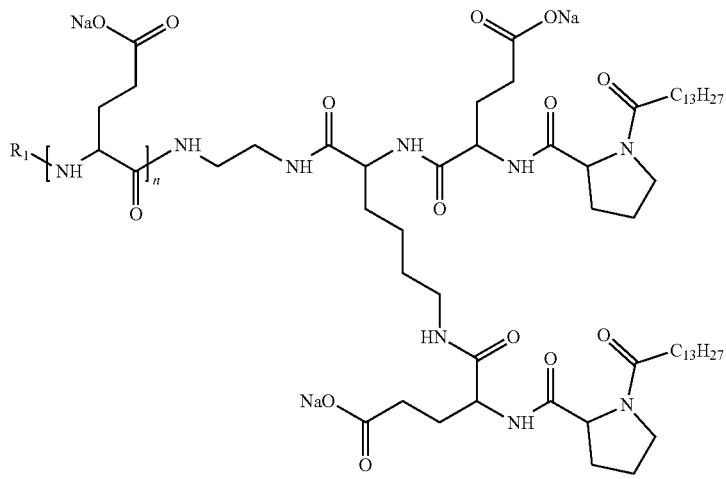<br>i = 0.05, DP = 20<br>R₁ = H or pyroglutamate |

Co-Polyamino Acid B1: Sodium Poly-L-Glutamate Modified at One of its Ends by Molecule A1 and Having a Number-Average Molar Mass (Mn) of 2800 g/mol γ-benzyl-L-glutamate N-carboxyanhydride (8.95 g, 34 mmol) is solubilized in a previously oven-dried receiving flask in anhydrous DMF (34 mL). The mixture is cooled to 4° C., then a solution of molecule A1 (1.64 g, 1.55 mmol) in chloroform (6.6 mL) is introduced quickly. The mixture is stirred from 4° C. to room temperature for 68 hours, then heated to 65° C. for 2 hours. Half of the solvent is distilled under reduced pressure, then the reaction medium is cooled to room temperature and poured, drop-by-drop into diisopropyl ether (300 mL) while stirring. The white precipitate is recovered by filtration, washed with diisopropyl ether (5×50 mL) then dried under reduced pressure at 30° C., resulting in a white solid. The solid (7.9 g) is diluted in TFA (30 mL), and a 33% solution of hydrobromic acid (HBr) in acetic acid (21 mL, 120 mmol) is then added, drop-by-drop, at 0° C. The solution is stirred for 2 hours at room temperature, then is dripped, drop-by-drop, on a 1:1 (v/v) mixture of diisopropyl ether/water, while stirring (360 mL). After stirring for 2 hours, the heterogeneous mixture is allowed to stand overnight. The white precipitate is recovered by filtration, washed successively with IPE (2×30 mL) then with water (2×30 mL). The solid obtained is solubilized in water (200 mL), adjusting the pH to 7 by adding an aqueous solution of 1 N soda. Water (65 mL) is added. The mixture is filtered through a 0.45 μm filter, then purified by ultrafiltration against a 0.9% NaCl solution and then water until the conductimetry of the permeate is less than 50 μS/cm. The co-polyamino acid solution is then concentrated to about theoretical 25 g/L, the pH is adjusted to 7 and the aqueous solution is filtered through 0.2 μm. This solution is diluted with water and acetone in order to obtain a 12 g/L solution containing 30% acetone mass, then it is filtered through an activated carbon filter (3 M R53 SLP). The acetone is distilled (40° C., 100 mbar) and the solution is purified by ultrafiltration against a 0.9% NaCl solution %, then water, until the conductimetry of the permeate is less than 50 μS/cm. The co-polyamino acid solution is then concentrated and the pH is adjusted to 7. The aqueous solution is filtered through 0.2 am and stored at 4° C.

Dry extract: 17.8 mg/g
DP (estimated using RMN $^1$H): 26
According to RMN $^1$H: i=0.038
The calculated average molar mass of co-polyamino acid B1 is 4994 g/mol.
Organic HPLC-SEC (calibration): Mn=2800 g/mol Co-Polyamino Acid B2: Sodium Poly-L-Glutamate Modified by Molecule A2 Whose Esters are Saponified and Having a Number-Average Molar Mass (Mn) of 5200 g/mol Co-Polyamino Acid B2-1: Poly-L-Glutamic Acid Derived from the Polymerization of γ-Benzyl-L-Glutamate N-Carboxyanhydride Initiated by Hexylamine In a jacketed reactor, γ-benzyl-L-glutamate N-carboxyanhydride (500 g, 1.90 mol) is solubilized in anhydrous DMF (1100 mL). The mixture is then stirred until completely dissolved, cooled to 0° C., then hexylamine (6.27 mL, 47.5 mmol) is quickly introduced. The mixture is stirred at 0° C. for 5 hours, from 0° C. to 20° C. for 7 hours, then at 20° C. for 7 hours. The reaction medium is then heated to 65° C. for 2 hours, cooled to 55° C. and methanol (3300 mL) is introduced over 1 h 30. The reaction mixture is then cooled to 0° C. and stirred for 18 hours. The white precipitate is recovered by filtration, washed with diisopropyl ether (2×800 mL), then dried under reduced pressure at 30° C. resulting in a poly(gamma-benzyl-L-glutamic) acid (PBLG).

To a solution of PBLG (180 g) in N,N-dimethylacetamide (DMAc, 450 mL) is added Pd/Al$_2$O$_3$ (36 g) under an argon atmosphere. The mixture is placed under a hydrogen atmosphere (10 bar) and stirred at 60° C. for 24 hours. After cooling to room temperature and filtration of the catalyst on P4 sintered, then filtration through a 0.2 m Omnipore hydrophilic PTFE membrane, a solution of water at pH 2 (2700 mL) is poured, drop-by-drop over the DMAc solution over a period of 45 minutes while stirring. After stirring for 18 hours, the white precipitate is recovered by filtration, washed with water (4×225 mL) then dried under reduced pressure at 30° C.

Co-Polyamino Acid B2

Co-polyamino acid B2-1 (15.0 g) is solubilized in DMF (230 mL) at 40° C., then N-methyl morpholine (NMM, 11.57 g, 114.4 mmol) is added. At the same time, molecule A2 in the form of a hydrochloride salt (10.17 g, 17.2 mmol) is suspended in DMF (250 mL) and triethylamine (2.39 mL, 17.2 mmol) is added, then the mixture is slightly heated while stirring until it is completely dissolved. To the co-polyamino acid solution, cooled to 25° C., are successively added the solution of molecule A2, N-oxide of 2-hydroxy pyridine (HOPO, 3.81 g, 34.3 mmol) then EDC (6.58 g, 34.3 mmol). The reaction medium is stirred at 25° C. for 2 hours, filtered through a 0.2 mm woven filter and dripped, drop-by-drop, over 2.6 of water containing 15% NaCl by mass and HCl (pH 2) while stirring. At the end of the addition, the pH is readjusted to 2 with a 1 N HCl solution and the suspension is left to stand overnight. The precipitate is collected by filtration, then rinsed with 2×100 mL of water. The white solid obtained is solubilized in 1.2 L of water by slow addition of an aqueous solution of NaOH 1 N up to a pH of 7, while stirring, then the solution is filtered through a 0.45 am filter. Ethanol (30% by mass) is added, then the solution is filtered through an activated carbon filter (3 M R53 SLP). A solution of 10 N NaOH is slowly added while stirring up to a pH of 13, then the mixture is stirred for 2 hours. After neutralization to a pH of 7 by adding a solution of 37% HCl, the clear solution obtained is purified by ultrafiltration against a solution of 0.9% NaCl then water, until the conductimetry of the permeate is less than 50 μS/cm. The co-polyamino acid solution is then concentrated and the pH is adjusted to 7. The aqueous solution is filtered through 0.2 am and stored at 4° C.

Dry extract: 22.6 mg/g
DP (estimated using RMN $^1$H): 40
According to RMN $^1$H: i=0.15
The calculated average molar mass of co-polyamino acid B2 is 9301 g/mol.
Organic HPLC-SEC (PEG calibration): Mn=5200 g/mol.

Co-Polyamino Acid B3: Sodium Poly-L-Glutamate Modified by Molecule A3 Whose Ester is Saponified and Having a Number-Average Molar Mass (Mn) of 4900 g/mol Co-polyamino acid B2-1 (12.0 g) is solubilized in DMF (92 mL) at 40° C., then N-methyl morpholine (NMM, 9.25 g, 91.5 mmol) is added. At the same time, a solution of molecule A3 in the form of a hydrochloride salt (7.51 g, 13.7 mmol) and N,N-diisopropylethylamine (DIPEA, 2.39 mL, 13.7 mmol) in DMF (27 mL) is prepared. To the co-polyamino acid solution, cooled to 25° C., are successively added, the solution of molecule A3, N-oxide of 2-hydroxy pyridine (HOPO, 3.05 g, 27.4 mmol). The mixture is cooled to 0° C., then EDC (5.26 g, 27.4 mmol) is added. After 5 minutes at 0° C., the reaction medium is stirred at 25° C. for 2 hours, filtered through a 0.2 mm woven filter and dripped, drop-by-drop, over 950 L of water containing 15% NaCl by mass and HCl (pH 2) while stirring. At the end of this addition, the pH is readjusted to 2 with a solution of 1 N HCl and the suspension is allowed to stand overnight. The precipitate is collected by filtration, then rinsed with 3×100 mL of water. The white solid obtained is solubilized in 1 L of water by the slow addition of an aqueous solution of 1 N NaOH to a pH of 7, while stirring. Once solubilization is complete, the pH is adjusted to pH 12 over 2 hours, then to pH 13 over 1 hour, by adding a solution of 10 N NaOH. After neutralization to pH 7 by adding a solution of 37% HCl, this solution is diluted with water and ethanol in order to obtain a 12 g/L solution containing 30% ethanol by mass, then it is filtered through an activated carbon filter (3 M R53 SLP). The solution obtained is filtered through a 0.45 μm filter, then purified by ultrafiltration against a 0.9% solution of NaCl, then water, until the conductimetry of the permeate is less than 50 μS/cm. The co-polyamino acid solution is then concentrated and the pH is adjusted to 7. The aqueous solution is filtered through 0.2 μm and stored at 4° C.

Dry extract: 20.6 mg/g
DP (estimated using RMN $^1$H): 40
According to RMN $^1$H: i=0.15

The calculated average molar mass calculated of co-polyamino acid B3 is 8977 g/mol.

Organic HPLC-SEC (PEG calibration): Mn=4900 g/mol.

Co-Polyamino Acid B4: Sodium Poly-L-Glutamate Modified by Molecule A4 Whose Ester is Saponified and with a Number-Average Molar Mass (Mn) of 4700 g/mol Using a process similar to the one used for the preparation of co-polyamino acid B3 applied to the hydrochloride salt of molecule A4 (7.12 g, 13.7 mmol) and to co-polyamino acid B2-1 (12.0 g), a sodium poly-L-glutamate modified by molecule A4 for which the ester is saponified is obtained.

Dry extract: 19.4 mg/g
DP (estimated using RMN $^1$H): 40
According to RMN $^1$H: i=0.15

The calculated average molar mass calculated of co-polyamino acid B4 is 8809 g/mol.

Organic HPLC-SEC (PEG calibration): Mn=4700 g/mol.

Co-Polyamino Acid B5: Sodium Poly-L-Glutamate Modified by Molecule A5 Whose Ester is Saponified and Having a Number-Average Molar Mass (Mn) of 5400 g/mol Using a process similar to the one used for the preparation of co-polyamino acid B3 applied to the hydrochloride salt of molecule A5 (9.71 g, 13.7 mmol) and to co-polyamino acid B2-1 (12.0 g), a sodium poly-L-glutamate modified by molecule A5 for which the ester is saponified is obtained.

Dry extract: 20.8 mg/g
DP (estimated using RMN $^1$H): 40
According to RMN $^1$H: i=0.15

The calculated average molar mass of co-polyamino acid B5 is 9939 g/mol.

Organic HPLC-SEC (PEG calibration): Mn=5400 g/mol.

Co-Polyamino Acid B7: Sodium Poly-L-Glutamate Modified at One of its Ends by Molecule A7 and Having a Number-Average Molar Mass (Mn) of 2500 g/mol Using a process similar to the one used for the preparation of co-polyamino acid B1 applied to molecule A7 (2.50 g, 2.74 mmol) and to γ-benzyl-L-glutamate N-carboxyanhydride (15.89 g, 60.4 mmol), a sodium poly-L-glutamate modified at one of its ends by molecule A7 is obtained.

Dry extract: 20.3 mg/g
DP (estimated using RMN $^1$H): 26
According to RMN $^1$H: i=0.038

The calculated average molar mass of co-polyamino acid B7 is 3893 g/mol.

Organic HPLC-SEC (PEG calibration): Mn=2500 g/mol

Co-Polyamino Acid B13: Sodium Poly-L-Glutamate Modified at One of its Ends by Molecule a11, Whose Esters are Deprotected and Having a Number-Average Molar Mass (Mn) of 3000 g/mol In a jacketed reactor, γ-benzyl-L-glutamate N-carboxyanhydride (24.50 g, 93.05 mmol) is solubilized in anhydrous DMF (55 mL). The mixture is then stirred until completely dissolved, cooled to 0° C., then hexylamine (0.56 mL, 4.23 mmol) is quickly introduced. The mixture is stirred at 0° C. for 48 hours, then, successively, a solution of molecule A11 (9.51 g, 5.08 mmol) in DMF (50 mL), HOPO (564 mg, 5.08 mmol) and EDC (973 mg, 5.08 mmol) are added. The reaction medium is stirred at 0° C. for 1 hour, between 0° C. and 20° C. for 2 hours, then at 20° C. for 16 hours. This solution is then poured over a 1:1 H$_2$O/MeOH mixture (10 V) at room temperature and while stirring. After stirring for 4 hours, the white precipitate is recovered by filtration, washed with diisopropyl ether (2×100 mL), water (2×100 mL) and a 1:1 H$_2$O/MeOH mixture (2×100 mL).

The solid obtained is solubilized in TFA (220 mL) and stirred at room temperature for 2 hours 30 minutes. This solution is then poured into water (10 V) at room temperature and while stirring. After 2 hours 30 minutes hours of stirring, the white precipitate is recovered by filtration, washed with water (2×200 mL) then dried under reduced pressure.

The solid obtained is solubilized in N,N-dimethylacetamide (DMAc, 210 mL), then Pd/Al$_2$O$_3$ (2.1 g) is added under an argon atmosphere. The mixture is placed under a hydrogen atmosphere (6 bar) and stirred at 60° C. for 24 hours. After cooling to room temperature and filtration of the catalyst on sintered P4, then through Omnipore 0.2 m PTFE hydrophilic membrane, a solution of water at pH 2 containing 15% de NaCl (6 V) is poured, drop-by-drop over the DMAc solution over a period of 45 minutes and while stirring. After 18 hours of stirring, the white precipitate is recovered by filtration, washed with water then dried under reduced pressure. The solid obtained is solubilized in water (600 mL), adjusting the pH to 7 by adding an aqueous solution of 1 N soda. The pH is then adjusted to pH 12 and the solution is stirred for 1 hour. After neutralization to pH 7, the solution is filtered through 0.2 am, diluted with ethanol in order to obtain a solution containing 30% by mass of ethanol, then filtered through an activated carbon filter (3 M R53 SLP). The solution obtained is filtered through a 0.45 am filter and purified by ultrafiltration against a 0.9% solution of NaCl, then water, until the conductimetry of the permeate is less than 50 μS/cm (3 M R53 SLP). The co-polyamino acid solution is then concentrated and the pH is adjusted to 7. The aqueous solution is filtered through 0.2 am and stored at 4° C.

Dry extract: 23.5 mg/g
DP (estimated by RMN $^1$H)=24 therefore i=0.042

The calculated average molar mass of co-polyamino acid B13 is 5377 g/mol.

Organic HPLC-SEC (PEG calibration): Mn=3000 g/mol.

Co-Polyamino Acid B14: Sodium Poly-L-Glutamate Modified at One of its Ends by Molecule A12, for which the Esters are Deprotected and with a Number-Average Molar Mass (Mn) of 3300 g/mol Co-Polyamino Acid B14-1: Poly-L-Benzyl Glutamate Modified at One of its Ends by Molecule A12.

γ-benzyl-L-glutamate N-carboxyanhydride (50.00 g, 189.39 mmol) is solubilized in a previously oven-dried receiving flask in anhydrous DMF (65 mL). The mixture is then stirred until completely dissolved, cooled to 0° C., then a solution of molecule A12 (9.65 g, 8.63 mmol) in DMF (50 mL) is introduced quickly. The mixture is stirred from 0° C. to room temperature for 2 hours, then heated to 65° C. for 2 hours. The reaction medium is cooled to room temperature and poured, drop-by-drop into diisopropylether (1.8 L) while stirring. The white precipitate is recovered by filtration, washed twice with diisopropylether then vacuum dried at 30° C., resulting in a white solid.

Co-Polyamino Acid B14

The co-polyamino acid B14-1 is solubilized in (DMAc, 250 mL) then Pd/Al$_2$O$_3$ (5.0 g) is added in an atmosphere of argon. The mixture is placed in a hydrogenic atmosphere (10 bar) and stirred at 60° C. for 24 hours. After cooling to room temperature and sinter catalyzer filtration P4, then filtration by Omnipore 0.2 μm PTFE hydrophilic membrane, a solution of water at pH 2 (6 V) is run, drop-by-drop over the DMAc solution over a period of 45 minutes and while stirring. After 18 hours of stirring, the white precipitate is recovered by filtration, washed with water then dried under reduced pressure. The solid obtained is solubilized in water (1.25 L), adjusting the pH to 7 by adding an aqueous solution of 1 N soda. The pH is then adjusted to pH 13 and the solution is stirred for 3 hours. After neutralization to a pH of 7, the solution is filtered by 0.2 μm, diluted with ethanol, resulting in a solution containing 30% by mass of ethanol, then filtered through an activated carbon filter (3 M R53 SLP). The solution obtained is filtered by a 0.45 m filter, then purified by ultra-filtration against a 0.9% solution of NaCl, then water, until the conductimetry of the permeate is less than 50 μS/cm (3 M R53 SLP). The co-polyamino acid solution is then concentrated and the pH is adjusted to 7. The aqueous solution is filtered through 0.2 μm and stored at 4° C.

Dry extract: 25.7 mg/g
DP (estimated by RMN $^1$H)=24 therefore i=0.042

The calculated average molar mass of co-polyamino acid B14 is 4720 g/mol.

Organic HPLC-SEC (PEG calibration): Mn=3300 g/mol.

Co-Polyamino Acid B15: Sodium Poly-L-Glutamate Modified by Molecule A13 Whose Esters are Deprotected and Having a Number-Average Molar Mass (Mn) of 4400 g/mol Using a process similar to the one used for the preparation of co-polyamino acid B3 applied to the hydrochloride salt of molecule A13 (3.39 g, 2.34 mmol) and to co-polyamino acid B2-1 (2.04 g), with a saponification step at pH 13 for 5 hours in a water mixture containing 30% by mass of ethanol, a sodium poly-L-glutamate modified by molecule A13 whose esters are deprotected is obtained.

Dry extract: 15.7 mg/g
DP (estimated using RMN $^1$H): 40
According to RMN $^1$H: i=0.15

The calculated average molar mass of co-polyamino acid B15 is 12207 g/mol.

Organic HPLC-SEC (PEG calibration): Mn=4400 g/mol.

Co-Polyamino Acid B17: Sodium Poly-L-Glutamate Modified at One of its Ends by Molecule A15, Whose Esters are Deprotected and with a Number-Average Molar Mass (Mn) of 1000 g/mol Using a process similar to the one used for the preparation of co-polyamino acid B14 applied to molecule A15 (10.85 g, 8.74 mmol) and to γ-benzyl-L-glutamate N-carboxyanhydride (23.00 g, 87.37 g), with a saponification step at pH 12 for 2 hours, a sodium poly-L-glutamate modified at one of its ends by molecule A15, for which the esters are deprotected, is obtained.

Dry extract: 23.9 mg/g
DP (estimated using RMN $^1$H): 10
According to RMN $^1$H: i=0.1

The calculated average molar mass of co-polyamino acid B17 is 2576 g/mol.

Aqueous HPLC-SEC (PEG calibration): Mn=1000 g/mol.

Co-Polyamino Acid B18: Sodium Poly-L-Glutamate Modified by Molecule A16, for which the Esters are Deprotected and with a Number-Average Molar Mass (Mn) of 5000 g/mol Using a process similar to the one used for the preparation of co-polyamino acid B3 applied to molecule A16 (31.06 g, 42.08 mmol) and to co-polyamino acid B2-1 (36.80 g), a beige solid is obtained after the acid precipitation step. This solid is diluted in TFA (100 g/L) and the mixture is stirred at room temperature for 3 hours. The solution is then poured, drop-by-drop, over water (3 V) while stirring. After stirring for 16 hours, the precipitate is recovered by filtration then washed with water. The solid obtained is solubilized in water, adjusting the pH to 7 by adding an aqueous solution of 10 N soda. Once solubilization is complete, the pH is adjusted to pH 12 for 1 hour by adding a solution of 1 N NaOH. After neutralization to pH 7, by adding a 1 N HCl solution, the product is purified by a process similar to that used for the preparation of co-polyamino acid B3 (carbofiltration and ultrafiltration). A sodium poly-L-glutamate modified by molecule A16 with deprotected esters is obtained.

Dry extract: 28.2 mg/g
DP (estimated using RMN $^1$H): 40
According to RMN $^1$H: i=0.15

The calculated average molar mass of co-polyamino acid B18 is 9884 g/mol.

Organic HPLC-SEC (PEG calibration): Mn=5000 g/mol.

Co-Polyamino Acid B19: Sodium Poly-L-Glutamate Modified by Molecule A17, f Whose Esters are Deprotected and with a Number-Average Molar Mass (Mn) of 4900 g/mol Using a process similar to the one used for the preparation of co-polyamino acid B3 applied to the hydrochloride salt of molecule A17 (7.35 g, 13.09 mmol) and to co-polyamino acid B2-1 (11.45 g), with a saponification step at pH 13 for 3 hours in a water mixture containing 30% by mass of ethanol, a sodium poly-L-glutamate modified by molecule A17 whose esters are deprotected is obtained.

Dry extract: 25.7 mg/g
DP (estimated using RMN $^1$H): 40
According to RMN $^1$H: i=0.15

The calculated average molar mass of co-polyamino acid B19 is 9062 g/mol.

Organic HPLC-SEC (PEG calibration): Mn=4900 g/mol.

Co-Polyamino Acid B20: Sodium Poly-L-Glutamate Modified by Molecule A18, Whose Esters are Deprotected and with a Number-Average Molar Mass (Mn) of 5800 g/mol Using a process similar to the one used for the preparation of co-polyamino acid B3 applied to the hydrochloride salt of molecule A18 (5.43 g, 6.86 mmol) and to co-polyamino acid B2-1 (6.00 g), with a saponification step at pH 13 for 3 hours in a water mixture containing 30% by mass of ethanol, a sodium poly-L-glutamate modified by molecule A18 whose esters are deprotected is obtained.

Dry extract: 22.0 mg/g
DP (estimated using RMN $^1$H): 40
According to RMN $^1$H: i=0.15

The calculated average molar mass of co-polyamino acid B20 is 10444 g/mol.

Organic HPLC-SEC (PEG calibration): Mn=5800 g/mol.

Co-Polyamino Acid B21: Sodium Poly-L-Glutamate Modified by Molecule A19, for which the Esters are Deprotected and with a Number-Average Molar Mass (Mn) of 5000 g/mol Using a process similar to the one used for the preparation of co-polyamino acid B18 applied to molecule A19 (32.64 g, 45.97 mmol) and to co-polyamino acid B2-1 (40.20 g), a sodium poly-L-glutamate modified by molecule A19 whose esters are deprotected is obtained.

Dry extract: 26.2 mg/g
DP (estimated using RMN $^1$H): 40
According to RMN $^1$H: i=0.15

The calculated average molar mass of co-polyamino acid B21 is 9716 g/mol.

Organic HPLC-SEC (PEG calibration): Mn=5000 g/mol.

Co-Polyamino Acid B22: Sodium Poly-L-Glutamate Modified at One of its Ends by Molecule A20 and with a Number-Average Molar Mass (Mn) of 1900 g/mol Using a process similar to the one used for the preparation of co-polyamino acid B14 applied to molecule A20 (13.28 g, 12.51 mmol) in CHCl$_3$ (53 mL) and to γ-benzyl-L-glutamate N-carboxyanhydride (72.46 g, 275.2 mmol) in DMF (270 mL), with a saponification step at pH 12 for 1 hour 30 minutes, a sodium poly-L-glutamate, modified at one of its ends by molecule A20, is obtained.

Dry extract: 27.3 mg/g
DP (estimated using RMN $^1$H): 20
According to RMN $^1$H: i=0.05

The calculated average molar mass of co-polyamino acid B22 is 4087 g/mol.

Aqueous HPLC-SEC (PEG calibration): Mn=1900 g/mol.

ii) Co-Polyamino Acids According to Formulas XXXa, XXXb and XXXb', XXXb"

| No. | CO-POLYAMINO ACIDS BEARING CARBOXYLATE CHARGES AND HYDROPHOBIC RADICALS |
|---|---|
| B7 | 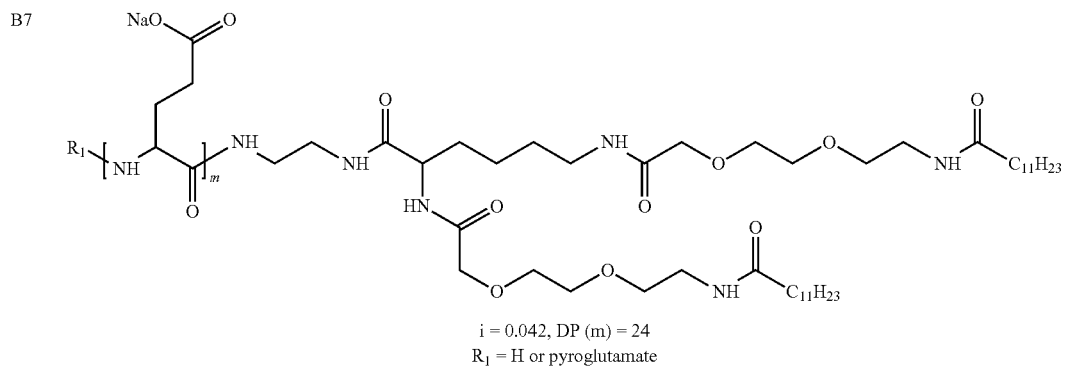 | i = 0.042, DP (m) = 24
R$_1$ = H or pyroglutamate

| B8 | 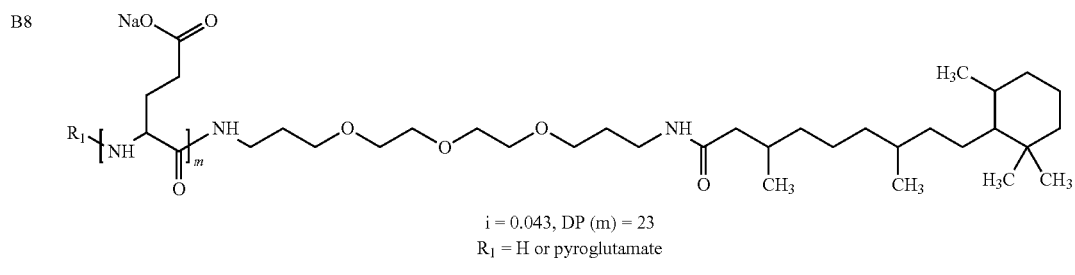 |
|---|---| i = 0.043, DP (m) = 23
R$_1$ = H or pyroglutamate

| B10 | 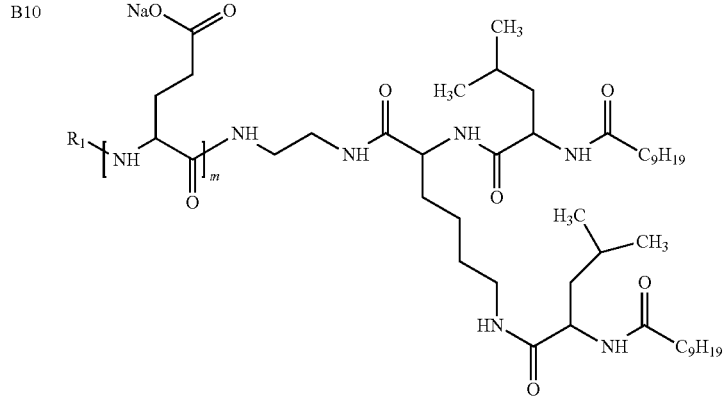 |
|---|---| i = 0.032, DP (m) = 31
R$_1$ = H or pyroglutamate

| No. | CO-POLYAMINO ACIDS BEARING CARBOXYLATE CHARGES AND HYDROPHOBIC RADICALS |
|---|---|
| B11 | 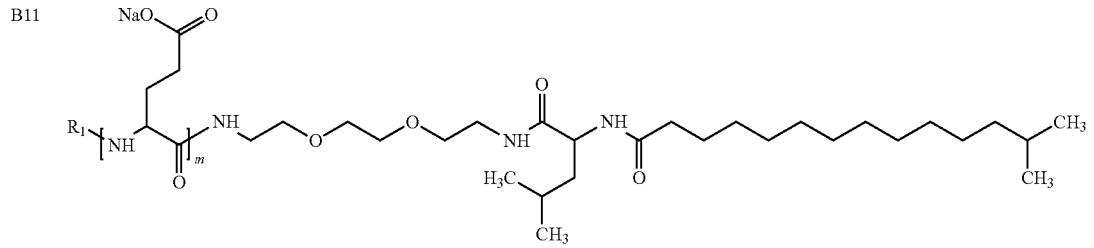<br>i = 0.034, DP (m) = 29<br>R₁ = H or pyroglutamate |
| B12 | 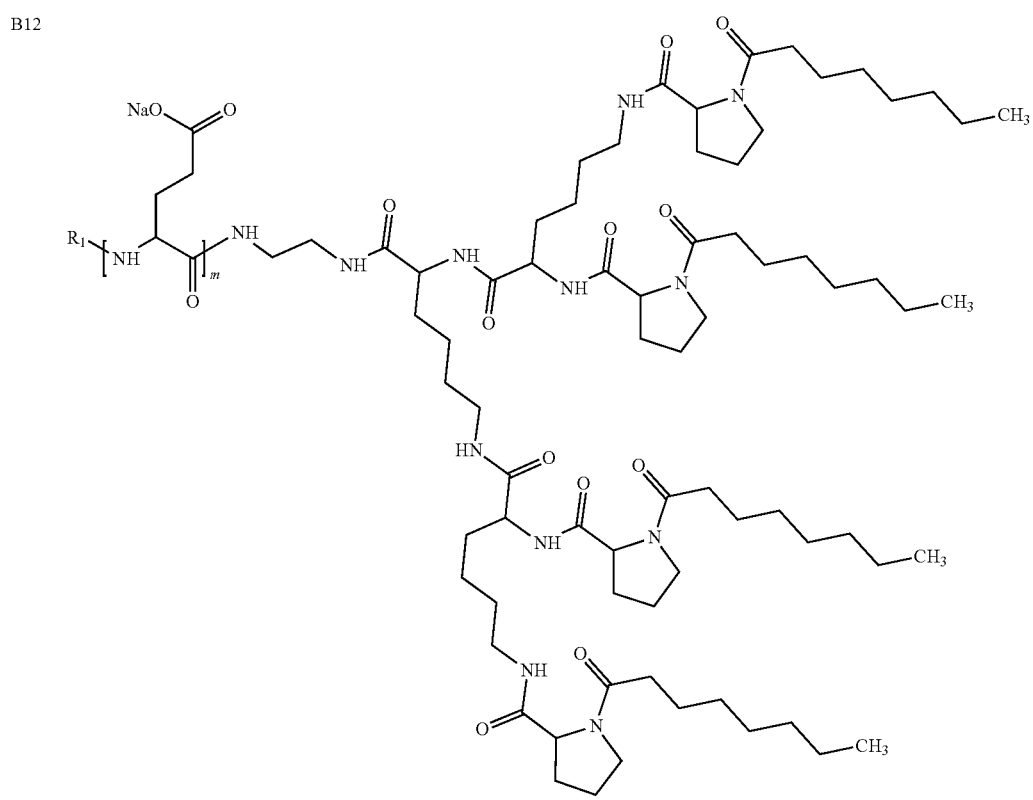<br>i = 0.042, DP (m) = 24<br>R₁ or pyroglutamate |

Co-Polyamino Acid B7': Sodium Poly-L-Glutamate Modified at One of its Ends by Molecule A5a and with a Number-Average Molar Mass (Mn) of 2600 g/mol Co-Polyamino Acid B7'-1: Poly-L-Benzylglutamate Modified at One of its Ends by Molecule A5a.

γ-benzyl-L-glutamate N-carboxyanhydride (10.1 g, 38.4 mmol) is solubilized in a previously oven-dried receiving flask in anhydrous DMF (19 mL). The mixture is then stirred until completely dissolved, cooled to 0° C., then a solution of molecule A5a (1.47 g, 1.74 mmol) in chloroform (3.7 mL) is introduced quickly. The mixture is stirred from 0° C. to room temperature for 2 hours, then heated to 65° C. for 2 hours. The reaction medium is cooled to room temperature and poured, drop-by-drop into diisopropyl ether (0.29 mL) while stirring. The white precipitate is recovered by filtration, washed twice with diisopropyl ether (5×50 mL) then vacuum dried at 30° C., resulting in a white solid.

Co-Polyamino Acid B7'

Co-polyamino acid B7'-1 (8.33 g, 33.0 mmol) is diluted in trifluoracetic acid (TFA, 132 mL), then the solution is cooled to 4° C. A 33% HBr solution in acetic acid (92.5 mL, 0.528 mol) is then added, drop-by-drop. The mixture is stirred at room temperature for 2 hours, then poured, drop-by-drop over a 1:1 (v/v) mixture of diisopropylether and water, while stirring (0.8 L). After stirring for 2 hours, the heterogeneous mixture is allowed to stand overnight. The white precipitate is recovered by filtration, washed with IPE (2×66 mL) then with water (2×66 mL). The solid obtained is then solubilized in water (690 mL) while adjusting the pH to 7 by adding an aqueous 1 N soda solution. After solubilization, the theoretical concentration is adjusted to theoretical 20 g/L by adding water (310 mL), the solution is filtered through a 0.45 µm filter, then purified by ultrafiltration against a solution of 0.9% NaCl, then water, until the conductimetry of the permeate is less than 50 µS/cm. The solution obtained is filtered through a 0.2 µm filter and stored at 2-8° C.

Dry extract: 17.3 mg/g
DP (estimated using RMN $^1$H): 24
According to RMN $^1$H: i=0.042
The calculated average molar mass of co-polyamino acid B7' is 4430 g/mol.
Organic HPLC-SEC (PEG calibration): Mn=2600 g/mol.

Example B8: Co-Polyamino Acid B8—Sodium Poly-L-Glutamate Modified at One of its Ends by the Molecule A6a and Having a Number-Average Molar Mass (Mn) of 2400 g/mol Co-Polyamino Acid B8-1: Poly-L-Benzylglutamate Modified at One of its Ends by Molecule A6.

γ-benzyl-L-glutamate N-carboxyanhydride (19.0 g, 72.2 mmol) is solubilized in a previously oven-dried receiving flask in anhydrous DMF (19 mL). The mixture is then stirred until completely dissolved, cooled to 0° C., then a solution of molecule A6a (1.68 g, 3.28 mmol) in chloroform (3.7 mL) is introduced quickly. The mixture is stirred from 0° C. to room temperature for 2 hours, then heated to 65° C. for 2 hours. The reaction medium is cooled to room temperature and poured, drop-by-drop into diisopropyl ether (0.29 L) while stirring. The white precipitate is recovered by filtration, washed twice with diisopropyl ether (5×50 mL) then vacuum dried at 30° C., resulting in a white solid.
Co-Polyamino Acid B8

Using a process similar to the one used for the preparation of co-polyamino acid B7' applied to co-polyamino acid B8-1 (14.6 g, 61.5 mmol), a sodium poly-L-glutamate modified at one of its ends by molecule A6a is obtained.

Dry extract: 21.3 mg/g
DP (estimated using RMN $^1$H): 23
According to RMN $^1$H: i=0.043
The calculated average molar mass of co-polyamino acid B8 is 3948 g/mol.
Organic HPLC-SEC (PEG calibration): Mn=2400 g/mol.
Co-Polyamino Acid B10: Sodium Poly-L-Glutamate Modified at One of its Ends by Molecule A8 and with a Number-Average Molar Mass (Mn) of 3100 g/mol
Co-Polyamino Acid B10-1: Poly-L-Benzylglutamate Modified at One of its Ends by Molecule A8.

In an appropriate container, are successively introduced the hydrochloride salt of molecule A8 (2.308 g, 3.04 mmol), chloroform (120 mL), molecular sieve 4 Å (1.5 g), as well as the exchange resin of Amberlite IRN 150 ion (1.5 g). After 1 hour of coil stirring, the medium is filtered and the resin is rinsed with chloroform. The mixture is evaporated, then co-evaporated with toluene. The residue is solubilized in anhydrous DMF (40 mL) to be used directly in the polymerization reaction.

γ-benzyl-L-glutamate N-carboxyanhydride (20.0 g, 76.0 mmol) is solubilized in a previously oven-dried receiving flask in anhydrous DMF (19 mL). The mixture is then stirred until completely dissolved, cooled to 0° C., then a solution of molecule A8, previously prepared, in chloroform (3.7 mL) is introduced quickly. The mixture is stirred from 0° C. to room temperature for 2 hours, then heated to 65° C. for 2 hours. The reaction medium is then cooled to room temperature and poured, drop-by-drop into diisopropyl ether (0.29 mL) while stirring. The white precipitate is recovered by filtration, washed twice with diisopropyl ether (5×50 mL) then vacuum dried at 30° C., resulting in a white solid.
Co-Polyamino Acid B10

Using a process similar to the one used for the preparation of co-polyamino acid B7' applied to co-polyamino acid B10-1 (15.2 g, 60.8 g), a sodium poly-L-glutamate modified at one of its ends by molecule A8 is obtained.

Dry extract: 34.1 mg/g
DP (estimated using RMN $^1$H): 31
According to RMN $^1$H: i=0.032
The calculated average molar mass of co-polyamino acid B10 is 5367 g/mol.
Organic HPLC-SEC (PEG calibration): Mn=3100 g/mol.

Example B11: Co-Polyamino Acid B11—Sodium Poly-L-Glutamate Modified at One of its Ends by Molecule A9 and with a Number-Average Molar Mass (Mn) of 3000 g/mol Co-Polyamino Acid B11-1: Poly-L-Benzylglutamate Modified at One of its Ends by Molecule A9.

In a suitable container, are successively introduced hydrochloride salt of molecule A9 (2.023 g, 3.87 mmol), chloroform (120 mL), molecular sieve 4 Å (1.5 g), as well as the exchange resin of Amberlite IRN 150 ion (1.5 g). After 1 hour of coil stirring, the medium is filtered and the resin is rinsed with chloroform. The mixture is evaporated, then co-evaporated with toluene. The residue is solubilized in anhydrous DMF (40 mL) to be used directly in the polymerization reaction.

Using a process similar to the one used for the preparation of co-polyamino acid B8-1 applied to the solution of molecule A9, previously prepared, and to γ-benzyl-L-glutamate N-carboxyanhydride (25.5 g, 96.8 mmol), co-polyamino acid B11-1 is obtained.
Co-Polyamino Acid B11

Using a process similar to the one used for the preparation of co-polyamino acid B7' applied to co-polyamino acid B11-1 (18.4 g, 77.3 g), a sodium poly-L-glutamate modified at one of its ends by molecule A9 is obtained.

Dry extract: 28.0 mg/g
DP (estimated using RMN $^1$H): 29
According to RMN $^1$H: i=0.034
The calculated average molar mass of co-polyamino acid B11 is 4828 g/mol.
Organic HPLC-SEC (PEG calibration): Mn=3000 g/mol.
Co-Polyamino Acid B12: Sodium Poly-L-Glutamate Modified at One of its Ends by Molecule A10 and with a Number-Average Molar Mass (Mn) of 2700 g/mol
Co-Polyamino Acid B12-1: Poly-L-Benzylglutamate Modified at One of its Ends by Molecule A10.

Using a process similar to the one used for the preparation of co-polyamino acid B10-1 applied to the solution of molecule A10 (3.0 g, 2.24 mmol), and to γ-benzyl-L-glutamate N-carboxyanhydride (12.99 g, 49.3 mmol), co-polyamino acid B12-1 is obtained.
Co-Polyamino Acid B12

Using a process similar to the one used for the preparation of co-polyamino acid B7' applied to co-polyamino acid B12-1 (13.2 g, 48.0 mmol), a sodium poly-L-glutamate modified at one of its ends by molecule A10 is obtained.

Dry extract: 13.2 mg/g
DP (estimated using RMN $^1$H): 24
According to RMN $^1$H: i=0.042
The calculated average molar mass of co-polyamino acid B12 is 4924 g/mol.
Organic HPLC-SEC (PEG calibration): Mn=2700 g/mol.

Part CE—Co-Polyamino Acids Counter-Examples
| No. | |
|---|---|
| CE1 | 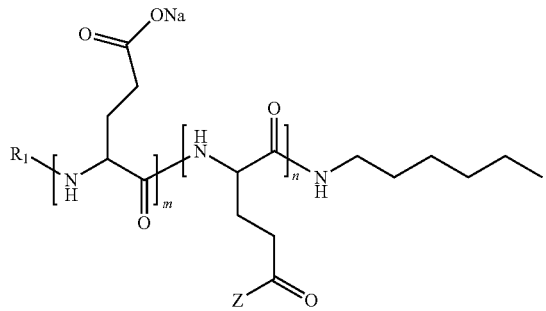
i = 0.05, DP (m + n) = 22
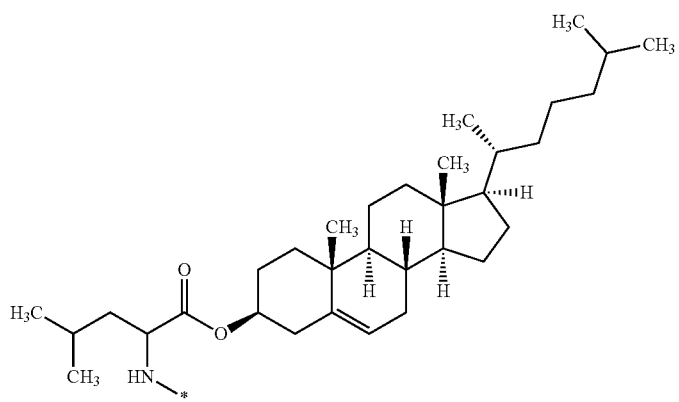
Z =
$R_1$ = $CH_3$—CO——, H or pyroglutamate |
| CE2 | 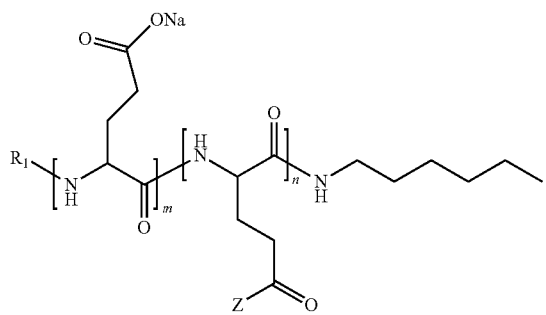
i = 0.05, DP (m + n) = 43
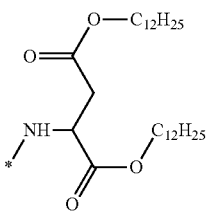
Z =
$R_1$ = $CH_3$—CO——, H or pyroglutamate |

Co-polyamino acids CE1 and CE2 are synthesized using the process described in patent application WO2017211916.

Part C—Compositions

Example C: Fast-Acting Insulin Analog Solution (Humalog®) at 100 U/mL

This solution is a commercial solution of insulin lispro, marketed by ELI LILLY under the name Humalog®. This product is a fast-acting insulin analog. The excipients in Humalog® are meta-cresol (3.15 mg/mL), glycerol (16 mg/mL), disodium phosphate (1.88 mg/mL), zinc oxide (to have 0.0197 mg of zinc ion/mL), sodium hydroxide and hydrochloric acid to adjust the pH (pH 7-7.8) and water.

Example C2: Fast-Acting Insulin Analog Lispro Solution at 100-600 U/mL

This is a solution of insulin prepared using insulin lispro powder produced by Gan & Lee. This product is a fast-acting insulin analog. The excipients used are m-cresol, glycerol, zinc oxide, sodium hydroxide and hydrochloric acid for the adjustment of pH (pH 7-7.8) and water. The concentration of zinc is 300 µM per 100 UI/mL of insulin. The concentration of the other excipients varies as a function of that of lispro in order to obtain the desired concentrations in the final formulations.

Example C3: Long-Acting Insulin Analog Solution (Lantus®) at 100 U/mL

This solution is a commercial solution of insulin glargine marketed by SANOFI under the name Lantus®. This product is a long-acting insulin analog. The excipients in Lantus® are zinc chloride (30 µg/mL), m-cresol (2.7 mg/mL), glycerol (20 mg/mL) polysorbate 20 (16 µM), sodium hydroxide and hydrochloric acid to adjust the pH (pH 4) and water.

Example C4: Solution of Insulin Glargine at 100-400 U/mL

This is a solution of insulin glargine prepared using insulin glargine powder produced by Gan & Lee. This product is a long-acting insulin analog. The excipients used are zinc chloride, m-cresol, glycerol, sodium hydroxide and hydrochloric acid for the adjustment of pH (pH 4) and water. The concentration of zinc is 460 µM per 100 UI/mL of insulin. The concentration of the other excipients varies as a function of that of glargine in order to obtain the desired concentrations in the final formulations.

Part CA—Compositions Comprising Insulin Glargine

Preparation process of CA1: Preparation of a diluted composition of co-polyamino/insulin glargine 50 U/mL at pH 7.1 according to a process using insulin glargine in liquid form (in solution) and a co-polyamino acid in liquid form (in solution)

To a parent solution of co-polyamino acid at pH 7.1 are added concentrated solutions of meta-cresol and glycerin in order to obtain a solution of co-polyamino acid of concentration $C_{parent\ co-polyamino\ acid/excipients}$ (mg/mL). The quantity of excipients added is adjusted so as to obtain a concentration of meta-cresol of 35 mM and glycerin of 184 mM in the composition of co-polyamino acid/insulin glargine 50 U/mL at pH 7.1.

In a sterile container, a volume $V_{insulin\ glargine}$ of a solution of insulin glargine at a concentration of 100 U/mL described in C3 or C4 is added to a volume $V_{parent\ co-polyamino\ acid/excipients}$ of a solution of co-polyamino acid at a concentration of $C_{parent\ co-polyamino\ acid/excipients}$ (mg/mL) so as to obtain a diluted co-polyamino acid composition $C_{diluted\ co-polyamino\ acid}$ (mg/mL)/insulin glargine 50 U/mL at pH 7.1. A turbidity appears. The pH is adjusted to 7.1 by adding concentrated NaOH and the solution is placed in stasis at 40° C. for 2 hours until complete solubilization. This visually clear solution is placed at 4° C.

Preparation Process CA2: Preparation of a Concentrated Co-Polyamino Acid/Insulin Glargine Composition at pH 7.1 Using a Co-Polyamino Acid, According to a Concentration Process of a Diluted Composition.

A composition of co-polyamino/insulin glargine 50 U/mL at pH 7.1 described in example CA1 is concentrated by ultrafiltration through a 3 kDa membrane of regenerated cellulose (Amicon® Ultra-15 marketed by Millipore). At the end of this ultrafiltration step, the retentate is clear and the concentration of insulin glargine in the composition is determined by reverse phase chromatography (RP-HPLC). The concentration of insulin glargine in the composition is then adjusted to the desired value by dilution in a solution of excipients m-cresol/glycerin/Tween 20 so as to obtain a final m-cresol concentration of 35 mM, Tween 20 of 52 µM and an osmolarity of 300 mOsm/kg. The pH is measured and adjusted to pH 7.1 by adding NaOH and concentrated HCl. This solution at pH 7.1, visually clear, has a concentration of insulin glargine $C_{insulin\ glargine}$ (U/mL) and a concentration of co-polyamino acid of $C_{co-polyamino\ acid}$ (mg/mL)= $C_{diluted\ co-polyamino\ acid}$ (mg/mL)×$C_{insu\ glargine}$ (U/mL)/50 (U/mL).

Preparation Process CA3: Preparation of a Concentrated Composition of Co-Polyamino/Insulin Glargine at pH 7.1 According to a Process Using Insulin Glargine in Liquid Form (in Solution) and a Co-Polyamino Acid in Liquid Form (in Solution)

To a parent solution of co-polyamino acid at pH 7.1 is added a solution of glargine at 220-400 UI/mL containing the excipients described in example C4. The concentration of excipients in the glargine solution is adjusted so as to obtain a meta-cresol concentration of 35 mM and glycerin of 184 mM in the co-polyamino acid/insulin glargine composition at pH 7.1. A turbidity appears. The pH is adjusted to 7.1 by adding concentrated NaOH and the solution is placed in stasis in an oven at 40° C. for 2 hours until complete solubilization. This visually clear solution is placed at 4° C. after the addition of one volume of concentrated solution of polysorbate 20 in order to obtain a final concentration of 52 µM.

Preparation Process CA3a: Preparation of a Composition of Co-Polyamino/Insulin Glargine at pH 7.1 According to a Process Using Insulin Glargine in Liquid Form (in Solution) and a Co-Polyamino Acid in Liquid Form (in Solution)

To a parent solution of co-polyamino acid at pH 7.0-7.5 is added a solution of glargine at 100-220 U/mL containing the excipients described in example C4. The concentrations of the excipients in the glargine solution are adjusted so as to obtain a meta-cresol concentration of 35 mM and glycerin of 230 mM in the co-polyamino acid/insulin glargine composition. A turbidity appears. The pH is adjusted to 7.5 by adding concentrated NaOH and the solution is placed in stasis in an oven at 40° C. for 2 hours until complete solubilization. The solution obtained is visually clear.

Preparation Process CA3b: Preparation of a Composition of Co-Polyamino/Insulin Glargine at pH 7.1 According to a Process Using Insulin Glargine in Liquid Form (in Solution) and a Co-Polyamino Acid in Liquid Form (in Solution)

To a parent solution of co-polyamino acid at pH 7.0-7.5 are added, in this order, a solution of sodium chloride and a solution of glargine at 100-220 U/mL described in example C4. The concentrations of the excipients in the glargine solution are adjusted so as to obtain a m-cresol concentration of 35 mM and glycerin of 230 mM in the co-polyamino acid/insulin glargine composition at pH 7.1. A turbidity appears. The pH is adjusted to 7.5 by adding concentrated NaOH and the solution is placed in stasis in an oven at 40° C. for 2 hours until complete solubilization. The solution obtained is visually clear.

According to the preparation processes CA2, CA3 or CA3a and CA3b, co-polyamino acid/insulin glargine compositions were prepared, for example, with insulin glargine concentrations from 100 U/mL to 300 U/mL.

Example CA4: Preparation of Co-Polyamino Acid/Insulin Glargine 200 U/mL Compositions at pH 7.1

Co-polyamino acid/insulin glargine 200 U/mL compositions are prepared according to the processes described in CA2 and CA3 so as to obtain an insulin glargine concentration of $C_{insulin\ glargine}$=200 U/mL and a co-polyamino acid concentration of $C_{co-polyamino\ acid}$ (mg/mL).
These compositions are presented in tables 1 and 1a.

TABLE 1

Compositions of insulin glargine (200 U/mL) in the presence of co-polyamino acid.

| Composition | Co-polyamino acid | Concentration of co-polyamino acid (mg/ml) | Insulin glargine (U/mL) | Visual appearance of the solution |
|---|---|---|---|---|
| CA3-1 | B7 | 5 | 200 | Clear |
| CA2-1 | B1 | 6 | 200 | Clear |
| CA3-2 | B9 | 5 | 200 | Clear |

TABLE 1a

Compositions of insulin glargine (200 U/mL) in the presence of co-polyamino acid B8.

| Composition | Co-polyamino acid | Concentration of co-polyamino acid (mg/ml) | Insulin glargine (U/mL) | Visual appearance of the solution |
|---|---|---|---|---|
| CA3-3 | B8 | 9 | 200 | Clear |
| CA3-4 | B7 | 17 | 200 | Clear |

The co-polyamino acids make it possible to solubilize the insulin glargine at neutral pH and to obtain a clear solution.
Preparation Process CA5: Protocol for the Determination of the Minimum Concentration for Solubilizing Insulin Glargine 50 U/mL at pH 7.1.

To a parent solution of co-polyamino acid at 7-7.5 pH are added concentrated m-cresol and glycerin solutions. The quantities of excipients added are adjusted so as to obtain a meta-cresol concentration of 35 mM and glycerin concentration of 184 mM in the co-polyamino acid/insulin glargine 50 U/mL composition.

In a 3 mL vial, 0.5 mL of an insulin glargine solution at a concentration of 100 U/mL, described in examples C3 or C4 is added a volume of 0.5 mL of the solution of co-polyamino acid/m-cresol/glycerin, so as to obtain a co-polyamino acid/m-cresol/glycerin 50 U/mL composition. A turbidity appears. The pH is adjusted to 7.1 by adding concentrated NaOH and the solution is placed in stasis in an oven at 40° C. for 1 night. This operation is carried out for various concentrations of co-polyamino acid. After one night at 40° C., the samples are visually inspected and subjected to a static light scattering measurement at a 1730 angle using a Zetasizer (Malvern). The minimum concentration of co-polyamino acid making it possible to solubilize insulin glargine is defined as the lowest concentration for which the co-polyamino acid/insulin glargine mixture at pH 7.1 is visually clear and has a diffused intensity lower than or equal to 1000 kcps (thousands of photons per second). The minimum concentrations of co-polyamino acid are presented in table 1b below.

TABLE 1b

Minimum concentration of co-polyamino acid to solubilize insulin glargine

| Co-polyamino acid | Minimum concentration of co-polyamino acid for the solubilization of glargine 50 U/mL at pH 7.1 (mg/mL) | Hydrophobic/insulin glargine ratio (mol/mol) |
|---|---|---|
| B22 | 0.75 | 0.61 |
| B7 | 0.75 | 0.64 |
| B13 | 0.88 | 0.54 |
| CE1 | 1.2 | 1.08 |
| CE2 | 1.0 | 0.83 |

The co-polyamino acid B22, B7 and B13 make it possible to solubilize insulin glargine with a mass concentration lower or equal to 0.88 mg/mL and with a hydrophobic/insulin glargine molar ratio lower or equal to 0.64.

TABLE 1c

Minimum ratio to solubilize insulin glargine.

| Co-polyamino acid | Minimum concentration of co-polyamino acid for the solubilization of glargine 50 U/mL at pH 7.1 (mg/mL) | Co-polyamino acid/insulin glargine ratio (mol/mol) |
|---|---|---|
| B2 | 0.75 | 0.27 |
| B3 | 0.87 | 0.32 |
| B9 | 0.87 | 0.33 |
| B15 | 1.0 | 0.27 |
| B18 | 0.79 | 0.26 |
| B19 | 1.0 | 0.37 |
| B21 | 0.7 | 0.24 |
| CE1 | 1.2 | 1.01 |
| CE2 | 1.0 | 0.45 |

The co-polyamino acids B2, B3, B9, B15, B18, B19 and B21 make it possible to solubilize insulin glargine with a mass concentration lower or equal to 1.25 mg/mL and with a co-polyamino acid/insulin glargine molar ratio lower or equal to 0.42.

Preparation Process CA6: Determination of the Minimum Concentration for Solubilizing Insulin Glargine at 50 U/mL at pH 7.1.

The preparation process follows the preparation process CA5, with one difference: to the parent solution of co-polyamino acid at pH 7-7.5, is added a concentrated solution of sodium chloride in order to attain the targets of the final composition, in addition to solutions of m-cresol and glycerin. The results are described in table 1d below.

TABLE 1d minimum ratio to solubilize insulin glargine

| | Minimum concentration of co-polyamino acid for the solubilization of glargine 50 U/mL at pH 7.1 | | |
|---|---|---|---|
| co-polyamino acid | NaCl (mM) | (mg/mL) | Hydrophobic/insulin glargine ratio (mol/mol) |
| B22 | 0 | 0.77 | 0.62 |
| | 5 | 0.63 | 0.51 |
| | 10 | 0.59 | 0.48 |

The addition of salt makes it possible to lower the concentration of co-polyamino acid B22 to the solubilization threshold of glargine.

Part CB—Compositions Comprising Insulin Glargine and Insulin Lispro

Preparation Process CB1: Preparation of a Diluted Co-Polyamino Acid/Insulin Glargine 43 (U/mL)/Insulin Lispro 13.5 (U/mL) Composition.

To a volume $V_{co\text{-}polyamino\ acid/diluted\ insulin\ glargine}$ of the diluted co-polyamino acid/insulin glargine 50 U/mL at pH 7.1 described in example CA1 is added one volume $V_{insulin\ lispro}$ of an insulin lispro 100 U/mL solution and water so as to obtain a co-polyamino acid/insulin glargine 43 (U/mL)/insulin lispro 13.5 (U/mL) composition.

Preparation Process CB2: Preparation of a Concentrated Co-Polyamino Acid Insulin Glargine/Insulin Lispro at pH 7.1

A concentrated co-polyamino acid/insulin glargine 43 (U/mL)/insulin lispro 13.5 composition described in example CB1 is concentrated by ultrafiltration with a 3 kDa membrane of regenerated cellulose (Amicon® Ultra-15 marketed by MILLIPORE). At the end of this ultrafiltration step, the retentate is clear and the concentration of insulin glargine in the composition is determined by reverse-phase chromatography (RP-HPLC). The concentrations of insulin glargine and insulin lispro in the composition are then adjusted to the desired value by dilution in a solution of the excipients m-cresol/glycerin/Tween 20 so as to obtain a final m-cresol concentration of 35 mM, Tween of 52 µM and an osmolarity of 300 mOsmol/kg. The pH is measured and adjusted, if necessary, to pH 7.1 by adding concentrated NaOH and HCl. This solution, at pH 7.1, visually clear, has a concentration of insulin glargine $C_{insulin\ glargine}$ (U/mL) and a concentration of insulin lispro $C_{insulin\ lispro} = C_{insulin\ glargine} \times 0.33$ and a concentration of co-polyamino acid $C_{co\text{-}polyamino\ acid}$ (mg/mL) = $C_{diluted\ co\text{-}polyamino\ acid}$ (mg/mL) × $C_{insulin\ glargine}$ (U/mL)/50 (U/mL).

Preparation Process of CB3: Preparation of a Concentrated Co-Polyamino Acid Insulin Glargine Acid/Insulin Lispro at pH 7.1

To a volume $V_{concentrated\ co\text{-}polyamino\ acid/insulin\ glargine}$ of the concentrated composition of co-polyamino acid/insulin glargine at pH 7.1 described in example CA3 is added a volume $V_{insulin\ lispro}$ of a lispro solution described in example C2. One volume of polysorbate 20 solution is added in order to obtain a final concentration of 52 µM. The resulting solution at pH 7.1, visually clear, has a concentration of insulin glargine $C_{insulin\ glargine}$ (U/mL), a concentration of insulin lispro of $C_{insulin\ lispro} = C_{insuline\ glargine} \times 0.33$ and a concentration of co-polyamino acid $C_{co\text{-}polyamino\ acid}$ (mg/mL) = $C_{diluted\ co\text{-}polyamino\ acid}$ (mg/mL) × $C_{insulin\ glargine}$ (U/mL)/50 (U/mL). The concentration of m-cresol is 35 mM and that of glycerin is 230 mM.

Preparation Process of CB4: Preparation of a Diluted Co-Polyamino Acid/Insulin Glargine 75 U/mL/Insulin Lispro 25 (U/mL) at pH 7.2.

To a volume of the concentrated co-polyamino acid/insulin glargine composition at pH 7.2 described in example CA3a or CA3b is added a volume of a lispro solution described in example C2. The concentration of zinc is adjusted to 0.5 mM by adding a concentrated solution of $ZnCl_2$. The pH is adjusted to 7.2 by adding a concentrated solution of hydrochloric acid. The resulting solution, visually clear, has an insulin glargine concentration of 75 U/mL and of insulin lispro of 25 U/mL. The concentration of m-cresol is 35 mM and that of glycerin is 230 mM.

Preparation Process CB5: Preparation of a Co-Polyamino Acid/Insulin Glargine 150 U/mL/Insulin Lispro 50 U/mL Composition at pH 7.2

To a volume of the concentrated co-polyamino acid/insulin glargine composition described in example CA4 or CA5 is added a volume of a lispro solution described in example C2. The concentration of zinc is adjusted to 1 mM by adding a concentrated solution of $ZnCl_2$. The pH is adjusted to 7.2 by adding a concentrated solution of hydrochloric acid. The resulting solution, visually clear, has a concentration of insulin glargine of 150 U/mL and of insulin lispro of 50 U/mL. The concentration of m-cresol is 35 mM and that of glycerin is 230 mM.

Example CB2 and CB3: Preparation of a Co-Polyamino Acid/Insulin Glargine 200 U/mL/Insulin Lispro 66 U/mL Compositions at pH 7.1

Co-polyamino acid/insulin glargine 200 U/mL/insulin lispro 66 U/mL compositions are prepared according to the processes described in CB2 and CB3 so as to obtain an insulin glargine concentration of $C_{insulin\ glargine}$=200 U/mL, a concentration of insulin lispro $C_{insulin\ lispro}$=66 U/mL and a co-polyamino acid concentration of $C_{co\text{-}polyamino\ acid}$ (mg/mL).

These compositions are presented in tables 2 and 2a.

TABLE 2

Compositions of insulin glargine (200 U/mL) and of insulin lispro (66 U/mL) in the presence of co-polyamino acid.

| Composition | Co-polyamino acid | Concentration of co-polyamino acid (mg/ml) | Insulin glargine (U/mL) | Insulin Lispro (U/mL) | Visual appearance of the solution |
|---|---|---|---|---|---|
| CB3-1 | B7 | 5 | 200 | 66 | Clear |
| CB2-2 | B1 | 6 | 200 | 66 | Clear |
| CB3-2 | B4 | 5 | 200 | 66 | Clear |

TABLE 2a

Compositions of insulin glargine (200 U/mL) and of insulin lispro (66 U/mL) in the presence of co-polyamino acid.

| Composition | Co-polyamino acid | Concentration of co-polyamino acid (mg/ml) | Insulin glargine (U/mL) | Insulin Lispro (U/mL) | Visual appearance of the solution |
|---|---|---|---|---|---|
| CB3-2 | B8 | 9 | 200 | 66 | Clear |
| CB3-3 | B7 | 17 | 200 | 66 | Clear |

Examples CB4 and CB5: Preparation of Concentrated Co-Polyamino Acid/Insulin Glargine Acid/Insulin Lispro Compositions at pH 7.2

Compositions of co-polyamino acid/insulin glargine 75 U/mL/insulin lispro 25 U/mL and compositions of co-polyamino acid/insulin glargine 150 U/mL/insulin lispro 50 U/mL are prepared according to the processes described in examples CB4 and CB5.

TABLE 2b

Compositions of insulin glargine (75 and 150 U/mL) and of insulin lispro (25 and 50 U/mL) in the presence of co-polyamino acid.

| Composition | Co-polyamino acid | Concentration of co-polyamino acid | Insulin glargine (U/mL) | Insulin Lispro (U/mL) | NaCl (mM) | Appearance |
|---|---|---|---|---|---|---|
| CB4-1 | B15 | 2.0 | 75 | 25 | 0 | Clear |
| CB5-1 |  | 4.0 | 150 | 50 | 0 | Clear |
| CB4-2 | B2 | 1.5 | 75 | 25 | 0 | Clear |
| CB5-2 |  | 3.0 | 150 | 50 | 0 | Clear |
| CB4-3 | B18 | 1.5 | 75 | 25 | 0 | Clear |
| CB4-4 |  | 1.2 | 75 | 25 | 5 | Clear |
| CB5-3 |  | 3.0 | 150 | 50 | 0 | Clear |
| CB4-5 | B3 | 1.8 | 75 | 25 | 0 | Clear |
| CB5-4 |  | 3.6 | 150 | 50 | 0 | Clear |
| CB4-6 | B9 | 1.8 | 75 | 25 | 0 | Clear |
| CB5-5 |  | 3.6 | 150 | 50 | 0 | Clear |
| CB4-7 | B22 | 1.5 | 75 | 25 | 0 | Clear |
| CB4-8 |  | 1.3 | 75 | 25 | 5 | Clear |
| CB5-6 |  | 3.0 | 150 | 50 | 0 | Clear |
| CB4-9 | B13 | 1.8 | 75 | 25 | 0 | Clear |
| CB5-7 |  | 3.6 | 150 | 50 | 0 | Clear |
| CB4-10 | B7 | 1.4 | 75 | 25 | 0 | Clear |
| CB4-11 | B14 | 2.0 | 75 | 25 | 0 | Clear |
| CB4-12 | B19 | 2.0 | 75 | 25 | 0 | Clear |
| CB4-13 | B20 | 3.6 | 75 | 25 | 0 | Clear |
| CB4-14 | B21 | 1.4 | 75 | 25 | 0 | Clear |
| CB5-9 |  | 2.8 | 150 | 50 | 0 | Clear |
| CB4-15 | CE1 | 2.0 | 75 | 25 | 0 | Clear |
| CB4-16 | CE2 | 2.0 | 75 | 25 | 0 | Clear |

The co-polyamino acids make it possible to solubilize insulin glargine in the presence of insulin lispro at neutral pH and to lead to a clear solution.

Part CD—Results
Proof of the Physical Stability of Compositions According to the Invention by the Study of the Compositions Prepared Above Example CD1: Dynamically Accelerated Stability at 25° C.

3 mL vials filled with 1 mL of co-polyamino acid/insulin glargine composition or co-polyamino acid/insulin glargine/prandial insulin composition are placed vertically on an orbital shaker. The shaker is placed in an oven at 25° C. and the vials are shaken at 250 rpm. The vials are visually inspected daily/weekly in order to detect the appearance of visible particles or turbidity. This inspection is carried out according to the recommendations of the European Pharmacopoeia (EP 2.9.20): the vials are illuminated by at least 2000 Lux and are observed in front of a white background and a black background. The number of days of stability correspond to the time from which at least 2 of the vials show visible particles or are turbid.

The result of accelerated stability with co-polyamino acid B4 is shown in Table 3.

TABLE 3 dynamic stability results of the co-polyamino acid B4/insulin glargine (200 U/mL)/insulin lispro (66 U/mL) composition at 25° C.

| Composition | Co-polyamino acid | Concentration of co-polyamino acid (mg/ml) | Stability in days |
|---|---|---|---|
| CA3-1 | B4 | 5 | >12 |

The co-polyamino acid B4 makes it possible to solubilize insulin glargine in the presence of insulin lispro at neutral pH and to lead to a composition with good physical stability.

Example CD2: Statically Accelerated Stability at 30° C.

At least 5 3 mL cartridges filled with 1 mL of co-polyamino acid/insulin glargine/prandial insulin composition are placed in an oven at 30° C. under static conditions. The cartridges are visually inspected bimonthly in order to detect the appearance of visible particles or of turbidity. This inspection is carried out according to the recommendations of the European Pharmacopoeia (EP 2.9.20): the cartridges are illuminated by least 2000 Lux and are observed in front of a white background and a black background. The number of weeks of stability correspond to the time from which the majority of the cartridges show visible particles or are turbid, compared to a reference standard.

The accelerated stability result under static conditions are presented in table 4 below.

TABLE 4

Results of the stabilities of co-polyamino acid/insulin glargine/insulin lispro compositions at 30° C. under static conditions.

| Composition | Co-polyamino acid | Concentration in co-polyamino acid (mg/ml) | Stability at 30° C. (week) |
|---|---|---|---|
| CB4-2 | B2 | 1.5 | >8 |
| CB4-7 | B1 | 1.5 | >18 |
| CB4-9 | B13 | 1.8 | >23 |
| CB4-12 | B19 | 2.0 | >8 |
| CB4-13 | B20 | 3.6 | >8 |
| CB5-6 | B22 | 3.0 | >18 |

Example CD3: Precipitation of Insulin Glargine after Mixture of the Co-Polyamino Acid/Insulin Glargine 75 U/mL/Insulin Lispro 25 U/mL Compositions with Albumin This test highlights the precipitation of insulin glargine when injected in a simulated physiological medium at physiological pH and ionic strength and containing albumin. These conditions make it possible to mimic the behavior of the composition during sub-cutaneous injection. To 100 μL of a co-polyamino acid/insulin glargine 75 U/mL/insulin lispro 25 U/mL composition are added 100 μL of bovine albumin solution at 20 mg/mL in a phosphate buffer at pH 7.4. The phosphate buffer (PBS or phosphate buffer saline) is concentrated so that the contents in NaCl and in phosphate are respectively 140 mM and 10 mM after mixing with the composition. The precipitation of glargine in this medium is monitored at room temperature (20-25° C.) by absorbance measurements at 450 nm of the mixtures for 30 minutes. The absorbance measurements are performed using a UV-visible reader of multi-well plates.

The absorbance increases until it reaches a plateau. Glargine precipitation time is defined as the time required for the measured absorbance to be greater than or equal to 80% of the plateau value. The precipitation times obtained with the compositions described above are shown in table 5.

TABLE 5

Precipitation time for insulin glargine after mixture of co-polyamino acid/insulin glargine/insulin lispro compositions with a medium that simulates the sub-cutaneous medium.

| Composition | Co-polyamino acid | Concentration en co-polyamino acid (mg/ml) | Precipitation time (minutes) |
|---|---|---|---|
| CB4-2 | B2 | 1.5 | 3 |
| CB4-7 | B1 | 1.5 | 0.5 |

TABLE 5-continued

Precipitation time for insulin glargine after mixture of co-polyamino acid/insulin glargine/insulin lispro compositions with a medium that simulates the sub-cutaneous medium.

| Composition | Co-polyamino acid | Concentration en co-polyamino acid (mg/ml) | Precipitation time (minutes) |
|---|---|---|---|
| CB4-9 | B13 | 1.7 | 0.5 |
| CB4-12 | B19 | 2.0 | 2 |
| CB4-13 | B20 | 3.6 | 3 |
| CB4-15 | CE1 | 2.0 | 4 |
| CB4-16 | CE2 | 2.0 | 4 |

The co-polyamino acid/insulin glargine/insulin lispro compositions of the invention lead to a rapid precipitation of glargine after mixing with a medium that simulates the sub-cutaneous medium.

Part D: Pharmacokinetics

D1: Measurement Protocol for the Pharmacokinetics of Insulin Glargine and Insulin Lispro Formulations.

Studies were conducted in dogs for the purpose of evaluating the pharmacokinetics of insulins after administration of a co-polyamino acid B22/insulin glargine composition (150 U/mL)/insulin lispro (50 U/mL).

The pharmacokinetic profiles of insulin glargine (sum of the circulating concentration of insulin glargine and of its main metabolite M1) and of insulin lispro were obtained for this composition.

Ten animals that had been fasting for about 17.5 hours were injected subcutaneously with a 0.68 U/kg dose of insulin. Blood samples were taken during the 16 hours following administration in order to track the pharmacokinetics of insulins. Levels of glargine, glargine-M1 and lispro were determined using a specific bioanalysis method.

The following are the determined pharmacokinetic parameters:

$AUC_{0-1\,h}$, $AUC_{0-2\,h}$, $AUC_{10-16\,h}$ corresponding to the area below the curve of insulin glargine concentrations (and its metabolite, M1) as a function of the time from, respectively, 0 to 1 h, 0 to 2 h and 10 to 16 h post-administration;

$AUC_{0-30\,min}$, $AUC_{0-1\,h}$, $AUC_{8-16\,h}$ corresponding to the area below the curve for concentrations of insulin lispro as a function of the time, respectively, from 0 to 0.5 h, 0 to 1 h and 8 to 16 h post-administration;

$AUC_{last}$ corresponding to the area below the curve from time 0 to the time of the last measurement taken from the subject.

Table 6 below gives various pharmacokinetic parameters for insulin glargine and insulin lispro.

TABLE 6

Average pharmacokinetic parameters (ratio of averages) of composition CB5-6 comprising the co-polyamino acid B22/insulin glargine 150 U/mL/insulin lispro 50 U/mL.

| | Insulin glargine (150 U/mL) | | | Insulin Lispro (50 U/mL) | | |
|---|---|---|---|---|---|---|
| | $AUC_{0-1\,h}/AUC_{last}$ (%) | $AUC_{0-2\,h}/AUC_{last}$ (%) | $AUC_{10-16\,h}/AUC_{last}$ (%) | $AUC_{0-30\,min}/AUC_{last}$ (%) | $AUC_{0-1\,h}/AUC_{last}$ (%) | $AUC_{8-16\,h}/AUC_{last}$ (%) |
| CB5-6 | 24.7 | 35.4 | 14.9 | 33.5 | 60.1 | 0.6 |

The obtained results show that, on one hand, the glargine component of the formulation is rapidly absorbed ($AUC_{0-1\,h}$ to $AUC_{0-2\,h}$) while preserving its basal nature with significant coverage of the last portion of the observation time ($AUC_{10-16\,h}$). On the other hand, the lispro component is rapidly absorbed ($AUC_{0-30\,min}$ to $AUC_{0-1\,h}$) and maintains its prandial nature. Indeed, there was no more lispro observed after 8 h ($AUC_{8-16\,h}$).

The invention claimed is:

1. A composition in the form of an aqueous injectable solution whose pH is comprised from 6.0 to 8.0, comprising at least:
  a basal insulin whose isoelectric point pI is comprised from 5.8 to 8.5; and
  a co-polyamino acid bearing carboxylate charges and hydrophobic radicals -Hy, said co-polyamino acid bearing carboxylate charges and hydrophobic radicals -Hy having units selected from the group consisting of glutamic units, aspartic units, and units according to formula XXXa':

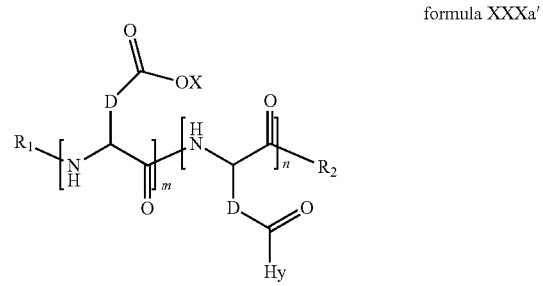

formula XXXa' wherein the hydrophobic radicals -Hy are according to formula X below:

Formula X

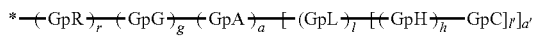

in which

GpR is chosen from the radicals according to formulas VII, VII' or VII":

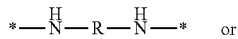   Formula VII or

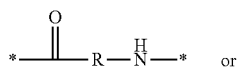   Formula VII' or

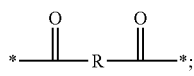   Formula VII";

GpG and GpH are identical or different and each is chosen from the radicals according to formulas XI or XI':

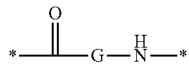   Formula XI

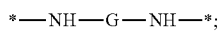   Formula XI'

GpA is chosen from the radicals according to formula VIII:

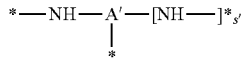   Formula VIII in which A' is chosen from the radicals according to formula VIII', VIII" or VIII'":

   Formula VIII'

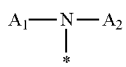   Formula VIII"

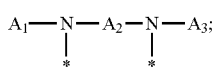   Formula VIII'"

GpL is chosen from the radicals according to formula XII:

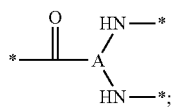   Formula XII

GpC is a radical according to formula IX:

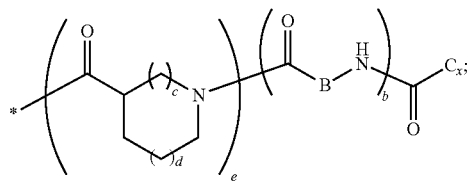   Formula IX the * indicates the attachment sites of the different groups bonded by an amide function;
a is an integer equal to 0 or to 1 and a'=1 if a=0 and a'=1, 2 or 3 if a=1;
a' is an integer equal to 1, to 2, or to 3;
b is an integer equal to 0 or to 1;
c is an integer equal to 0 or to 1, and if c is equal to 0, then d is equal to 1 or to 2;
d is an integer equal to 0, to 1, or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6;
l is an integer equal to 0 or 1 and l'=1 if l=0, and l'=2 if l=1;
r is an integer equal to 0, to 1, or to 2, and
s' is an integer equal to 0 or 1, and
if e is different from 0, then at least one of g, h or l is different from 0; and
if a=0, then l=0;
A, $A_1$, $A_2$ and $A_3$, identical or different, are linear or branched alkyl radicals comprising 1 to 8 carbon atoms, optionally substituted by a radical derived from a saturated, unsaturated or aromatic ring;
B is a linear or branched alkyl radical comprising 1 to 9 carbon atoms, optionally comprising an aromatic nucleus, or an unsubstituted ether or polyether radical comprising from 4 to 14 carbon atoms and from 1 to 5 oxygen atoms;
$C_x$ is a linear or branched monovalent alkyl radical, optionally comprising a cyclic part, in which x indicates the number of carbon atoms and:
when the hydrophobic radical -Hy carries 1-GpC, then $9 \leq x \leq 25$,
when the hydrophobic radical -Hy carries 2-GpC, then $9 \leq x \leq 15$,
when the hydrophobic radical -Hy carries 3-GpC, then $7 \leq x \leq 13$,
when the hydrophobic radical -Hy carries 4-GpC, then $7 \leq x \leq 11$,
when the hydrophobic radical -Hy carries at least 5-GpC, then $6 \leq x \leq 11$;
G is a linear or branched alkyl radical of 1 to 8 carbon atoms, with said alkyl radical bearing one or more free carboxylic acid functions;
R is a radical chosen from the group consisting of a divalent alkyl radical, linear or branched, comprising 1 to 12 carbon atoms, a divalent alkyl radical, linear or branched, comprising 1 to 12 carbon atoms bearing at least one —$CONH_2$ functions, and a unsubstituted ether or polyether radical comprising from 4 to 14 carbon atoms and 1 to 5 oxygen atoms;

the hydrophobic radical(s) -Hy according to formula X being bonded to the co-polyamino acid:
via a covalent bond between a carbonyl of the hydrophobic radical -Hy and a nitrogen atom borne by the co-polyamino acid, thus forming an amide function derived from the reaction of an amine function borne by the co-polyamino acid and an acid function borne by the precursor -Hy' of the hydrophobic radical -Hy, or
via a covalent bond between a nitrogen atom of the hydrophobic radical -Hy and a carbonyl borne by the co-polyamino acid, thus forming an amide function derived from the reaction of an amine function of the precursor -Hy' of the hydrophobic -Hy radical and an acid function borne by the co-polyamino acid;
the ratio M between the number of hydrophobic radicals and the number of glutamic and aspartic units being from 0<M≤0.5;
when several hydrophobic radicals are borne by a co-polyamino acid, then they are identical or different;
the degree of polymerization DP in glutamic or aspartic units of the co-polyamino acid is comprised from 5 to 250;
free carboxylic acid functions being in the form of an alkali metal salt chosen from the group consisting of $Na^+$ and $K^+$;
D represents, independently, either a —$CH_2$— group (aspartic unit) or a —$CH_2$—$CH_2$— group (glutamic unit),
$R_1$ is a hydrophobic radical -Hy or a radical chosen from the group consisting of an H, a linear acyl group comprising from 2 to 10 carbon atoms, a branched acyl group comprising from 4 to 10 carbon atoms, a benzyl, a terminal amino acid unit and a pyroglutamate,
$R_2$ is a hydrophobic radical -Hy or a —NR'R" radical, R' and R", either identical or different, being chosen from the group consisting of H, the linear or branched or cyclic alkyls comprising from 2 to 10 carbon atoms and benzyl, and said R' and R" alkyls may form together one or more saturated, unsaturated and/or aromatic cycle(s), and/or may comprise heteroatoms, chosen from the group consisting of O, N and S,
X represents a cationic entity chosen from the group consisting of $Na^+$ and $K^+$, and
n+m represents the degree of polymerization DP of the co-polyamino acid, namely, the average number of monomeric units per co-polyamino acid chain and 5≤n+m≤250.

2. The composition according to claim 1,
wherein in formula XXXa' of the co-polyamino acid bearing carboxylate charges and hydrophobic radicals:
D represents, independently, either a —$CH_2$— group (aspartic unit) or a —$CH_2$—$CH_2$— group (glutamic unit),
$R_1$ is a radical chosen from the group consisting of an H, a linear acyl group comprising from 2 to 10 carbon atoms, a branched acyl group comprising from 4 to 10 carbon atoms, a benzyl, a terminal amino acid unit and a pyroglutamate,
$R_2$ is a hydrophobic radical -Hy or a —NR'R" radical, R' and R", either identical or different, being chosen from the group consisting of H, the linear or branched or cyclic alkyls comprising from 2 to 10 carbon atoms and benzyl, and said R' and R" alkyls may form together one or more saturated, unsaturated and/or aromatic cycle(s), and/or may comprise heteroatoms, chosen from the group consisting of O, N and S, X represents a cationic entity chosen from the group consisting of $Na^+$ and $K^+$, and
n+m represents the degree of polymerization DP of the co-polyamino acid, namely, the average number of monomeric units per co-polyamino acid chain and 5≤n+m≤250; and
wherein in formula X of the hydrophobic radicals -Hy:
r=1 and GpR is a radical according to formula VII:

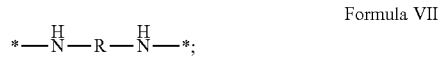

Formula VII

GpG and GpH are each a radical according to formula XI:

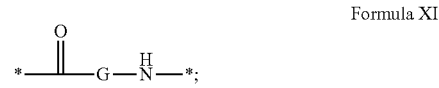

Formula XI

GpC is a radical according to formula IX:

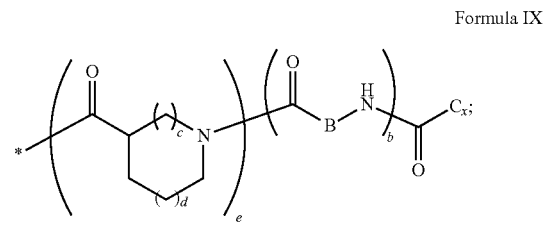

Formula IX the * indicates the attachment sites of the different groups bonded by an amide function;
a is 0;
a' is an integer equal to 1;
b is an integer equal to 0 or to 1;
c is an integer equal to 0 or to 1, and if c is equal to 0, then d is equal to 1 or to 2; and
d is an integer equal to 0, to 1, or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6;
l is 0 and l' is 1; and
if e is different from 0, then at least one of g or h is different from 0; and
B is a linear or branched alkyl radical comprising 1 to 9 carbon atoms, optionally comprising an aromatic nucleus, or an unsubstituted ether or polyether radical comprising from 4 to 14 carbon atoms and from 1 to 5 oxygen atoms;
$C_x$ is a linear or branched monovalent alkyl radical, optionally comprising a cyclic part, in which x indicates the number of carbon atoms and wherein 9≤x≤25;
G is a linear or branched alkyl radical of 1 to 8 carbon atoms, with said alkyl radical bearing one or more free carboxylic acid functions;
R is a radical chosen from the group consisting of a divalent alkyl radical, linear or branched, comprising 1 to 12 carbon atoms, a divalent alkyl radical, linear or branched, comprising 1 to 12 carbon atoms bearing at least one —$CONH_2$ functions, and a unsubstituted ether or polyether radical comprising from 4 to 14 carbon atoms and 1 to 5 oxygen atoms;

the hydrophobic radical(s) -Hy according to formula X being bonded to the co-polyamino acid:

via a covalent bond between a nitrogen atom of the hydrophobic radical -Hy and a carbonyl borne by the co-polyamino acid, thus forming an amide function derived from the reaction of an amine function of the precursor -Hy' of the hydrophobic -Hy radical and an acid function borne by the co-polyamino acid.

3. The composition according to claim 1, wherein the co-polyamino acid bearing carboxylate charges and hydrophobic radicals is chosen from the co-polyamino acids according to formula XXXa', in which $R_1=R'_1$ and $R_2=R'_2$, according to formula XXXa below:

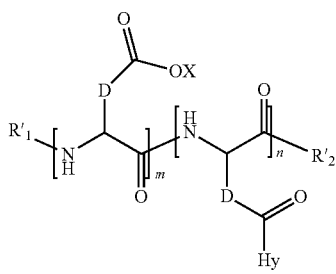

formula XXXa in which m, n, X, D and Hy have the definitions given above, $R'_1$ is a radical chosen from the group consisting of an H, a linear acyl group comprising from 2 to 10 carbon atoms, a branched acyl group comprising from 4 to 10 carbon atoms, a benzyl, a terminal amino acid unit and a pyroglutamate, $R'_2$ is a radical —NR'R", R' and R", either identical or different, being chosen from the group consisting of H, the linear or branched or cyclic alkyls comprising from 2 to 10 carbon atoms and benzyl, and said R' and R" alkyls may form together one or more saturated, unsaturated and/or aromatic cycle(s), and may comprise heteroatoms, chosen from the group consisting of O, N and S.

4. The composition according to claim 3, wherein in the co-polyamino acid bearing carboxylate charges and hydrophobic radicals, group D is a —$CH_2$— group (aspartic unit).

5. The composition according to claim 3, wherein in the co-polyamino acid bearing carboxylate charges and hydrophobic radicals, group D is a $CH_2$—$CH_2$— group (glutamic unit).

6. The composition according to claim 1, wherein the co-polyamino acid bearing carboxylate charges and hydrophobic radicals is chosen from the co-polyamino acids according to formula XXXa' in which n=0 according to formula XXXb below:

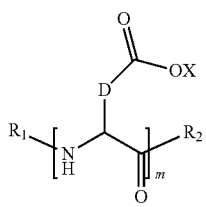

formula XXXb in which m, X, D, $R_1$ and $R_2$ have the definitions given above and at least one of $R_1$ or $R_2$ is a hydrophobic radical according to formula X.

7. The composition according to claim 6, wherein in the co-polyamino acid bearing carboxylate charges and hydrophobic radicals, group D is a —$CH_2$— group (aspartic unit).

8. The composition according to claim 6, wherein in the co-polyamino acid bearing carboxylate charges and hydrophobic radicals, group D is a $CH_2$—$CH_2$— group (glutamic unit).

9. The composition according to claim 6, wherein the co-polyamino acid bearing carboxylate charges and hydrophobic radicals is chosen from the co-polyamino acids according to formula XXXb in which $R_2$ is a hydrophobic radical according to formula X in which r=1 and GpR is according to formula VII.

10. The composition according to claim 1, wherein $R_1$ is a radical chosen from the group consisting of a linear acyl group comprising from 2 to 10 carbon atoms, a branched acyl group comprising from 4 to 10 carbon atoms, a benzyl, a terminal amino acid unit and a pyroglutamate.

11. The composition according to claim 10, wherein $R_1$ is a radical chosen from the group consisting of a linear acyl group comprising from 2 to 10 carbon atoms and a branched acyl group comprising from 4 to 10 carbon atoms.

12. The composition according to claim 1, wherein in the co-polyamino acid bearing carboxylate charges and hydrophobic radicals, group D is a —$CH_2$— group (aspartic unit).

13. The composition according to claim 1, wherein in the co-polyamino acid bearing carboxylate charges and hydrophobic radicals, group D is a $CH_2$—$CH_2$— group (glutamic unit).

14. The composition according to claim 1, wherein the basal insulin whose isoelectric point is comprised from 5.8 to 8.5 is insulin glargine.

15. The composition according to claim 1, wherein the composition comprises from 40 to 500 U/mL of basal insulin whose isoelectric point is comprised from 5.8 to 8.5.

16. The composition according to claim 1, wherein the concentration of co-polyamino acid bearing carboxylate charges and hydrophobic radicals is at most 60 mg/mL.

17. The composition according to claim 1, wherein the concentration of co-polyamino acid bearing carboxylate charges and hydrophobic radicals is at most 40 mg/mL.

18. The composition according to claim 1, wherein the concentration of co-polyamino acid bearing carboxylate charges and hydrophobic radicals is at most 20 mg/mL.

19. The composition according to claim 1, wherein the concentration of co-polyamino acid bearing carboxylate charges and hydrophobic radicals is at most 10 mg/mL.

20. A method for improving the physical chemical stability of a composition according to claim 1 by adding ionic species chosen from the group of anions, cations and/or zwitterions.

21. The composition according to claim 1, in the form of an aqueous injectable solution whose pH is comprised from 6.0 to 8.0, comprising at least:

the basal insulin whose isoelectric point pI is comprised from 5.8 to 8.5; and the co-polyamino acid bearing carboxylate charges and hydrophobic radicals -Hy, said hydrophobic radicals -Hy being according to formula X in which GpR is a radical from formula VII, GpH is a radical from XI and GpC is a radical from formula IX and in which e=1, b=0 and x=13.

22. The composition according to claim 1, in the form of an aqueous injectable solution whose pH is comprised from 6.0 to 8.0, comprising at least:
- the basal insulin whose isoelectric point pI is comprised from 5.8 to 8.5; and
- the co-polyamino acid bearing carboxylate charges and hydrophobic radicals -Hy,
- said hydrophobic radicals -Hy being according to formula X in which GpC is a radical from formula IXd:

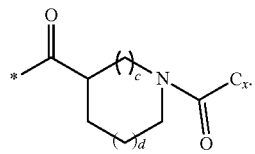

Formula IXd

23. The composition according to claim 1, in the form of an aqueous injectable solution whose pH is comprised from 6.0 to 8.0, comprising at least:
- the basal insulin whose isoelectric point pI is comprised from 5.8 to 8.5; and
- the co-polyamino acid bearing carboxylate charges and hydrophobic radicals -Hy,
- said co-polyamino acid being according to formula B1 below:

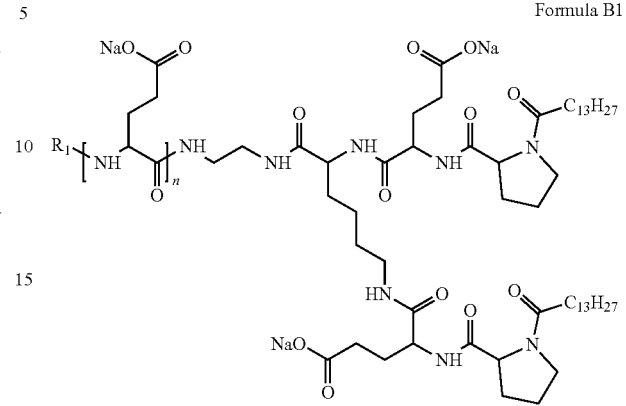

Formula B1 where $R_1$=H or pyroglutamate, and n is an integer in the range of from 5 to 250.

24. The composition according to claim 1, wherein the degree of polymerization DP in glutamic or aspartic units for the co-polyamino acid chains is from 10 to 40.

* * * * *